United States Patent [19]
Natsugari et al.

[11] Patent Number: 5,585,385
[45] Date of Patent: Dec. 17, 1996

[54] HETEROCYCLIC COMPOUNDS, THEIR PRODUCTION AND USE AS TACHYKININ REACTOR ANTAGONISTS

[75] Inventors: Hideaki Natsugari, Hyogo; Takenori Ishimaru; Takayuki Doi, both of Osaka, all of Japan

[73] Assignee: Takeda Chemical Industries, Ltd., Osaka, Japan

[21] Appl. No.: 338,762

[22] Filed: Nov. 10, 1994

[30] Foreign Application Priority Data

Nov. 10, 1993 [JP] Japan ................................. 5-281178
Dec. 28, 1993 [JP] Japan ................................. 5-337488
Mar. 3, 1994 [JP] Japan ................................. 6-033637
Jun. 21, 1994 [JP] Japan ................................. 6-138551

[51] Int. Cl.$^6$ .......................... A61C 31/44; A61C 31/47; A61C 31/435; C07D 471/04
[52] U.S. Cl. .......................... 514/300; 574/299; 574/301; 574/302; 546/114; 546/115; 546/122; 546/123; 546/153; 546/156; 546/167; 546/168
[58] Field of Search .................... 546/122, 123, 546/114, 115, 153, 156; 514/300, 299, 302, 301

[56] References Cited

U.S. PATENT DOCUMENTS 5,143,919  9/1992  Meguro ................................. 514/291

FOREIGN PATENT DOCUMENTS

| | | |
|---|---|---|
| 0354994A2 | 2/1990 | European Pat. Off. . |
| 0421456A2 | 4/1991 | European Pat. Off. . |
| 0481383A1 | 4/1992 | European Pat. Off. . |
| 0566069A1 | 10/1993 | European Pat. Off. . |
| 0569794A1 | 11/1993 | European Pat. Off. . |
| 0569795A1 | 11/1993 | European Pat. Off. . |
| 0585913A2 | 3/1994 | European Pat. Off. . |
| 6298757 | 10/1994 | Japan . |
| WO91/12249 | 8/1991 | WIPO . |

OTHER PUBLICATIONS

"Sintesi E. Attivita Farmacologica De Esteri Ed Amidi . . . ", F. Duro, et al., *Il Farmaco—Ed. Sc.*, vol. 33, pp. 73–80 (1978).

"Action of Grignard Reagents on 1-Benzoyran-2(H)-ones", A. M. Islam, et al., *Indian J. of Chem.*, vol. 17B, . 630–632 (1979).

"Reactions of 3[N–(p–Tolycarbamido)]–6–Bromocoumarin; . . . Derivatives", M. El–Kady, et al., *Egypt J. Chem.*, vol. 28, No. 1, . 19–28 (1985).

"Action of Grignard Reagents and of Ketones on 3–Phenyl Carbamoyl . . . ", M. El–Kady, et al., *Egypt J. Chem.*, vol. 28, No. 1, . 63–70 (1985).

"Some Reactions on 3N–Aryl–Carbamido Coumarines and 4–Methyl–5,6–Benzocoumarin", M. El–Mobayed, et al., *Anales de Quimica*, vol. 86, pp. 59–61 (1990).

"Synthese und antikonvulsive Aktivität von 3–Carbamoyl–4–aryl–isochinolin–1(2H)onen", Klaus Unverferth, et al., *Arch. Pharm.*, vol. 324, 809–814 (1991).

*Primary Examiner*—C. Warren Ivy
*Assistant Examiner*—Evelyn Huang
*Attorney, Agent, or Firm*—Foley & Lardner

[57] ABSTRACT

A novel compound represented by the formula:

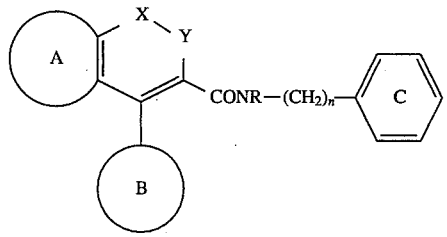

wherein Ring A and Ring B respectively stands for an optionally substituted homo- or hetero-cyclic ring, and at least one of them stands for an optionally substituted heterocyclic ring stand; Ring C stands for an optionally substituted benzene ring; R stands for a hydrogen atom or an optionally substituted hydrocarbon residue; one of X and Y stands for —NR$^1$— (R$^1$ stands for a hydrogen atom or an optionally substituted hydrocarbon residue) or —O—, and the other stands for—CO— or —CS—, or one of them stands for —N= and the other stands for =CR$^2$— (R$^2$ stands for a hydrogen atom, a halogen atom, an optionally substituted hydrocarbon residue, an optionally substituted amino group or an optionally substituted hydroxyl group); n denotes 1 or 2 or salts thereof which have an excellent tachykinin receptor antagonistic action and inhibitory action on plasma extravasation.

25 Claims, No Drawings

HETEROCYCLIC COMPOUNDS, THEIR PRODUCTION AND USE AS TACHYKININ REACTOR ANTAGONISTS

This invention relates to a novel heterocyclic amido compound having an excellent tachykinin receptor antagonistic action, a method for the production thereof and a composition containing the compound.

Tachykinin is a generic term denoting a group of neuropeptides. In mammalian animals, substance P, neurokinin-A, neurokinin-B are known. It is also known that by binding their respective receptors (neurokinin -1, neurokinin-2, neurokinin-3) present in the living body, these peptides exhibit a diversity of biological activities.

Among them, substance P is one of the neuropeptides known for the longest time of all and studied in the greatest detail. Its presence was confirmed in the substance extracted from the intestinal tubes of horses in 1931 and a peptide consisting of 11 amino acids, the structure being decided in 1971. Substance P is known to play a critical role as a transmitter substance in both the peripheral and central nervous system. This substance is also considered to be involved in a variety of morbid states (e.g. pain, inflammation, allergy, urinary frequency, respiratory tract disorders, mental diseases, etc.).

As compounds having substance P receptor antagonizing activity, the following are known.

(1) in JPA H1(1989)-287095 a compound of the formula:

$$R^1\text{—}A\text{—}D\text{—}Trp(R^2)\text{—}Phe\text{—}R^3$$

wherein $R^1$ stands for H or an amino-protecting group; $R^2$ stands for H, an amino-protecting group, a carbamoyl-(lower)alkyl group, a carboxyl(lower)alkyl group or a protected carboxyl(lower)alkyl group; $R^3$ stands for an ar(lower)alkyl group, a group represented by the formula:

(wherein $R^4$ and $R^5$ respectively stand for H, an aryl group or an optionally substituted lower alkyl group, or $R^4$ and $R^5$ are linked together to form a benzene-condensed lower alkylene group), or a group represented by the formula:

—OR⁶

(wherein $R^6$ stands for H, an aryl group or an optionally substituted lower alkyl group): A stands for a single bond or one or two amino acid residues, provided that, when A stands for a one amino acid residue of —D—Trp—, then $R^4$ is not hydrogen, and a salt thereof, (2) in EP-A-436,334, among others, a compound represented by the formula:

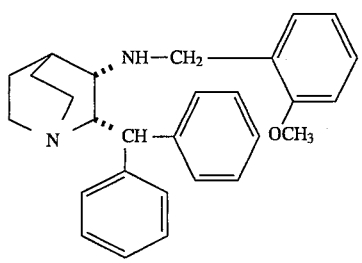

(3) in EP-A-429,366, among others, a compound represented by the formula:

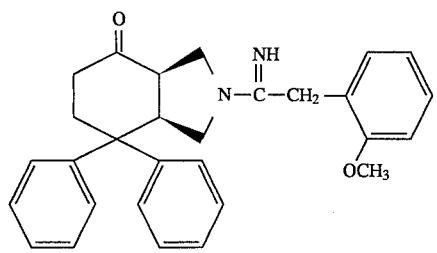

(4) in Journal of Medicinal Chemistry, 34, p 1751 (1991), among others, a compound represented by the formula:

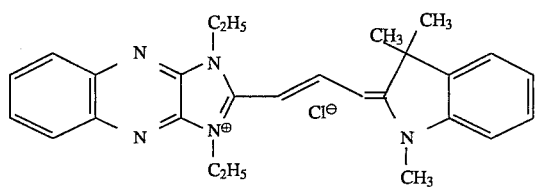

(5) in WO 91/09844, among others, a compound represented by the formula:

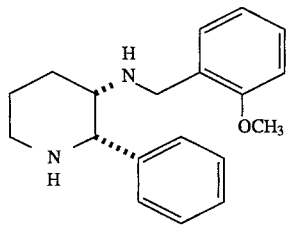

(6) in EP-A-522,808, among others, a compound represented by the formula:

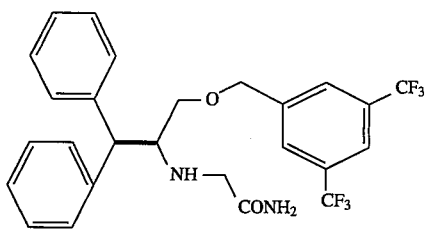

(7) in WO 93/01169, among others, a compound represented by the formula:

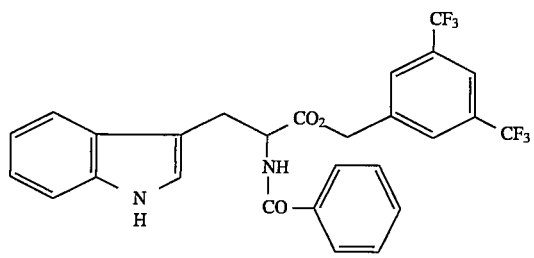

(8) in EP-A-522,456, among others, a compound represented by the formula:

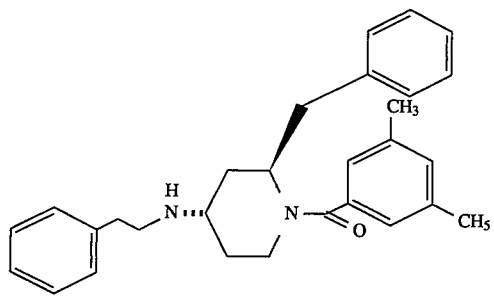

However, there has been no disclosure of a condensed heterocyclic amido compound having —CON< linked directly to the condensed heterocyclic ring which have a tachykinin receptor antagonistic activity.

And, for use as drugs for the treatment of the above-mentioned various diseases, no such compounds as satisfactory from the viewpoints of potent tachykinin receptor antagonizing activity, especially substance P receptor antagonistic activity, as well as other favorable properties such as safety and a sufficient long duration of action after administration, has been found yet. Circumstances being such as above, development of compounds having different chemical structures from those of known compounds, having excellent tachykinin receptor antagonizing activity and being sufficiently satisfactory as therapeutic drugs of said diseases has been desired.

The present inventors, taking the above circumstances into consideration, did much diligent research and study, and, as the result, succeeded in synthesizing, for the first time, a heterocyclic amido compound having, as a chemical characteristic feature, —CON< directly linked to the condensed heterocyclic ring, and having, as a partial structure represented by the formula:

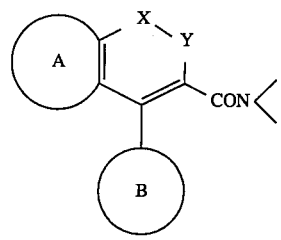

wherein all symbols are of the same meaning as defined hereinafter, and found that the compound has unexpectedly surprisingly excellent tachykinin receptor antagonizing activity, especially substance P receptor antagonistic activity, and that it is fully satisfactory as a medicine useful based on this activity, thus the present invention being accomplished.

More specifically started, the present invention relates to:

(1) a compound represented by the formula:

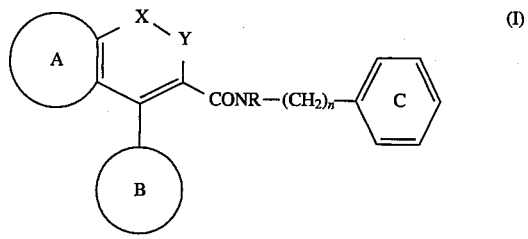

(I)

wherein Ring A and Ring B respectively stand for an optionally substituted homo- or hetero-cyclic ring, and at least one of them stands for an optionally substituted heterocyclic ring;

Ring C stands for an optionally substituted benzene ring;

R stands for a hydrogen atom or an optionally substituted hydrocarbon residue;

either one of X and Y stands for —$NR^1$— ($R^1$ stands for a hydrogen atom or an optionally substituted hydrocarbon residue) or —O—, and the other stands for —CO— or —CS—, or either one of them stands for —N= and the other stands for =$CR^2$— ($R^2$ stands for a hydrogen atom, a halogen atom, an optionally substituted hydrocarbon residue, an optionally substituted amino group or an optionally substituted hydroxyl group);

n denotes 1 or 2, or a salt thereof, (2) a compound as described above in (1), in which either one of Ring A and Ring B stands for an optionally substituted aromatic ring and the other stands for an optionally substituted aromatic heterocyclic ring, (3) a compound as above described in (2), in which the substituent or substituents of the optionally substituted aromatic ring are 1 to 4 substituents selected from the group consisting of a halogen atom, an optionally halogenated $C_{1-4}$ alkyl group, an optionally halogenated $C_{1-4}$ alkoxy group, an optionally halogenated $C_{1-4}$ alkylthio groups, a $C_{1-3}$ acyloxy group, a hydroxyl group, an amino group, a mono-$C_{1-4}$ alkyl amino group, a di-$C_{1-4}$ alkylamino group, a carboxyl group and a $C_{1-4}$ alkoxy-carbonyl group, (4) a compound as described above in (2), in which the aromatic heterocyclic ring is a 5- or 6-membered ring containing up to two kinds of hetero atoms selected from a nitrogen, a sulfur and an oxygen, (5) a compound as described above in (2), in which the substituent or substituents of the optionally substituted aromatic heterocyclic ring are 1 to 4 substituents selected from the group consisting of a halogen atom, an optionally halogenated $C_{1-4}$ alkyl group, an optionally halogenated $C_{1-4}$ alkoxy group, an optionally halogenated $C_{1-4}$ alkylthio group, a $C_{1-3}$ acyloxy group, a hydroxyl group, an amino group, a mono-$C_{1-4}$ alkylamino group, a di-$C_{1-4}$ alkylamino group, a carboxyl group and a $C_{1-4}$ alkoxy-carbonyl group, (6) a compound as described above in (1) to (5), in which Ring C may be substituted by have 1 to 3 substituents, each being selected from the group consisting of a halogen atom, an optionally halogenated $C_{1-4}$ alkyl group and an optionally halogenated $C_{1-4}$ alkoxy group, (7) a compound as described above in (1) to (5), in which —X—Y— is —$NR^{1a}$—CO—, —CO—$NR^{1a}$—, —O—CO—, —CO—O— or —N=C($R^{2a}$)— ($R^{1a}$ and $R^{2a}$ respectively stand for a hydrogen atom or a $C_{1-6}$ alkyl group), (8) a compound as described above in (1) to (5), in which R is a $C_{1-6}$ alkyl group, (9) a compound as described above in (1) to (5), in which n is 1,

(10) a compound as described above in (1), in the substituent or substituents of which the optionally substituted homo- or hetero-cyclic ring are 1 to 4 substituents selected from the group consisting of a halogen atom, an optionally halogenated $C_{1-4}$ alkyl group, an optionally halogenated $C_{1-4}$ alkylthio group, a $C_{1-3}$ acyloxy group, a hydroxyl group, an amino group, a mono-$C_{1-4}$ alkylamino group, a di-$C_{1-4}$ alkylamino group, a carboxyl group, a $C_{1-4}$ alkoxy-carbonyl group and an oxo group,

(11) a compound as described above in (1), in which the heterocyclic ring is a 5- or 6-membered ring containing up to two kinds of hetero-atoms selected from a nitrogen, a sulfur and an oxygen,

(12) a compound as described above in (1), in which the homo-cyclic ring is a 5- or 6-membered cyclic hydrocarbon,

(13) a compound as described above in (1), in which —X—Y— is —$NR^{1a}$—CO—, —CO—$NR^{1a}$— or —N=C($R^{2a}$)— ($R^{1a}$ and $R^{2a}$ respectively stand for a hydrogen atom or a $C_{1-6}$ alkyl group),

(14) a compound as described in (1) above, in which the heterocyclic ring represented by Ring A or B is a 5- or 6-membered heterocyclic ring containing 1 or 2 hetero atoms selected from a nitrogen and a sulfur, the homo-cyclic ring represented by Ring A or B is a 5- or 6-membered cyclic hydrocarbon group, and the hetero- and homo-cyclic ring represented by Ring A or B respectively may be substituted by 1 or 2 substituents selected from the group consisting of a halogen atom and an optionally halogenated $C_{1-4}$ alkyl group; Ring C may be substituted by 1 to 3 substituents selected from the group consisting of a halogen atom, an optionally halogenated $C_{1-4}$ alkyl group and an optionally halogenated $C_{1-4}$ alkoxy group; R is a hydrogen atom or a $C_{1-4}$ alkyl group; —X—Y— is —CO—$NR^{1a}$—, —$NR^{1a}$—CO or —N=C($R^{2a}$)— ($R^{1a}$ and $R^{2a}$ respectively stand for a hydrogen atom or a $C_{1-4}$ alkyl group); and n is 1,

(15) a compound as described above in (1), in which Ring A is a pyridine ring;
Ring B is a benzene ring which may be substituted by 1 to 3 substituents selected from the group consisting of a halogen atom, an optionally halogenated $C_{1-4}$ alkyl group and an optionally halogenated $C_{1-4}$ alkoxy group;
Ring C may be substituted by 1 to 3 substituents selected from the group consisting of a halogen atom, an optionally halogenated $C_{1-4}$ alkyl group and an optionally halogenated $C_{1-4}$ alkoxy group;
R is a hydrogen atom or a $C_{1-6}$ alkyl group;
X is —CO—;
Y is —$NR^{1a}$— ($R^{1a}$ stands for a hydrogen atom or a $C_{1-6}$ alkyl group); and
n is 1,

(16) N-[3,5-Bis(trifluoromethyl)benzyl]-7,8-dihydro-N,7-dimethyl-5-(4-methylphenyl)-8-oxo-6-pyrido[3,4-b]pyridinecarboxamide,

(17) N-[3,5-Bis(trifluoromethyl)benzyl]-5-(4-fluorophenyl)-7,8-dihydro-N,7-dimethyl-8-oxo-6-pyrido[3,4-b]pyridinecarboxamide,

(18) N-[3,5-Bis(trifluoromethyl)benzyl]-4-(4-fluorophenyl)- 6,7-dihydro-N,6-dimethyl-7-oxo-5-thieno[2,3-c]pyridinecarboxamide,

(19) N-[3,5-Bis(trifluoromethyl)benzyl]-1,2,5,6,7,8-hexahydro-N,2,7-trimethyl-4-(4-methylphenyl)-1-oxo-3-pyrido[3,4-c]pyridinecarboxamide,

(20) a process for producing a compound as described in (1), which comprises reacting a compound represented by the formula:

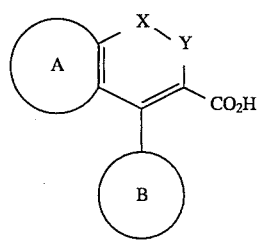

(II)

wherein all symbols are of the same meanings as defined above in (1) or a salt thereof or a reactive derivative thereof with a compound represented by the formula:

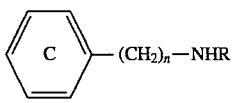

(III)

herein all symbols are of the same meaning as defined above in (1), or a salt thereof, In the above formula, Ring A and Ring B are respectively an optionally substituted homo- or hetero-cyclic ring, and at least one of them being an optionally substituted heterocyclic ring.

The "homo- or hetero-cyclic ring" is (i) an aromatic or non-aromatic heterocyclic ring which are, for example, contain one or two kinds of hetero-atoms selected from a nitrogen atom, a sulfur atom and an oxygen atom, preferably one or two of them in addition to carbon atoms, or (ii) a cyclic hydrocarbon consisting of carbon atoms.

As the "aromatic heterocyclic ring", use is made of, for example, a 5- or 6-membered aromatic heterocyclic ring containing one or two hetero-atoms selected from a nitrogen atom, an oxygen atom and a sulfur atom in addition to carbon atoms (e.g. a pyridine, pyrazine, pyrimidine, pyridazine, pyrrole, imidazole, pyrazole, triazole, thiophene, furan, thiazole, isothiazole, oxazole and isoxazole ring, etc.), preferably, for example, a pyridine, pyrazine and thiophene ring, etc., and, besides, a thiazole ring, for example, is preferable. Especially, a 6-membered heterocyclic ring containing one or two nitrogen atoms in addition to carbon atoms, for example, a pyridine and pyrazine ring, etc., or a 5-membered aromatic heterocyclic ring containing one sulfur atom in addition to carbon atoms, for example, a thiophene ring, etc. are commonly employed.

As the "non-aromatic heterocyclic ring", a 5- or 6-membered non-aromatic heterocyclic ring containing one or two hetero atoms selected from a nitrogen atom, an oxygen atom and a sulfur atom in addition to carbon atoms. For example, regarding ring A, use is made of a tetrahydropyridine, dihydropyridine, tetrahydropyrazine, tetrahydropyrimidine, tetrahydropyridazine, dihydropyran, dihydropyrrole, dihydroimidazole, dihydropyrazole, dihydrothiophene, dihydrofuran, dihydrothiazole, dihydroisothiazole, dihydrooxazole and dihydroisoxazole ring, among others, and, regarding ring B, use is made of, in addition to the above-mentioned ones, a piperidine, pyperazine, hexahydropyrimidine, hexahydropyridazine, tetrahydropyran, morpholine, pyrrolidine, imidazolidine, pyrazolidine, tetrahydrothiophene and tetrahydrofuran, tetrahydrothiazole, tetrahydroisothiazole, tetrahydrooxazole, tetrahydroisoxazole ring, etc. Preferably, regarding Ring A, a 6-membered non-aromatic heterocyclic ring containing one or two nitrogen atoms in addition to carbon atoms, for example, is commonly used, as exemplified by a tetrahydropyridine, tetrahydropyrimidine and tetrahydropyridazine ring, etc. Especially, a tetrahydropyridine ring, for example, is commonly used.

Regarding Ring B, for example, a 6-membered non-aromatic heterocyclic ring containing one or two nitrogen atoms in addition to carbon atoms is used, especially a piperazine ring or the like is commonly employed.

As the "cyclic hydrocarbon", use is made of, for example, a 5- or 6-membered cyclic hydrocarbon. For example, as Ring A, use is made of a benzene, a $C_{5-6}$ cycloalkene (e.g. cyclopentene, cyclohexene, etc.), and, as Ring B, use is made of, in addition to the above-mentioned ones, a $C_{5-6}$ cycloalkane (e.g. cyclohexane, cyclopentane, etc.). As Ring A, for example, a 6-membered homocyclic ring such as a benzene ring, a cyclohexene ring or the like is preferable, and, especially, a benzene ring is conventionally used. As Ring B, a 6-membered homocyclic ring such as a benzene ring, cyclohexane ring, etc. is preferable, and, especially, a benzene ring is often used.

It is preferable when either one of Ring A or Ring B is an optionally substituted aromatic ring and the other is an optionally substituted aromatic heterocyclic ring.

As the "aromatic ring", use is made of, for example, (i) a 5- or 6-membered aromatic heterocyclic ring containing one or two kinds of hetero-atoms selected from a nitrogen atom, a sulfur atom and an oxygen atom, preferably one or two of them in addition to carbon atoms (e.g. pyridine, pyrazine, pyrimidine, pyridazine, pyrrole, imidazole, pyrazole, triazole, thiophene, furan, thiazole, isothiazole, oxazole and isoxazole ring, etc.), or (ii) a benzene ring.

Substituents which the "aromatic ring" optionally has, include those similar to substituents which the Ring A and Ring B optionally have as described in the following.

As the "aromatic heterocyclic ring" of "optionally substituted aromatic heterocyclic ring", use is made of similar ones to the afore-mentioned "5- or 6-membered aromatic heterocyclic ring".

As substituents of the "optionally substituted aromatic heterocyclic ring", use is made of substituents similar to those which the Ring A and Ring B optionally have as described in the following.

Ring A and Ring B are, preferably, when one of them is a benzene ring and the other is a 5- or 6-membered aromatic heterocyclic ring.

As the "aromatic heterocyclic ring", use is made of, for example, a pyridine, pyrazine, pyrimidine, pyridazine, pyrrole, imidazole, pyrazole, triazole, thiophene, furan, thiazole, isothiazole and isoxazole ring; preferably, a pyridine, pyrazine and thiophene ring, etc. are conventionally employed. And, for example, a pyrrole and thiazole ring, etc. are also preferable. Especially, a 6-membered N-containing heterocyclic ring containing one or two nitrogen atoms in addition to carbon atoms, for example, a pyridine and pyrazine ring, etc., or a 5-membered aromatic heterocyclic ring containing one sulfur atom in addition to carbon atoms, for example, a thiophene ring is conventionally employed.

As substituents which "homo- or hetero-cyclic ring", "aromatic heterocyclic ring", "non-aromatic heterocyclic ring", "cyclic hydrocarbon", "aromatic ring" and "benzene ring" shown by Ring A and Ring B may have, use is made of, for example, a halogen atom, an optionally substituted alkyl group, an optionally halogenated alkoxy group, an optionally halogenated alkylthio group, $C_{1-7}$ acylamino group (e.g. formamino, acetylamino, propionylamino, butyrylamino, benzoylamino, etc.), a $C_{1-3}$ acyloxy group (e.g. formyloxy, acetoxy, propionyloxy, etc.), a hydroxyl group, a nitro group, a cyano group, an amino group, a mono- or di-$C_{1-4}$ alkylamino group (e.g. methylamino, ethylamino, propylamino, dimethylamino, diethylamino, etc.), a cyclic amino group (e.g.5- to 9-membered cyclic amino group optionally containing, besides nitrogen atom, 1 to 3 hetero-atoms such as an oxygen atom, a sulfur atom, etc., more practically, such as pyrrolidino, piperidino, morpholino, etc.), a $C_{1-4}$ alkyl-carbonylamino group (e.g. acetylamino, propionylamino, butyrylamino, etc.), a alkylsulfonylamino group (e.g. methylsulfonylamino, ethylsulfonylamino, etc.), a $C_{1-4}$ alkoxy-carbonyl group (e.g. methoxycarbonyl, ethoxycarbonyl, propoxycarbonyl, etc.), a carboxyl group, a $C_{1-6}$ alkyl-carbonyl group (e.g. methylcarbonyl, ethylcarbonyl, propylcarbonyl, etc.), a carbamoyl group, a mono or di-$C_{1-4}$ alkylcarbamoyl group (e.g.methylcarbamoyl, ethylcarbamoyl, dimethylcarbamoyl, diethylcarbamoyl, etc.), a $C_{1-6}$ alkylsulfonyl group (e.g. methylsulfonyl, ethylsulfonyl, propylsulfonyl, etc.), etc., and, further, for example, an oxo group.

The number of the substituents is 1 to 3.

As the "halogen atom" which Ring A and Ring B may have, use is made of, for example, fluorine, chlorine, bromine, iodine, etc., and preferable ones include fluorine, chlorine.

As the "optionally substituted alkyl group" which Ring A and Ring B may have, use is conventionally made of a $C_{1-6}$ alkyl group (e.g. methyl, ethyl, propyl, isopropyl, butyl, isobutyl, sec-butyl, tert-butyl, etc.) which may have 1 to 4 substituents selected from the group consisting of, for example, a hydroxyl group, an amino group, a carboxyl group, a nitro group, a mono- or di-$C_{1-6}$ alkylamino group (e.g. methylamino, ethylamino, dimethylamino, diethylamino, etc.), a $C_{1-6}$ alkyl-carbonyloxy group (e.g. acetoxy, ethylcarbonyloxy, etc.) and a halogen atom (e.g. fluorine, chlorine, bromine etc.). Especially, an optionally halogenated alkyl group are preferable, and a $C_{1-6}$ alkyl group or those substituted with 1 to 5 of such halogen atoms as mentioned above, as exemplified by methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl, 5-trifluoromethylpentyl, etc., and preferably $C_{1-4}$ alkyl group or those substituted with 1 to 3 halogen atoms as mentioned above, exemplified by methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl, etc.

As the "optionally halogenated alkoxy group" which Ring A and Ring B may have, use is conventionally made of a $C_{1-6}$ alkoxy group or those substituted with 1 to 5 of such halogen atoms as mentioned above, exemplified by methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy, hexyloxy, etc., and preferably a $C_{1-4}$ alkoxy group or those substituted with 1 to 3 of such halogen atoms as mentioned above, exemplified by methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.

As the "optionally halogenated alkylthio group" which Ring A and Ring B may have, use is conventionally made of a $C_{1-6}$ alkylthio group or those substituted with 1 to 5 of such halogen atoms as mentioned above, exemplified by methylthio, difluoromethylthio, trifluoromethylthio, ethylthio, propylthio, isopropylthio, butylthio, 4,4,4-trifluorobutylthio, pentylthio, hexylthio, etc., and, preferably, a $C_{1-4}$ alkylthio group or those substituted with 1 to 3 of such halogen atoms as mentioned above, exemplified by metylthio, difluoromethylthio, trifluoromethylthio, ethylthio, isopropylthio, butylthio, 4,4,4-trifluorobutylthio, etc.

Hereinafter, the number of halogen atoms of the term "optionally halogenated" used in the description ranges from 1 to 5, preferably 1 to 3.

Examples of preferable substituents which the ring A and Ring B may have, include a halogen atom (e.g. fluorine, chlorine, bromine, etc.), an optionally halogenated $C_{1-4}$ alkyl group (e.g. methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl, etc.), an optionally halogenated $C_{1-4}$ alkoxy group (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.), an optionally halogenated $C_{1-4}$ alkylthio group (e.g. methylthio, difluoromethylthio, trifluoromethylthio, ethylthio, propylthio, isopropylthio, butylthio, 4,4,4-trifluorobutylthio, etc.), a $C_{1-3}$ acyloxy group (e.g. formyloxy, acetoxy, propionyloxy, etc.), a hydroxyl group, an amino group, a mono- or di-$C_{1-4}$ alkylamino group (e.g. methylamino, ethylamino, propylamino, dimethylamino, diethylamino, etc.), a carboxyl group and a $C_{1-4}$ alkoxy-carbonyl group (e.g. methoxycarbonyl, ethoxycarbonyl, propoxycarbonyl, etc.), and an oxo group.

As more preferable substituents which the Ring A and Ring B may have, use is conventionally made of a halogen atom (e.g. fluorine, chlorine, bromine, etc.), an optionally halogenated $C_{1-4}$ alkyl group (e.g. methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl, etc.), an optionally halogenated $C_{1-4}$ alkoxy group (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.), a hydroxyl group, an amino group, a mono- or di-$C_{1-4}$ alkylamino group (e.g. methylamino, ethylamino, propylamino, dimethylamino, diethylamino, etc.), a $C_{1-3}$ acyloxy group (e.g. formyloxy, acetoxy, propionyloxy, etc.), an oxo group, etc. Among them, especially a halogen atom (e.g. fluorine, chlorine, bromine, etc.), an optionally halogenated $C_{1-4}$ alkyl group (e.g. methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-fluoromethylethyl, butyl, 4,4,4-trifluorobutyl, isobutyl, sec-butyl, tert-butyl, etc.) and an optionally halogenated $C_{1-4}$ alkoxy groups (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.), etc. are conventionally used.

Substituents on the Ring A and Ring B may be located on any substitutable positions of the rings, and, when two or more substituents are present, they are the same as or different from one another, and the number may range from 1 to 4. The number of substituents range preferably from 1 to 3.

When Ring A and/or Ring B have a nitrogen atom, they may optionally form a quaternary ammonium salt, for example, they may optionally form salts with anion, for example, a halogen ion (e.g. $Cl^-$, $Br^-$, $I^-$ etc.), a sulfate ion, a hydroxyl ion, etc.

As preferable ones when Ring A is a homocyclic ring consisting of carbon atoms (hereinafter ......... stands for single or double bond), use is made of groups, among others, represented by the formula:

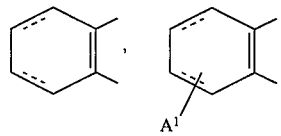

wherein $A^1$ stands for a halogen atom such as fluorine, chlorine, etc., an optionally halogenated $C_{1-4}$ alkyl group such as methyl, ethyl, isopropyl, trifluoromethyl, etc. or an optionally halogenated $C_{1-4}$ alkoxy group such as methoxy, trifluoromethoxy, ethoxy, etc., or the formula:

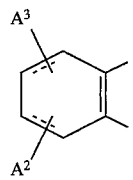

wherein $A^2$ and $A^3$ independently stand for a halogen atom such as fluorine, chlorine, etc., an optionally halogenated $C_{1-4}$ alkyl group such as methyl, ethyl, isopropyl, trifluoromethyl, etc. or an optionally halogenated $C_{1-4}$ alkoxy group such as methoxy, trifluoromethoxy, ethoxy, etc.

As more preferable examples, use is made of, among others, a benzene ring represented by the formula:

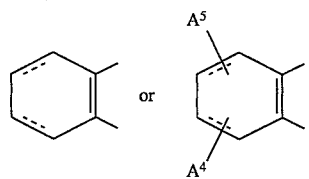

wherein $A^4$ and $A^5$ independently stand for a halogen atom such as fluorine, chlorine, etc. or an optionally halogenated $C_{1-4}$ alkyl group such as methyl, trifluoromethyl, ethyl, isopropyl, etc.

And, an optionally substituted benzene ring, for example, as follows

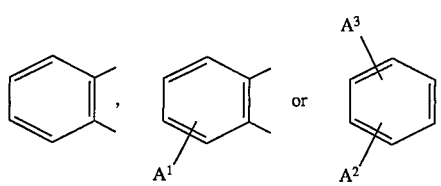

especially,

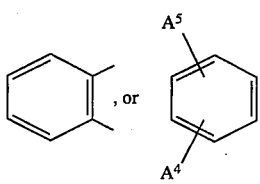

wherein each symbol is of the same meaning as defined above are conventionally employed.

Among those represented by the above formulae, especially preferable ones are, among others:

(1) $A^1$ is a halogen atom (e.g. fluorine, chlorine, etc.) or an optionally halogenated $C_{1-4}$ alkyl group (e.g. methyl, trifluoromethyl, ethyl, isopropyl, etc.), (2) $A^2$ and $A^3$ are, independently, an optionally halogenated $C_{1-4}$ alkyl group (e.g. methyl, trifluoromethyl, ethyl, isopropyl, etc.) or an optionally halogenated $C_{1-4}$ alkoxy group (e.g. methoxy, trifluoromethoxy, ethoxy, etc.), (3) $A^4$ and $A^5$ are, independently, a $C_{1-4}$ alkyl group (e.g. methyl, ethyl, isopropyl, etc.), (4) $A^1$ is a halogen atom (e.g. fluorine, chlorine, etc.), (5) $A^2$ and $A^3$ are, independently, a $C_{1-4}$ alkoxy group (e.g. methoxy, ethoxy, etc.).

Examples of preferable ones of an aromatic or non-aromatic heterocyclic ring represented by Ring A include a 5- or 6-membered aromatic or non-aromatic heterocyclic ring such as a pyridine, pyrazine, thiophene, tetrahydropyridine, pyrrole and thiazole ring. As concrete examples, the following are conventionally used:

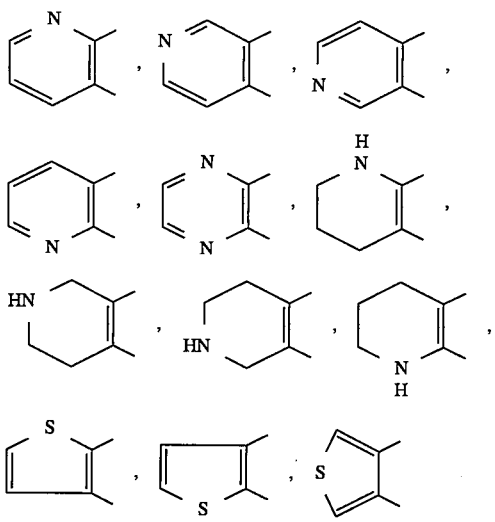

and so on. Further, among others, the following are also preferable:

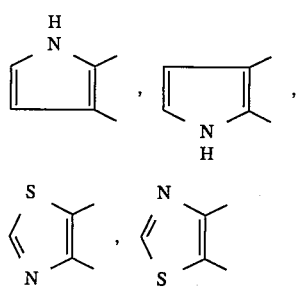

and so on.

As preferable ones of optionally substituted aromatic or non-aromatic heterocyclic rings, mention is made of a pyridine, pyrazine, thiophene, tetrahydropyridine, pyrrole, and thiazole ring, etc. which optionally have one or two substituents selected from an oxo group, an optionally substituted alkyl group (having the same meaning as defined for the substituents which the Ring A and Ring B may have), a $C_{6-10}$ aryl group (e.g. phenyl, etc.) and a halogen atom (e.g. fluorine, chlorine, bromine, etc.). More concretely, those of the following formulae, among others, are preferable:

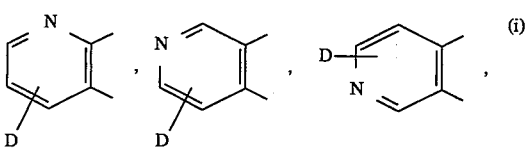 (i)

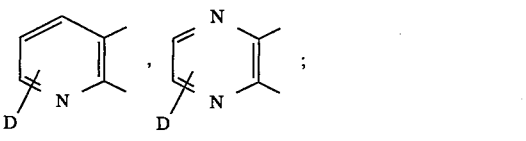

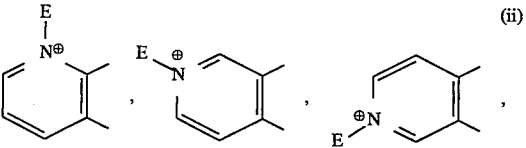 (ii)

 (iii)

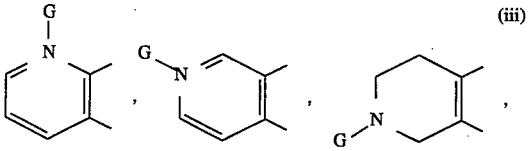

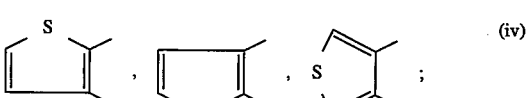 (iv)

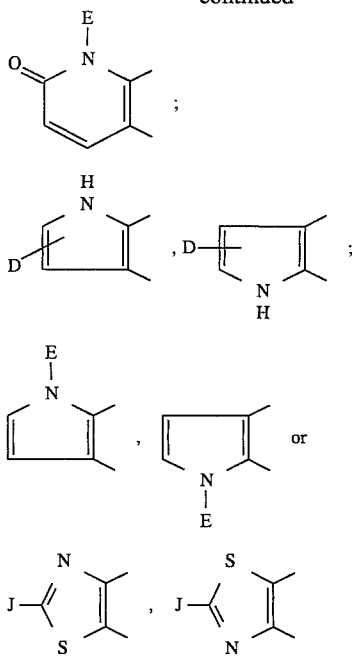

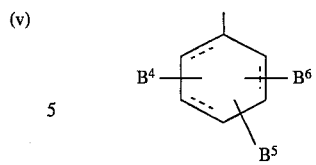

wherein B⁴, B⁵ and B⁶ independently stand for a halogen atom such as fluorine, chlorine, etc., an optionally halogenated $C_{1-4}$ alkyl group such as methyl, trifluoromethyl, ethyl, isopropyl, etc., or an optionally halogenated $C_{1-4}$ alkoxy group such as trifluoromethoxy, ethoxy, etc.

More preferably, use is made of the group represented by the formula:

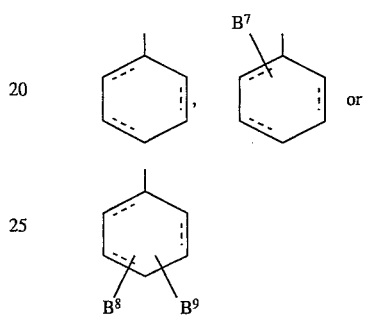

wherein D stands for a hydrogen atom, a halogen atom (e.g. fluorine, chlorine, bromine, etc.); E stands for a $C_{1-4}$ alkyl group (e.g. methyl, ethyl, propyl, isopropyl, etc.); a compound having the partial structure shown by (ii) forms a quaternary ammonium salt taken together with a halogen ion (e.g. Cl⁻, Br⁻, I⁻, etc.), a sulfate ion or a hydroxyl ion, etc.; G stands for, preferably, a hydrogen atom or a $C_{1-4}$ alkyl group (e.g. methyl, ethyl, propyl, isopropyl, etc.); J stands for a hydrogen atom, a $C_{1-4}$ alkyl group (e.g. methyl, ethyl, propyl, isopropyl, etc.) or a $C_{6-10}$ aryl group (e.g. phenyl, etc.). Ring A is more preferably a pyridine ring.

As a preferable homocyclic ring when Ring B consists of carbon atoms, (hereinafter, ......... shows single or double bond), use is made of such groups as represented by, for example, the formula:

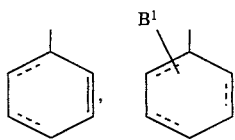

wherein B¹ stands for a halogen atom such as fluorine, chlorine, etc., an optionally halogenated $C_{1-4}$ alkyl group such as methyl, trifluoromethyl, ethyl, isopropyl, etc., or an optionally halogenated $C_{1-4}$ alkoxy group such as methoxy, trifluoromethoxy, ethoxy, etc., the formula:

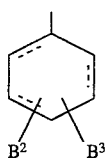

wherein B² and B³ independently stand for a halogen atom such as fluorine, chlorine, etc., an optionally halogenated $C_{1-4}$ alkyl group such as methyl, trifluoromethyl, ethyl, isopropyl, etc. or an optionally halogenated $C_{1-4}$ alkoxy group such as methoxy, trifluoromethoxy, ethoxy, etc. or the formula:

wherein B⁷, B⁸ and B⁹ independently stand for a halogen such as fluorine, chlorine, etc., an optionally halogenated $C_{1-4}$ alkyl group such as methyl, trifluoromethyl, ethyl, isopropyl, etc., or a $C_{1-4}$ alkoxy group such as methoxy, trifluoromethoxy, ethoxy, etc., etc.

Especially, a group represented by the formula:

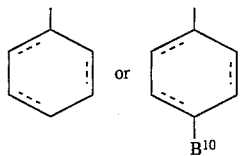

wherein B¹⁰ stands for a halogen atom such as fluorine, chlorine, etc., a $C_{1-4}$ alkyl group such as methyl, trifluoromethyl, ethyl, etc. or a $C_{1-4}$ alkoxy group such as methoxy, trifluoromethoxy, ethoxy, etc. is conventionally used.

And, it is also preferable when Ring B is an optionally substituted benzene ring, for example, groups represented by formulae:

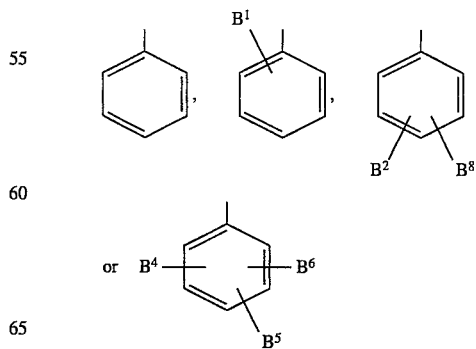

further preferably, groups represented by formulae:

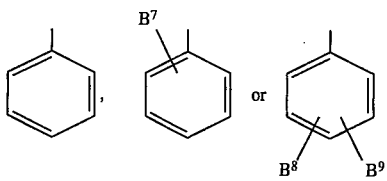

especially, groups represented by formulae:

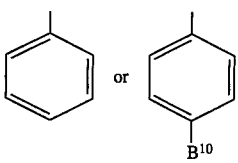

wherein all symbols are of the same meanings as defined above.

Among the substituents in the above-mentioned formulae, especially preferable ones include:

(1) $B^1$, $B^2$, $B^3$, $B^4$, $B^5$ and $B^6$ independently stand for a halogen atom (e.g. fluorine, chlorine, etc.) or an optionally halogenated $C_{1-4}$ alkyl group (e.g. methyl, trifluoromethyl, ethyl, isopropyl, etc.), (2) $B^1$, $B^2$, $B^3$, $B^4$, $B^5$ and $B^6$ independently stand for an optionally halogenated $C_{1-4}$ alkoxy group (e.g. methoxy, trifluoromethoxy, ethoxy, etc.), (3) $B^7$, $B^8$ and $B^9$ stand for a halogen atom (e.g. fluorine, chlorine, etc.), (4) $B^{10}$ stands for a fluorine atom, and (5) $B^{10}$ stands for a $C_{1-4}$ alkyl group (e.g. methyl, etc.). More preferable ones include:

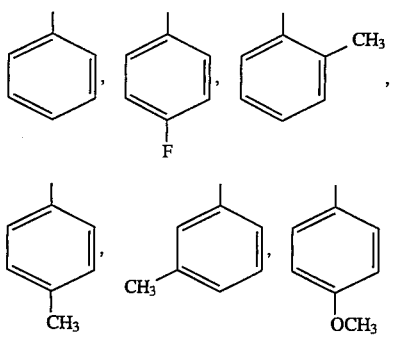

and so on.

As a preferable optionally substituted aromatic or non-aromatic heterocyclic rings represented by Ring B, mention is made of, for example, a 5- or 6-membered aromatic or non-aromatic heterocyclic ring. These rings may have substituents exemplified as preferable ones which the above-mentioned Ring A.

As especially preferable ones, for example the substituents represented by formulae:

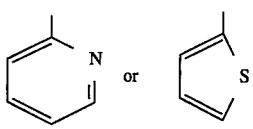

are conventionally used.

When Ring A and/or Ring B are/is a heterocyclic ring(s), an unsubstituted heterocyclic ring is also preferable.

In the above-mentioned formulae, Ring C stands for an optionally substituted benzene ring. The benzene ring may have the same or different 1 to 5 substituents, preferably 1 to 3. And those rings have substituents at optional positions. Examples of such substituents include an optionally halogenated $C_{1-4}$ alkyl group (e.g. methyl, chloromethyl, difluoromethyl, trichloromethyl, trifluoromethyl, ethyl, 2-bromoethyl, 2,2,2-trifluoroethyl, propyl, isopropyl, 3,3,3-trifluoropropyl, butyl etc.), a $C_{1-4}$ alkyl group substituted by an amino group (e.g. aminomethyl, 2-aminoethyl, etc.), a $C_{1-4}$ alkyl group substituted by a mono- or di-$C_{1-4}$ alkylamino group (e.g. methylaminomethyl, dimethylaminometyl, 2-methylaminoethyl, 2-dimethylaminoethyl, etc.), a $C_{1-4}$ alkyl group substituted by a carboxyl group (e.g. carboxymethyl, carboxyethyl, etc.), a $C_{1-4}$ alkyl group substituted by a $C_{1-4}$ alkoxycarbonyl group (e.g. methoxycarbonylethyl, ethoxycarbonylethyl, etc.), a $C_{1-4}$ alkyl group substituted by a hydroxyl group (e.g. hydroxymethyl, hydroxyethyl, etc.), a $C_{1-4}$ alkyl group substituted by a $C_{1-4}$ alkoxycarbonyl group (e.g. methoxymethyl, methoxyethyl, ethoxyethyl, etc,), a $C_{3-6}$ cycloalkyl group (e.g. cyclopropyl, cyclobutyl, cyclopentyl, cyclohexyl, etc.), a halogen atom (e.g. fluorine, chlorine, bromine, iodine, etc.), a nitro group, a cyano group, a hydroxyl group, an optionally halogenated $C_{1-4}$ alkoxy group (e.g. methoxy, difluoromethoxy, trifluoromethoxy, ethoxy, 2,2,2-trifluoroethoxy, propoxy, butoxy, isopropyloxy, etc.), an optionally halogenated $C_{1-4}$ alkylthio group (e.g. methylthio, difluoromethylthio, trifluoromethylthio, ethylthio, propylthio, isopropylthio, butylthio, etc.), an amino group, a mono- or di-$C_{1-4}$ alkylamino group (e.g. methylamino, ethylamino, propylamino, dimethylamino, diethylamino, etc.), a cyclic amino group (e.g. a 5- to 9-membered cyclic amino group optionally containing 1 to 3 hetero-atoms such as an oxygen atom and a sulfur atom, besides a nitrogen atom, specifically, for example, pyrrolidino, piperidino, morpholino, etc.), a $C_{1-4}$ alkyl-carbonylamino group (e.g. acetylamino, propionylamino, butyrylamino, etc.), an aminocarbonyloxy group, a mono- or di-$C_{1-4}$ alkylaminocarbonyloxy group (e.g. methylaminocarbonyloxy, ethylaminocarbonyloxy, dimethylaminocarbonyloxy, diethylaminocarbonyloxy, etc.), a $C_{1-4}$ alkylsulfonylamino group (e.g. methylsulfonylamino, ethylsulfonylamino, propylsulfonylamino, etc.), a $C_{1-4}$ alkoxy-carbonyl group (e.g. methoxycarbonyl, ethoxycarbonyl, propoxycarbonyl, isobutoxycarbonyl, etc.), a benzyloxycarbonyl group, a carboxyl group, a $C_{1-6}$ alkyl-carbonyl group (e.g. methylcarbonyl, ethylcarbonyl, butylcarbonyl, etc.), a $C_{3-6}$ cycloalkyl-carbonyl group (e.g. cyclohexylcarbonyl, etc.), a carbamoyl group, a mono- or di-$C_{1-4}$ alkylcarbamoyl group (e.g. methylcarbamoyl, ethylcarbamoyl, propylcarbamoyl, butylcarbamoyl, diethylcarbamoyl, dibutylcarbamoyl, etc.), a $C_{1-6}$ alkylsulfonyl group (e.g. methylsulfonyl, ethylsulfonyl, propylsulfonyl, etc.).

Further, there is also a case that Ring C is substituted with, among others, a 5- or 6-membered aromatic mono- heterocyclic group (e.g. furyl, thienyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.). The 5- or 6-membered aromatic mono- heterocyclic group may be substituted by, for example, one to three optionally halogenated $C_{1-4}$ alkyl groups (e.g. methyl, chloromethyl, difluoromethyl, trichloromethyl, trifluoromethyl, ethyl, isopropyl, etc.).

As preferable substituents on Ring C, mention is made of an optionally halogenated $C_{1-4}$ alkyl group (e.g. methyl, chloromethyl, difluoromethyl, trichloromethyl, trifluoromethyl, ethyl, 2-bromoethyl, 2,2,2-trifluoroethyl, propyl, isopropyl, 3,3,3-trifluoropropyl, etc.), a halogen atom (e.g. fluorine, chlorine, bromine, etc,), a nitro group, a hydroxyl group, an optionally halogenated $C_{1-4}$ alkoxy group (e.g. methoxy, difluoromethoxy, trifluoromethoxy, ethoxy, 2,2,2-trifluoroethoxy, propoxy, etc.), an amino group, a $C_{1-4}$ alkyl group substituted by a mono- or di-$C_{1-4}$ alkylamino group (e.g. methylaminomethyl, dimethylaminomethyl, etc.), a mono- or di-$C_{1-4}$ alkylamino group (e.g. methylamino, ethylamino, dimethylamino, diethylamino, etc.), a $C_{1-4}$-alkoxycarbonyl group (e.g. methoxycarbonyl, ethoxycarbonyl, etc.), a carboxyl group and a carbamoyl group, etc., especially, an optionally halogenated $C_{1-4}$ alkyl group (e.g. methyl, chloromethyl, difluoromethyl, trichloromethyl, trifluoromethyl, ethyl, 2-bromoethyl, propyl, isopropyl etc.), a halogen atom (e.g. fluorine, chlorine, bromine, etc.) and an optionally halogenated $C_{1-4}$ alkoxy group (e.g. methoxy, trifluoromethoxy, ethoxy, propoxy, etc.) are conventionally used. The number of these substituents ranges preferably from 1 to 3.

As more preferable Ring C, use is made of a benzene ring optionally substituted by 1 to 3 substituents selected from the group consisting of, for example, a halogen atom (e.g. chlorine, fluorine, bromine, etc.), an optionally halogenated $C_{1-4}$ alkyl group (e.g. methyl, trifluoromethyl, ethyl, isopropyl, etc.), an optionally halogenated $C_{1-4}$ alkoxy group (e.g. methoxy, trifluoromethoxy, ethoxy, etc.), a di-$C_{1-4}$ alkylamino group (e.g. dimethylamino, etc.), a $C_{1-3}$ acyloxy group (e.g. acetoxy, etc.) and a hydroxyl group. More concretely, use is made of an optionally substituted benzene ring represented by, for example, a formula:

(C-1)

wherein $C^1$, $C^2$ and $C^3$ independently stand for a hydrogen atom, a halogen atom (e.g. fluorine, chlorine, bromine, etc.), an optionally halogenated $C_{1-4}$ alkyl group (e.g. methyl, trifluoromethyl, ethyl, isopropyl, t-butyl, etc.), an optionally halogenated $C_{1-4}$ alkoxy group (e.g. methoxy, trifluoromethoxy, ethoxy, propoxy, etc.), a mono- or di-$C_{1-4}$ alkylamino group (e.g. methylamino, ethylamino, dimethylamino, diethylamino, etc.), a $C_{1-3}$ acyloxy group (e.g. acetoxy, etc.) or a hydroxyl group, or the formula:

(C-2)

wherein $C^4$ and $C^5$ independently stand for a hydrogen atom, a halogen atom (e.g. fluorine, chlorine, bromine, etc,), an optionally halogenated $C_{1-4}$ alkyl group (e.g. methyl, trifluoromethyl, ethyl, isopropyl, t-butyl, etc.) or an optionally halogenated $C_{1-4}$ alkoxy group (e.g. methoxy, trifluoromethoxy, ethoxy, propoxy, etc.). More preferably, use is made of benzene rings, for example, those in the above-mentioned formulae (C-1), (C-2), (1) $C^1$, $C^2$ and $C^3$ independently stand for a halogen atom, an optionally halogenated $C_{1-4}$ alkyl group or an optionally halogenated $C_{1-4}$ alkoxy groups, (2) $C^1$, $C^2$ and $C^3$ independently stand for a halogen atom or an optionally halogenated $C_{1-4}$ alkyl group, (3) $C^1$, $C^2$ and $C^3$ independently stand for a halogen atom, (4) $C^1$, $C^2$ and $C^3$ independently stand for an optionally halogenated $C_{1-4}$ alkyl group, (5) $C^1$, $C^2$ and $C^3$ independently stand for an optionally halogenated $C_{1-4}$ alkoxyl group, (6) $C^4$ and $C^6$ independently stand for a halogen atom, (7) $C^4$ and $C^5$ independently stand for an optionally halogenated $C_{1-4}$ alkyl group, or (8) $C^4$ and $C^5$ independently stand for an optionally halogenated $C_{1-4}$ alkoxy group.

In (1)–(8), "optionally halogenated $C_{1-4}$ alkyl group" is exemplified by methyl, trifluoromethyl, ethyl, propyl, isopropyl, etc.; "optionally halogenated $C_{1-4}$ alkoxy group" is exemplified by methoxy, trifluoromethoxy, ethoxy, propoxy, etc.; and "halogen atoms" are exemplified by fluorine, chlorine, bromine, etc.

As more preferable Ring C, use is made of a benzene ring, for example, that in the above-mentioned formulae (C-1) and (C-2), (a) $C^1$, $C^2$ and $C^3$ simultaneously stand for a fluorine, methyl, isopropyl or methoxy group, (b) Either one of $C^4$ and $C^5$ stands for a hydrogen atom, and the other stands for a methoxy group, (c) $C^1$, $C^2$ and $C^3$ simultaneously stand for a fluorine, (d) $C^4$ and $C^5$ simultaneously stand for an isopropyl, or (e) $C^4$ and $C^5$ stand for a trifluoromethyl group.

As preferable examples of Ring A and Ring B, mention is made of those in which either one of Ring A and Ring B is a 5- or 6-membered heterocyclic ring containing one or two hetero-atoms selected from nitrogen atom and sulfur atom in addition to carbon atoms (e.g. pyridine, pyrazine, thiophene, tetrahydropyridine, piperidine, piperazine, etc.) which may be substituted by a $C_{1-4}$ alkyl group (e.g. methyl, ethyl, isopropyl, etc.), and the other is a benzene ring optionally substituted by one to three substituents selected from the group consisting of a halogen atom (e.g. fluorine, chlorine, bromine, etc.), an optionally halogenated $C_{1-4}$ alkyl group (e.g. methyl, trifluoromethyl, ethyl, propyl, isopropyl, etc.) and an optionally halogenated $C_{1-4}$ alkoxy group (e.g. methoxy, trifluoromethoxy, ethoxy, propoxy, isopropoxy, etc.).

As more preferable examples of Ring A and Ring B, mention is made of those in which either one of Ring A and Ring B is a 5- or 6-membered aromatic heterocyclic ring containing one or two hetero-atoms selected from a nitrogen and a sulfur atom in addition to carbon atoms, and the other is a benzene ring optionally substituted by one to three substituents selected from the group consisting of a halogen atom (e.g. fluorine, chlorine, bromine, etc.), an optionally halogenated $C_{1-4}$ alkyl group (e.g. methyl, trifluoromethyl, ethyl, propyl, isopropyl, etc.) and an optionally halogenated $C_{1-4}$ alkoxy group (e.g. methoxy, trifluoromethoxy, ethoxy, propoxy, isopropoxy, etc.).

In the above-mentioned formulae, either one of X and Y is —$NR^1$— ($R^1$ stands for a hydrogen atom or an optionally substituted hydrocarbon residue) or —O—, and the other is —CO— or —CS—; or either one of them is —N= and the other is =CO— ($R^2$ stands for a hydrogen atom, a halogen atom, an optionally substituted hydrocarbon residue, an optionally substituted amino group or an optionally substituted hydroxyl group). Preferably, as —X—Y—, mention is made of —$NR^{1a}$—CO—, —CO—$NR^{1a}$— ($R^{1a}$ stands for a hydrogen atom or a $C_{1-6}$ alkyl group such as methyl, ethyl, propyl, isopropyl, butyl, isobutyl, secbutyl, tert-butyl, etc.), —O—CO—, —CO—O— or —N=C($R^{2a}$)— ($R^{2a}$ stands for a hydrogen atom or a $C_{1-6}$ alkyl group such as methyl, ethyl, propyl, isopropyl, butyl, isobutyl, sec-butyl, tert-butyl, etc.), more preferably —CO—$NR^{1a}$—, —$NR^{1a}$—CO— ($R^{1a}$ is of the same meaning as defined above), —N=C ($R^{2a}$)— ($R^{2a}$ is of the same meaning as defined above). Especially, —CO—$NR^{1a}$— ($R^{1a}$ is of the same meaning as defined above) is preferable.

As examples of the above-mentioned "halogen atom", use is made of, for example, fluorine, chlorine, bromine, iodine, etc., preferably, for example, fluorine, chlorine, etc. are conventionally used.

As examples of the above-mentioned "hydrocarbon residue (or group)", use is made of a group resulting from elimination of a hydrogen atom from a carbon atom in a hydrocarbon.

The "hydrocarbon residue (or group)", include an alkyl group, an alkenyl group, an alkynyl group, a cycloalkyl group, a cycloalkyl-alkyl group and an aryl group, etc., preferably, an alkyl group, a cycloalkyl group and an aryl group, especially an alkyl group are conventionally used.

As the "alkyl group", use is made of a straight-chain or branched $C_{1-6}$ alkyl group, preferably, a straight-chain or branched $C_{1-4}$ alkyl group such as methyl, ethyl, propyl, isopropyl, butyl, isobutyl, sec-butyl, tert-butyl, etc.

As the "alkenyl group", use is made of a $C_{2-6}$ alkenyl group such as ethenyl, propenyl, isopropenyl, butenyl, isobutenyl, sec-butenyl, etc., preferably a $C_{2-4}$ alkenyl group such as ethenyl, propenyl, isopropenyl, etc.

As the "alkynyl group", use is made of a $C_{2-6}$ alkenyl group such as ethynyl, propynyl, isopropynyl, butynyl, isobutynyl, sec-butynyl, etc., preferably a $C_{2-4}$ alkynyl group such as ethynyl, propynyl, isopropynyl, etc.

As the "cycloalkyl group", use is made of a $C_{3-8}$ cycloalkyl group such as cyclopropyl, cyclobutyl, cyclopentyl, cyclohexyl, etc., preferably, a $C_{3-6}$ cycloalkyl group such as cyclopropyl, cyclobutyl, etc.

As the "cycloalkyl-alkyl group", use is made of, a $C_{3-6}$ cycloalkyl-$C_{1-4}$ alkyl group such as cyclopropylmethyl, cyclopropylethyl, etc.

As the "aryl group", use is made of a $C_{6-14}$ aryl group such as phenyl, 1-naphthyl, 2-naphthyl, anthryl, phenathryl, etc., preferably, a $C_{6-10}$ aryl group such as phenyl, 1-naphthyl, 2-naphthyl, etc., especially phenyl is conventionally used.

As substituents which the "hydrocarbon residue (or group)" may have, use is made of one to five, preferably one or more (preferably 1 to 3) of substituents selected from the group consisting of, for example, a halogen atom (e.g. fluorine, chlorine, bromine, iodine, etc.), a nitro group, a cyano group, a hydroxyl group, a $C_{1-4}$ alkoxy group (e.g. methoxy, ethoxy, propoxy, butoxy, isopropoxy, etc.), a $C_{1-4}$ alkylthio group (e.g. methylthio, ethylthio, propylthio, etc.), an amino group, a mono-, di- or tri-$C_{1-4}$ alkylamino group (e.g. methylamino, ethylamino, propylamino, dimethylamino, diethylamino, triethylamino, etc.), a cyclic amino group (e.g. a 5-to 9-membered cyclic amino group optionally containing, besides a nitrogen atom, 1 to 3 hetero-atoms such as an oxygen atom, a sulfur atom, etc., practically, for example, pyrrolidino, piperidino, morpholino, etc.), a $C_{1-4}$ alkyl-carbonylamino group (e.g. acetylamino, propionylamino, butyrylamino, etc.), a $C_{1-4}$ alkylsulfonylamino group (e.g. methylsulfonylamino, ethylsulfonylamino, etc.), a $C_{1-4}$ alkoxy-carbonyl group (e.g. methoxycarbonyl, ethoxycarbonyl, propoxycarbonyl, etc.), a carboxyl group, a $C_{1-6}$ alkyl-carbonyl group (e.g. methyl carbonyl, propyl carbonyl, etc.), a carbamoyl group, a mono- or di-$C_{1-4}$ alkyl carbamoyl group (e.g. methyl carbamoyl, ethyl carbamoyl, etc.), a $C_{1-6}$ alkyl sulfonyl group (e.g. methyl sulfonyl, ethyl sulfonyl, propyl sulfonyl, etc.), a phenyl group which may be substituted by a $C_{1-3}$ alkoxy group (e.g. phenyl, methoxyphenyl, ethoxyphenyl, etc.), among others.

Preferable examples of substituents which the above-mentioned "hydrocarbon residue (or group)" may have include a hydroxyl group, a $C_{1-4}$ alkoxy group (e.g. methoxy, ethoxy, propoxy, etc.), an amino group, a mono- or di-$C_{1-4}$ alkyl amino group (e.g. methyl amino, ethyl amino, diethyl amino, etc.), a $C_{1-4}$ alkoxy-carbonyl group (e.g. methoxycarbonyl, ethoxycarbonyl, propoxycarbonyl, etc.), a carboxyl group, a carbamoyl group and a phenyl group, especially a carboxyl group, a carbamoyl group, etc. are conventionally employed.

As the above-mentioned "optionally substituted hydroxyl group", mention is made of, for example, a hydroxyl group, a $C_{1-4}$ alkoxy group (e.g. methoxy, ethoxy, propoxy, isopropoxy, butoxy, tert-butoxy, etc.), a $C_{6-10}$ aryloxy group (e.g. phenyloxy, naphthyloxy, etc.), a $C_{1-4}$ alkyl-carbonyloxy group (e.g. formyloxy, acetoxy, propionyloxy, etc.) and a $C_{6-10}$ aryl-carbonyloxy group (e.g. benzyloxy, naphthyloxy, etc.), preferably a $C_{1-4}$ alkoxy group (e.g. methoxy, ethoxy, propoxy, isopropoxy, etc.) are conventionally used.

As substituents which these groups may have, use is made of those which are substantially the same as the substituents of the above-mentioned "optionally substituted hydrocarbon residue (or group)", especially a halogen atom (e.g. fluorine, chlorine, bromine, etc.) is conventionally used.

As the above-mentioned "optionally substituted amino group", mention is made of, among others, an amino group which may be substituted by one to three substituents selected from the group consisting of (i) a $C_{1-4}$ alkyl group (e.g. methyl, ethyl, propyl, isopropyl, etc.), (ii) a $C_{1-4}$ alkyl-carbonyl group (e.g. acetyl, propionyl, butyryl, etc.), (iii) a $C_{1-4}$-alkoxy-carbonyl group (e.g. methoxycarbonyl, ethoxycarbonyl, propoxycarbonyl, etc.), (iv) a phenyl group, (v) a $C_{1-4}$ alkyl-phenyl group (e.g. 4-methylphenyl, 3-methylphenyl, 2-methylphenyl, etc.), (vi) a halogenated phenyl group (e.g. 4-chlorophenyl, 3-chlorophenyl, 2-chlorophenyl, etc.) and (vii) a $C_{1-4}$ alkoxy-phenyl group (e.g. 4-methoxyphenyl, 3-methoxyphenyl, 2-methoxyphenyl, etc.); especially an amino group, a mono- or di- $C_{1-4}$ alkylamino group (e.g. methylamino, ethylamino, propylamino, dimethylamino, diethylamino, etc.) are conventionally used.

As $R^1$, a $C_{1-4}$ alkyl group (e.g. methyl, ethyl, propyl, isopropyl, etc.) are preferable, especially a methyl group is preferable.

As $R^2$, a hydrogen atom is preferable.

In the above formulae, R stands for a hydrogen atom or an optionally substituted hydrocarbon residue.

As the "optionally substituted hydrocarbon residue (or group)" represented by R, use is made of similar ones to those described referring to $R^1$ and $R^2$. As R, a hydrogen atom or a $C_{1-6}$ alkyl group (e.g. methyl, ethyl, propyl, isopropyl, etc., especially methyl, etc.) are preferable, especially a hydrogen atom is conventionally used.

In the above-mentioned formulae, n denotes 1 or 2, and the case of 1 is most preferable.

As the compound (I) of this invention, those in which either one of Ring A and Ring B is a 5- or 6-membered heterocyclic ring containing hetero-atoms selected from a nitrogen atom and a sulfur atom in addition to carbon atoms, and the other is a benzene ring are preferable, these rings may have one or two substituents selected from the group consisting of a halogen atom and an optionally halogenated $C_{1-4}$ alkyl group;

Ring C is a benzene ring which may be substituted by one to three substituents selected from the group consisting of a halogen atom, an optionally halogenated $C_{1-4}$ alkyl group and an optionally halogenated $C_{1-4}$ alkoxy group;

R stands for a hydrogen atom or a $C_{1-6}$ alkyl group;
—X—Y— is —CO—NR$^{1a}$—, —NR$^{1a}$—CO— or —N=C (R$^{2a}$)— (R$^{1a}$ and R$^{2a}$ respectively stand for a hydrogen atom or a $C_{1-6}$ alkyl group); and n denotes 1, or their pharmaceutically acceptable salts are preferable.

As the "5- or 6-membered heterocyclic ring", mention is made of, for example, pyridine, pyrazine, pyrrole, thiophene, thiazole, tetrahydropyrazine, piperidine, etc., and, as Ring A, mention is made of, concretely, those represented by the formula:

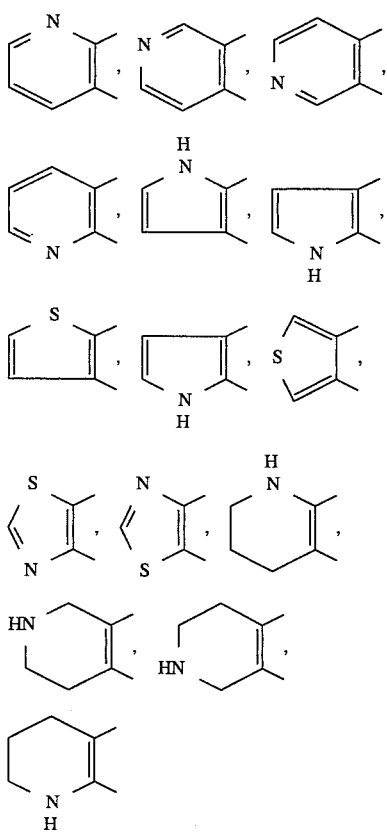

and so on.

As Ring B, mention is made of those represented by the formula:

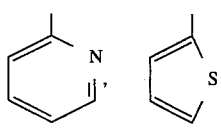

and so on.

As the "halogen atom" mention is made of, for example, fluorine, chlorine, bromine, etc. As the "optionally halogenated $C_{1-4}$ alkyl group" mention is made of, for example, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl, etc. As the "optionally halogenated $C_{1-4}$-alkoxy group", mention is made of, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc. As the "$C_{1-6}$ alkyl group", mention is made of, for example, methyl, ethyl, propyl, isopropyl, butyl, isobutyl, tert-butyl.

And, examples of preferable compounds include also those in which Ring A is a 5- or 6-membered heterocyclic ring containing one nitrogen atom or one nitrogen atom in addition to carbon atoms, represented, for example, by the formula:

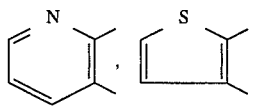

Ring B is a benzene ring optionally having 1 to 3 substituents selected from the group consisting of a halogen atom (e.g. fluorine, chlorine, etc.) and a $C_{1-4}$ alkyl group (e.g. methyl, trifluoromethyl, ethyl, propyl, isopropyl, etc.);

Ring C is a benzene ring optionally having 1 to 3 substituents selected from the group consisting of a halogen atom (having the same meaning as above), an optionally halogenated $C_{1-4}$ alkyl group (having the same meaning as above) and a $C_{1-4}$ alkoxy group (e.g. methoxy, trifluoromethoxy, ethoxy, propoxy, isopropoxy, etc.);

R is a hydrogen atom or a $C_{1-6}$ alkyl group (e.g. methyl, ethyl, propyl, isopropyl, etc.); —X—Y— is —CO—NR$^{1a}$— (R$^{1a}$ stands for a hydrogen atom or a $C_{1-6}$ alkyl group such as methyl, ethyl, propyl, isopropyl, etc.), and n denotes 1.

The compound (I) of this invention has, theoretically, isomers based on the steric configuration of the side chain amido group "—CONR—(CH$_2$)n—", and/or, rotational isomers of Ring B. While these isomers can, depending on cases, be isolated, they are included in the present invention.

When the compound (I) forms a salt and it is used as a pharmaceutical product, the salt is preferably pharmaceutically acceptable one.

Examples of such pharmaceutically acceptable salts include those with an inorganic acid, such as hydrochloride, sulfate, phosphate, diphosphate, hydrobromide and nitrate, or those with an organic acid, such as acetate, malate, maleate, fumarate, tartrate, succinate, citrate, lactate, methanesulfonate, p-toluenesulfonate, palmitate, salicylate and stearate, but not limited to these salts.

The compound (I) or salts thereof of the present invention can be produced by, for example, allowing carboxylic acid represented by the compound (II) or a salt thereof or a reactive derivative thereof to react with the compound (III) or a salt thereof (amido-bonding formation reaction). For example, in the case where the compound (III) or a salt thereof (e.g. salts with inorganic acids such as hydrochloric acid, sulfuric acid, etc. or salts with organic acids such as methanesulfonic acid, benzenesulfonic acid, toluenesulfonic acid, oxalic acid, fumaric acid, maleic acid, etc.) is allowed to react with the compound (II) or a salt thereof (e.g. salts with an alkali metal or alkaline earth metal, such as sodium, potassium, magnesium, etc., it is, in general, preferable to use an adequate condensing agent, or, the compound (II) or a salt thereof is once led to a reactive derivative thereof, which is then allowed to react with the compound (III) or a salt thereof. As the condensing agent, use is made of, for example, dicyclohexyl carbodiimide, 1-ethyl-3-(3-dimethylaminopropyl)carbodiimide, diethyl cyanophosphate, diphenyl phosphoryl azide, etc. In the case of using these condensing agent, it is usually preferable to conduct the reaction in a solvent (e.g. ethers, esters, halogenated hydrocarbons, hydrocarbons, amides, sulfoxides, etc., such as tetrahydrofuran, dioxane, dimethoxyethane, ethyl acetate, dichloromethane, 1,2-dichloroethane, benzene, toluene, N,N-dimethylformamide, dimethyl sufloxide, etc.). This reaction can be conducted in the presence of a base to promote the reaction, at temperatures ranging from about −10° C. to 100° C., preferably from about 0° C. to 60° C. The reaction time ranges usually 1 to 96 hours, preferably 1 to 72 hours. The amounts of the compound (III) or a salt thereof and a condensing agent range respectively from 1 to 5 molar equivalents, preferably from 1 to 3 molar equivalents relative to 1 mole of the compound (II) or a salt thereof. As the base, use is made of, for example, alkylamines such as triethylamine, etc., cyclic amines such as N-methyl morpholine, pyridine, etc., and its amount to be employed ranges from 1 to 5 molar equivalents, preferably from 1 to 3 molar equivalents relative to 1 mole of the compound (II) or a salt thereof.

As reactive derivatives of the compound (II), use is made of, for example, acid halides (e.g. chloride, bromide, etc.), acid anhydrides, mixed acid anhydrides, (e.g. anhydride with methyl carbonate, anhydride with ethyl carbonate, anhydride with isobutyl carbonate), active esters (e.g. ester with hydroxysuccinic acid imide, ester with 1-hydroxybenzotriazole, ester with N-hydroxy-5-norbornene-2,3-dicarboxyimide, ester with p-nitrophenol, ester with 8-oxyquinoline, etc.). The reaction between the compound (III) or a salt thereof and the compound (II) or a reactive derivative thereof is conducted usually in a solvent (for example, halogenated hydrocarbons, ethers, esters, hydrocarbons, amides, etc. such as chloroform, dichloromethane, 1,2-dichloroethane, tetrahydrofuran, dioxane, dimethoxyethane, ethyl acetate, benzene, toluene, pyridine, N,N-dimethylformamide, etc.). This reaction may be accelerated in the presence of a base. The reaction time ranges usually from 1 to 48 hours, preferably 1 to 24 hours. The amount of the compound (III) or a salt thereof ranges from 1 to 5 molar equivalents, preferably 1 to 3 molar equivalents, relative to one mole of the reactive derivative of the compound (II). As bases, use is made of, for example, alkylamines such as triethylamine, etc., cyclic amines such as N-methyl morpholine, pyridine, etc., aromatic amines such as N,N-dimethyl aniline, N,N-diethyl aniline, etc.; alkali metal carbonates such as sodium carbonate, potassium carbonate, etc., alkali metal hydrogencarbonate such as sodium hydrogencarbonate, potassium hydrogencarbonate, etc., and the amount of such bases to be used ranges from 1 to 5 molar equivalents, preferably 1 to 3 molar equivalents relative to 1 mole of the compound (II) or a reactive derivative thereof. And, in this reaction, when a water-immiscible solvent is used, the reaction can be conducted by adding water to the reaction system, i.e. in a biphasic solvent system.

And, the compound (I) or salts thereof can also be produced by the following reaction formula.

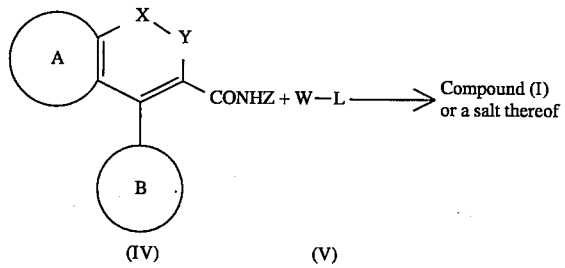

(IV)        (V)

wherein L is a leaving group, and Z and W stand for R or a group of the formula:

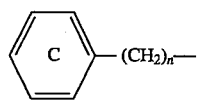

(VI)

wherein the symbols in the formula are of the same meaning as defined above, provided that, at least one of Z and W stands for a group represented by the chemical formula (VI).

As the leaving group L of the compound (V), use is made of halogen atoms (e.g. chlorine, bromine, iodine, etc.) or s substituted sulfonyloxy group (e.g. methanesulfonyloxy, p-toluenesulfonyloxy, etc.).

While the compound (IV) can be used in its free state, it may be subjected to the reaction as a salt thereof, for example, an alkali metal salt such a lithium, sodium, potassium, etc. Relative to one mole of the compound (IV) or a salt thereof, the compound W-L is subjected to the reaction in an amount of 1 to 10 moles, preferably 1 to 5 moles. Usually, the reaction is conducted in a solvent. As the solvent, use is preferably made of, for example, halogenated hydrocarbons such as dichloromethane, chloroform, etc., nitriles such as acetonitrile, etc., ethers such as dimethoxyethane, tetrahydrofuran, etc., dimethylformamide, dimethyl sulfoxide, hexamethyl phosphoramide, etc. Addition of a base serves to allow the reaction to proceed advantageously. Preferable examples of the base include sodium hydrogencarbonate, potassium hydrogencarbonate, sodium carbonate, potassium carbonate, sodium hydride, potassium hydride, sodium amide, sodium methoxide, triethylamine, diisopropyl ethyl amine, pyridine, etc. And, in this reaction, instead of using a base, the compound (IV) is converted to, for example, such an alkali metal salt, an alkaline earth metal salt, etc. as mentioned above, which may then be allowed to react with the compound W-L. While the amount of the base to be used varies depending on kinds of the compound (IV), W-L and the solvent and other reaction conditions, it usually ranges from 1 to 10 moles, preferably 1 to 5 moles, relative to 1 mole of the compound (IV). The reaction temperature ranges from −50° C. to 200° C., preferably from −20° C. to 150° C. While the reaction time varies with kinds of the compound (IV), kinds of the compound W-L or its salt or reaction temperature, it ranges from 1 to 72 hours, preferably from 1 to 24 hours.

Among the compounds (I) of this invention, a compound in which Ring A is a tetrahydropyridine ring can be produced by subjecting a compound in which Ring A is pyridine ring to reduction. While this reaction can be conducted in various methods, a preferable method comprises reduction in the presence of a metal catalyst for catalytic reduction. Examples of the catalysts to be used for this catalytic reduction include platinum catalysts such as platinum black, platinum oxide, platinum carbon, etc., palladium catalysts such as palladium black, palladium oxide, palladium barium sulfate, palladium carbon, etc., nickel catalysts such as reducing nickel, Raney nickel, etc. Preferable examples of solvents include alcohols such as methanol, ethanol, propanol, isopropanol, etc., ethers such as tetrahydrofuran, dioxane, etc., esters such as ethyl acetate, among others. The reaction temperature ranges from 0° C. to 200° C., preferably from 20° C. to 110° C. The reaction time ranges usually from 0.5 to 48 hours, preferably from 1 to 16 hours. While the reaction is conducted usually under normal atmospheric pressure, it is conducted, when necessary, under elevated pressure (3 to 10 atmospheric pressure). While the amount of the catalyst varies with its kind, it usually ranges from 0.1 to 10% (w/w) relative to the compound (I). By using substantially the same method as above, any other aromatic heterocyclic ring can be converted to a non-aromatic heterocyclic ring.

Further, a compound in which Ring A is tetrahydropyridine ring can also be produced by allowing a compound in which Ring A is pyridine ring to react with an alkylating agent represented by Q-L', wherein Q stands for an optionally substituted alkyl group and L' stands for a leaving group (as L', use is made of similar ones as L), to give a quaternary salt, then by subjecting this quaternary salt to reduction. As the alkylating agent Q-L' used for converting to the quaternary salt, use is made of halide of alkane (e.g. chloride, bromide, iodide, etc.), sulfuric acid ester or sulfonic acid ester (e.g. methanesulfonate, p-toluenesulfonate, benzenesulfonate, etc.), especially alkyl halides are preferably used. The amount of the alkylating agent to be used ranges from 1 to 100 equivalents relative to one mole of the substrate, preferably 1 to 30 equivalents. This reaction is conducted usually in a solvent. As the solvent, use is made of alcohols such as methanol, ethanol, propanol, isopropanol, etc., ethers such as tetrahydrofuran, dioxane, etc., esters such as ethyl acetate, etc., halogenated hydrogencarbonates such as dichloromethane, 1,2-dichloroethane, etc., and, depending on cases, the alkylating agent itself can be used as the solvent. The reaction temperature ranges from 10° C. to 200° C., preferably from 20° C. to 110° C. The reaction time ranges usually from 0.5 to 24 hours, preferably from 1 to 16 hours.

The reduction reaction to thus-obtained quaternary salt "tetrahydropyridine ring" can be conducted in an inert solvent by using a metal hydride, for example, sodium borohydride, lithium borohydride, zinc borohydride, sodium cyanoborohydride, lithium cyanoborohydride, aluminum lithium hydride, etc. Preferably, sodium borohydride is used. As the reaction solvent, use is made of lower alcohols such as methanol, ethanol, etc., ethers such as dioxane, tetrahydrofuran, etc. or hydrocarbons such as benzene, toluene, etc., singly or as a mixture. The reaction temperature ranges from −100° C. to 40° C., preferably from about −80° C. to 25° C. The reaction time ranges usually from 5 minutes to 10 hours, preferably from 10 minutes to 5 hours. The amount of a reducing agent ranges usually from 1 to 10 equivalents relative to a quaternary salt, preferably 1 to 2 equivalents.

While, in the reduction reaction of this quaternary salt, depending on cases, one of the object compounds of this invention, dihydropyridine ring can be produced, conversion of further reduced tetrahydropyridine ring can also be achieved by, for example, the above-mentioned catalytic reduction. And, in the case where the above-mentioned Ring A is tetrahydropyridine ring and its nitrogen atom has hydrogen atom, a compound can be formed by introducing the group Q into nitrogen atom by using an alkylating agent represented by the formula Q-L' (wherein symbols are of the same meaning as defined above). This alkylating reaction can be conducted by substantially the same method as in the case of production of the compound (I) by the above-mentioned reaction between the compound (IV) and (V).

And, by subjecting a compound, in which Ring A is a quaternary salt of pyridine ring, to oxidation, a compound in which Ring A is pyridone ring can also be produced. The oxidation reaction can be carried out by a known method "E. A. Prill et al, Organic Syntheses, Combined Book Vol. 2, p 419 (1957)" or an analogous method thereto.

When Ring B is heterocyclic ring, by subjecting this to a similar reduction reaction, conversion to a non-aromatic heterocyclic ring can be achieved.

Among the compounds (I) of this invention, a compound in which either one of X and Y is —CS— can be produced by allowing the compound whose corresponding moiety is —CO— to react with a suitable sulfide. As the sulfide employed for this reaction, use is made of, for example, phosphorus pentasulfide, Lowesson reagent, etc. This reaction is conducted usually under anhydrous conditions in a solvent such as dichloromethane, chloroform, dioxane, tetrahydrofuran, benzene, toluene, etc. The amount of the sulfide to be employed is equimoles or more, preferably 2 to 5 moles, and the reaction temperature ranges from 10° C. to 120° C. While the reaction time varies with the starting compounds or kinds of sulfides, reaction temperature or the like, it usually ranges from 1 to 8 hours.

In case where the compound (I) or a salt thereof produced by the afore-described method contains a lower ($C_{1-6}$) alkoxy group on the benzene rings in Ring A, B and C, this alkoxy group can be converted, when necessary, to hydroxyl group by allowing the alkoxy group to react, for example, boron tribromide. This reaction is conducted usually in a solvent (e.g. halogenated hydrocarbons, hydrocarbons, etc. such as dichloromethane, chloroform, carbon tetrachloride, benzene, toluene, etc.) at temperatures ranging from −20° C. to 80° C., preferably from about 0° C. to 30° C. The amount of boron tribromide ranges from about 1 to 10 molar equivalents, preferably about 1 to 5 molar equivalents, relative to one lower alkoxy group. The reaction time ranges usually from 15 minutes to 24 hours, preferably 30 minutes to 12 hours. And, in case where the compound (I) or a salt thereof produced by the afore-described method contains hydroxyl group on the benzene ring in the groups represented by Ring A, Ring B and Ring C, it can be converted to alkoxy or acyloxy group, respectively, by subjecting it, depending on necessity, alkylation or acylation. The alkylation reaction is conducted by allowing an alkylating agent, for example, halide of an optionally substituted alkane (e.g. chloride, bromide, iodide, etc.), sulfuric acid ester or sulfonic acid ester (e.g. methane sulfonate, p-toluene sulfonate, benzene sulfonate, etc.) to react therewith in a solvent (e.g. alcohols such as methanol, ethanol, propanol, etc., ethers such as dimethoxyethane, dioxane, tetrahydrofuran, etc., ketones such as acetone, etc., amides such as N,N-dimethylformamide, etc.) in the presence of a base (an organic base such as trimethylamine, triethylamine, N-methylmorpholine, pyridine, picoline, N,N-dimethyl aniline, etc. or an inorganic base such as potassium carbonate, sodium carbonate, potassium hydroxide, sodium hydroxide, etc. The reaction temperature ranges usually from −10° C. to 100° C., preferably from about 0° C. to 80° C. The amount of these alkylating agents ranges from about 1 to 5 molar equivalents, preferably 1 to 3 molar equivalents, relative to one mole of the starting phenolic derivative. The reaction time ranges usually from 15 minutes to 24 hours, preferably from 30 minutes to 12 hours.

Acylation reaction can be conducted by allowing a desired carboxylic acid or a reactive derivative thereof to react. This reaction is conducted, while varying with the kinds of acylating agents and starting phenolic derivatives, usually in a solvent (for example, hydrocarbons, ethers, esters, halogenated hydrocarbons, amides, aromatic amines, etc., such as benzene, toluene, ethyl ether, ethyl acetate, chloroform, dichloromethane, dioxane, tetrahydrofuran, N,N-dimethylformamide, pyridine, etc.), and, for accelerating the reaction, an adequate base (e.g. hydrogencarbonates such as sodium hydrogencarbonate, potassium hydrogencarbonate, etc., carbonates such as sodium carbonate, potassium carbonate, etc., acetates such as sodium acetate, tertiary amines such as triethylamine, etc., and aromatic amines such as pyridine, etc.) can be added to the reaction system. As reactive derivatives of carboxylic acid, use is made of acid anhydrides, mixed acid anhydrides, acid halides (e.g.

chloride, bromide), among others. The amount of these acylating agents ranges from 1 to 5 molar equivalents relative to one mole of the starting phenolic derivative, preferably 1 to 3 molar equivalents. The reaction temperature ranges usually from 0° C. to 150° C., preferably from about 10° C. to 100° C. The reaction time usually ranges from 15 minutes to 12 hours, preferably 30 minutes to 6 hours.

When the compound (I) thus obtained is the free compound, it can be converted to a salt, in accordance with a conventional procedure, with an inorganic acid (e.g. hydrochloric acid, sulfuric acid, hydrobromic acid, etc.), an organic acid (e.g. methanesulfonic acid, benzenesulfonic acid, toluenesulfonic acid, oxalic acid, fumaric acid, maleic acid, tartaric acid, etc.), an inorganic base (e.g. alkali metal such as sodium, potassium, alkaline earth metal such as calcium, magnesium, etc. aluminum or ammonium, etc.) or an organic base (e.g. triethylamine, triethylamine, pyridine, picoline, ethanolamine, diethanolamine, triethanolamine, dicyclohexylamine or N,N'-dibenzylethylenediamine, etc.), and, when the compound (I) is obtained in the form of a salt, it can be converted, in accordance with a conventional procedure, to the free compound or any other salt.

The compound (I) or salts thereof obtained as above can be purified and recovered by a per se known means for isolation and purification (for example, concentration, solvent-extraction, column chromatography, recrystallization, etc.)

Methods for producing the starting compound (II) or salts thereof to be employed for the production of the compound (I) or salts thereof of the present invention are described below. For example, the compound in which Ring A is thiophene ring can be produced by the method described in European laid-open Patent Application No.472116 (laid-open on Feb. 26, 1992) or an analogous methods thereto. In general, a method of synthesizing a compound represented by the general formula (II-1), in which both Ring A and Ring B are benzene ring,

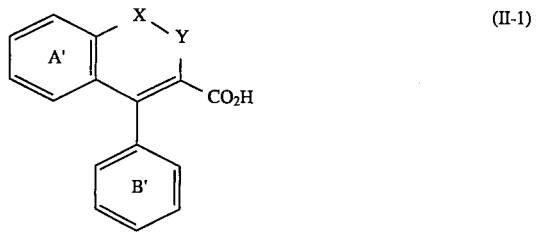

(II-1)

wherein Ring A' and Ring B' stands for optionally substituted benzene ring (the same meaning as "optionally substituted benzene ring" represented by Ring A and Ring B) can be applied to the synthesis of the compound (II) in which Ring A or Ring B contains heterocyclic ring. As the methods for synthesizing such compounds as (II-1) above, mention is made of, for example, EP laid-open 421456,(laid-open on Apr. 11, 1991), E.P. laid-open 354994 (laid-open on Feb. 21, 1990), E.P. laid-open 481383 (laid-open on Apr. 22, 1992), and PCT International laid-open No WO9112249 (laid-open on Aug. 22, 1991).

The compound (II) may, in some cases, form salts. As these salts, use is made of, for example, those with inorganic acids (e.g. hydrochloric acid, phosphoric acid, hydrobromic acid, sulfuric acid, etc.), or those with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). Further, in case where these compounds have an acid group such as —COOH, the may form salts with inorganic base (e.g. an alkali metal or an alkaline earth metal such as sodium, potassium, calcium, magnesium, etc., ammonia, among others) or organic bases (e.g. tri- $C_{1-3}$ alkylamine such as triethylamine).

In each of the above-described reactions, in case where the starting compound has an amino, carboxyl or hydroxyl group as the substituent, it can be used as previously protected with an appropriate protective group which is commonly used in, for example, peptide chemistry, and, if necessary, by removing the protective group after the reaction, the object compound can be obtained.

Examples of the protective group for such amino group include optionally substituted $C_{1-6}$ alkylcarbonyl (e.g. formyl, methylcarbonyl, ethylcarbonyl, etc.), phenylcarbonyl, $C_{1-6}$ alkyloxycarbonyl (e.g. methoxycarbonyl, ethoxycarbonyl, etc.), phenyloxycarbonyl (e.g. benzoxycarbonyl, etc.), 7°–10° C. aralkyl-carbonyl (e.g. benzyloxycarbonyl, etc.), trityl, phthaloyl and so on. As these substituents, use is made of halogen atoms (e.g. fluorine, chlorine, bromine, iodine, etc.), $C_{1-6}$ alkyl-carbonyl (e.g. methylcarbonyl, ethylcarbonyl, butylcarbonyl, etc.), and the number of the substituents ranges from 1 to 3.

Examples of the protective group of the carboxyl group include optionally substituted $C_{1-6}$ alkyl (e.g. methyl, ethyl, n-propyl, i-propyl, n-butyl, tert-butyl, etc.), phenyl, trityl, silyl and so on. As these substituents, use is made of halogen atoms (e.g. fluorine, chlorine, bromine, iodine, etc.), $C_{1-6}$ alkylcarbonyl (e.g. formyl, methylcarbonyl, ethylcarbonyl, butylcarbonyl, etc.), nitro group or the like, and the number of these substituents ranges from 1 to about 3.

As the protective groups for hydroxyl group, use is made of, for example, optionally substituted $C_{1-6}$ alkyl (e.g. methyl, ethyl, n-propyl, i-propyl, n-butyl, tert-butyl, etc.), phneyl, $C_{7-10}$ aralkyl (e.g. benzyl, etc.), $C_{1-6}$ alkylcarbonyl (e.g. formyl, methylcarbonyl, ethylcarbonyl, etc.), phenyloxycarbonyl (e.g. benzoxycarbonyl, etc.), $C_{7-10}$ aralkyl-carbonyl (e.g. benzyloxycarbonyl, etc.), pyranyl, furanyl, silyl and so on. As these substituents, use is made of halogen atoms (e.g. fluorine, chlorine, bromine, iodine, etc.), $C_{1-6}$ alkyl, phenyl, $C_{7-10}$ aralkyl, nitro group, etc., and the number of substituents ranges from 1 to about 4.

And, as the means of removing such protective groups, use is made of per se known means or analogous ones thereto. For example, treatment with an acid or a base, reduction, irradiation with ultraviolet light, and treatment with hydrazine, phenylhydrazine, sodium N-methyldithiocarbamate, tetrabutylammonium fluoride, palladium acetate or the like are used. The compound (I) or a salt produced by the above-described methods can be isolated and purified by conventional means such as recrystallization, distillation, chromatography. When the compound (I) thus obtained is the free form, it can be converted to a salt by a per se known procedure or analogous one thereto (e.g. neutralization, etc.). Conversely, when the product is a salt, it can be converted to the free form or any other salt.

The compound (I) or salts thereof produced according to the present invention have excellent tachykinin receptor antagonizing activity, especially potent antagonistic activity against substance P (hereinafter in some cases referred to as briefly SP), and are low in toxicity, thus being a medicinally useful and safe substance.

The compound (I) or salts have a inhibitory action on the tracheal plasma extravasation, for examples, as induced by capsaicin. Capsaicin is known as a substance which is a main component of the burning taste of red pepper and stimulates selectively C-fiber containing, among primary sensory nerve, SP, neuokinin A (NKN), calcitonin generelating peptide (CGRP) and as a substance for liberating the endogenous neuropeptide of them. This action of the compound (I) or salts for the inhibitory action on the vascular extravasation is considered to be based of the tachykinin receptor antagonizing activity.

SP is broadly distributed in central and peripheral nervous system and, in addition to being a primary sensory neurotransmitter, has various physiological activities such as vasodilating activity, vascular extravasation, smooth muscle contracting activity, neuronal excitatory activity, sialogogue activity, diuretic activity, immunological activity, etc. It has been known that, especially, SP released by a pain impulse at the terminal of the cornu posterius of the spinal cord transmits pain information to secondary neurons and that SP released from the peripheral nerve terminal induces an inflammatory response in the nociceptive field. Moreover, SP is suspected to be involved in Alzheimer type dementia. Review articles: [Review articles: "Physiological Reviews, 73, p.229–308(1993)", "Journal of Autonomic Pharmacology, 13, p23–93(1993)"]. Therefore, the compound (I) or salts thereof of this invention having potent SP receptor antagonizing activity are expected to be useful as safe prophylactic/therapeutic drugs for inflammation or allergic diseases (for example, atopy, dermatitis, herpes, psoriasis, asthma, bronchitis, spitting, rhintis, rheumatic arthritis, arthritis deformans, osteoporosis, disseminated sclerosis, syndesmitis, cystitis, etc.), pain, migrane, neuralgia, itch diseases, cough, and, further, diseases of central nervous system "for example, schizophrenia, Parkinson's disease, psycosomatic diseases, dementia (for example, Alzheimer's disease)", digestive diseases (for example, irritable bowel syndrome, ulcerative colitis, Cvohm disease, etc.), vomitting, disorders of micturition (for example, pollakisuria, urinary incontinence etc.), disturbances of circulation (for example, angina pectoris, hypertension, cardiac insufficiency, thrombosis, etc.) and immunopathy, etc. in mammalian animals (e.g. mouse, rat, hamster, rabbit, cat, dog, bovine, sheep, monkey, man, etc.).

In case where the compound (I) or salts thereof of this invention are used as the above-mentioned medicinal products, they are formulated with suitable pharmaceutically acceptable carriers, excipients (e.g. starch, lactose, sucrose, calcium carbonate, calcium carbonate, calcium phosphate, etc.), binders (e.g. starch, gum arabic, carboxymethyl cellulose, hydroxypropyl cellulose, crystalline cellulose, alginic acid, gelatin, polyvinyl pyrrolidone, etc.), lubricants (e.g. stearic acid, magnesium stearate, calcium stearate, talc, etc.), disintegrators (e.g. carboxymethyl cellulose calcium, talc, etc.), diluents (e.g. physiological saline, etc.), etc., which can be administered orally or otherwise in such dosage forms as powders, fine granules, granules, tablets, capsules, injections or the like by conventional procedures. While the dosage is dependent on the species of the compound (I) or pharmaceutically acceptable salts thereof, route of administration, symptom of diseases, patient's age and other background conditions, for oral administration to an adult patient of dysuria for instance, a daily dose of about 0.005 to 50 mg in terms of the compound (I) or a salt thereof per kg body weight per day, preferably about 0.05 to 10 mg, more preferably about 0.2 to 4 mg is administered in 1 to 3 divided doses.

The following are experimental data showing the pharmacological efficacy of the compound (I) or salts thereof of the present invention.

Radioligand receptor binding inhibitory activity
Binding inhibitory activity using receptor from human lymphoblast cells (IM-9)

The method of A. Margaret "Molecular Pharmacology 42, p.458 (1992)" was modified and used. The receptor was prepared from human lymphoblast cells (IM-9). IM-9 cells ($2 \times 10^5$ cells/ml) were inoculated and incubated for 3 days (one liter), which was then subjected to centrifuge for 5 minutes at 500×g to obtain cell pellets. The pellets were washed once with phosphate buffer (Flow Laboratories, CAT. No. 28-103-05), which were then crushed using Polytron.homogenizer "Kinematika, Germany" in 30 ml of 50 mM Tris-HCl buffer (pH 7.4) containing 120 mM sodium chloride, 5 mM potassium chloride, 2 μg/ml chymostatin, 40 μg/ml bacitracin, 5 μg/ml phosphoramidon, 0.5 mM phenylmethyl sulfonyl fluoride, 1 mM ethylenediamine tetra-acetic acid, which was subjected to centrifuge at 40,000×g for 20 minutes. The residue was washed twice with 30 ml of the above-mentioned buffer, which was then preserved frozen (−80° C.) as a specimen of the receptor.

The specimen was suspended in a reaction buffer (50 mM Tri-HCl buffer (pH 7.4), 0.02% bovine serum albumin, 1 mM phenylmethylsulfonyl fluoride, 2 μg/chymostatin, 40 μg/ml bacitracin, 3 mM manganese chloride) and 100 ul portion was the suspension was used in the reaction. After addition of the sample and $^{125}$I-BHSP (0.46 KBq), the reaction was allowed to proceed in 0.2 ml of reaction buffer at 25° C. for 30 minutes. The amount of nonspecific binding was determined by adding substance P at a final concentration of $2 \times 10^{-6}$M. After the reaction, using a cell harvester (290 PHD, Cambridge Technology, Inc, U.S.A.), rapid filtration was carried out through a glass filter (GF/B, Whatman, U.S.A.) to stop the reaction. After washing three times with 250 ul of 50 mM of Tris-HCl buffer (pH 7.4) containing 0.02% bovine serum albumin, the radioactivity remaining on the filter was determined with a gamma counter. Before use, the filter was immersed in 0.1% polyethyleneimine for 24 hours and air-dried. The antagonistic activity of each test drug, in terms of the concentration necessary to cause 50% inhibition ($IC_{50}$) under the above-described conditions, was expressed in nM [Table $_1$]. (Radioligand means substance P labelled with $^{125}$I.) The number of this experiment is one.

TABLE 1

| Test Compound (Example No) | $IC_{50}$ (nM) |
|---|---|
| 1 | 0.08 |
| 2 | 1.1 |
| 3 | 14 |
| 4 | 2.5 |
| 6 | 1.1 |
| 7 | 0.2 |
| 8 | 0.17 |
| 9 | 1.2 |
| 10 | 33 |
| 11 | 0.2 |
| 12 | 2.8 |
| 13 | 0.08 |
| 17 | 0.31 |
| 18 | 0.36 |
| 19 | 0.94 |
| 21 | 2.5 |
| 24 | 0.2 |
| 26 | 0.05 |
| 27 | 0.18 |
| 28 | 5 |
| 29 | 0.6 |
| 30 | 0.1 |
| 31 | 0.33 |
| 32 | 0.048 |
| 33 | 16 |
| 34 | 2.1 |
| 35 | 0.35 |

TABLE 1-continued

| Test Compound (Example No) | IC$_{50}$ (nM) |
|---|---|
| 36 | 0.34 |
| 37 | 0.62 |
| 39 | 0.28 |
| 40 | 1.8 |
| 41 | 1.1 |
| 43 | 1.0 |
| 44 | 0.24 |
| 46 | 26 |
| 47 | 0.2 |
| 49 | 1.3 |
| 50 | 0.4 |
| 51 | 2.1 |
| 53 | 0.15 |
| 54 | 0.4 |
| 55 | 0.7 |
| 56 | 0.34 |
| 57 | 3.8 |
| 58 | 0.72 |
| 59 | 0.12 |

From Table 1, it is apparent that the compound (I) or salts thereof of the present invention have excellent substance P receptor antagonizing activity.

Inhibitory effect on plasma extravasation induced by capsaicin in trachea of guinea pigs Guinea pigs (Hartley type white male guinea pigs), (n=6) were anesthetized with 35 mg/kg of pentobarbital injected intraperitoneally (i.p.), then test compounds were administered intravenously (i.v.). After 5 minutes, a mixed solution of capsaicin (150 μg/kg) and Evans' blue dye (20 mg/kg) was administered intravenously to cause reaction. Ten minutes later, test animals were sacrificed by cutting the aorta, then perfused through pulmonary artery with 50 ml of physiological saline. The trachea was excised, and its wet weight was measured. The trachea was incubated at room temperature in 1 ml of acetone-0.3% sodium sulfate (7:3) overnight and Evans' blue dye was extracted from the trachea. The extract solution was centrifuged at 2800 rpm for 5 minutes. The amount of Evans' blue dye in the supernatant was quantified by measuring absorbance at 620 mm.

Plasma extravasation was expressed in terms of the amount of Evans' blue dye (μg) relative to the weight of the trachea (g). The efficacy of the drug was evaluated by calculating the % inhibition in accordance with the following formula.

$$\% \text{ inhibition} = \left(1 - \frac{A-B}{C-B}\right) \times 100$$

A: the amount of Evan's blue dye (μg/g) in each test animal

B: the mean amount of Evan's blue dye (μg/g) of the group untreated with capsaicin.

C: the mean amount of Evan's blue dye (μg/g) of control group

TABLE 2

| Test Compound (Example No) | Dose (i.v.) mg/kg | Inhibition (%) |
|---|---|---|
| 1 | 0.03 | 76.1** |
| 7 | 0.1 | 71.9*** |
| 8 | 0.1 | 64.9** |
| 13 | 0.1 | 76.1*** |

TABLE 2-continued

| Test Compound (Example No) | Dose (i.v.) mg/kg | Inhibition (%) |
|---|---|---|
| 17 | 0.1 | 51.5** |
| 26 | 0.03 | 46.2* |
| 27 | 0.1 | 74.0*** |
| 36 | 0.03 | 54.3** |
| 39 | 0.1 | 67.9*** |
| 41 | 0.1 | 46.9* |
| 49 | 0.1 | 66.7** |
| 50 | 0.1 | 52.2** |
| 53 | 0.1 | 59.9*** |
| 54 | 0.1 | 48.3*** |
| 56 | 0.03 | 58.1** |
| 57 | 0.1 | 51.4** |
| 58 | 0.1 | 35.2* |
| 59 | 0.03 | 55.0** |

Dunnett's test: *$p < 0.05$, $p < 0.01$, *$p < 0.001$

From Table 2, it is apparent that the compound (I) or salts thereof of the present invention have excellent inhibitory action on the plasma extravasation induced by capsaicin.

The present invention will be explained further in detail by the following Reference Examples and Examples, but these are mere examples and do not limit the present invention whatsoever, and they can be modified within the range which does not deviate the scope of the present invention.

Elution in the column chromatography in Reference Examples and Examples was conducted under observation by means of TLC (Thin Layer Chromatography). In the TLC observation, 60F$_{254}$ manufactured by Merck as the TLC plate, the solvent employed in the column chromatography as the developing eluent, and uv-detector in the detection were employed, respectively. As silica-gel for the column chromatography, the silica-gel 60 (70-230 mesh) manufactured by Merck was employed. "Room temperature" means usually temperatures ranging from about 10° C. to 35° C.

For drying the extract solution, sodium sulfate or magnesium sulfate was employed.

In Examples and Reference Examples, abbreviations mean as follows.

NMR: Nuclear magnetic resonance spectrum
EI-MS: Electron-bombardment mass spectrum
SI-MS: Secondary electron ion mass spectrum
DMF: dimethylformamide, THF: tetrahydrofuran, DMSO: dimethyl sulfoxide, Hz: herz, J: coupling constant, m: multiplet, q: quartet, t: triplet, d: doublet, s: singlet, b: broad, like: approximate

EXAMPLE 1

N-[3,5-Bis(trifluoromethyl)benzyl]-5-(4-fluorophenyl)-7,8-dihydro-N, 7-dimethyl-8-oxo-6-pyrido[3,4-b]pyridine carboxamide To a suspension of 5-(4-fluorophenyl)-7,8-dihydro-7-methyl-8-oxo-6-pyrido[3,4-b]pyridinecarboxylic acid (Reference Example 1) (1.50 g) in benzene (70 ml) were added thionyl chloride (3.0 ml) and DMF (one drop). The mixture was heated for two hours under reflux. The solvent was distilled off, and the residue was washed with hexane, which was then suspended in THF (40 ml). This suspension was added to a solution of N-[3,5-bis(trifluoromethyl)benzyl] methylamine (1.80 g) and triethylamine (1.40 ml) in THF (40 ml). The mixture was stirred for 5 hours while heating under reflux. The solvent was distilled off. To the residue was added ethyl acetate, and the mixture was washed with water, an aqueous solution of sodium hydrogencarbonate and water, successively, which was dried, and then the solvent was distilled off to give the above-titled compound as colorless crystals (0.80 g), m.p.211°–212° C. (recrystallized from ethyl acetate-ethyl ether).

NMR(200 MHz, CDCl$_3$) ppm: 2.83(3H,s), 3.67(3H,s), 4.25(1H,d,J=14.4 Hz), 4.85(1H,d,J=14.4 Hz), 6.99(2H,t-like, J=8 Hz), 7.13(1H,m), 7.37(1H,m), 7.50–7.54(2H,m), 7.55(2H,s), 7.85(1H,s), 8.94(1H,dd,J=2.0,4.0 Hz)

Elemental Analysis for $C_{26}H_{18}N_3O_2F_7$: Calcd.: C, 58.11; H, 3.38; N, 7.82 Found: C, 58.03; H, 3.34; N, 7.72

Compounds of Examples 2 and 3 were produced by employing 5-(4-fluorophenyl)-7,8-dihydro-7-methyl-8-oxo-6-pyrido[3,4-b]pyridinecarboxylic acid and amines having respectively corresponding substituents, allowing the reaction to proceed and processing the reaction mixture in substantially the same manner as in Example 1.

EXAMPLE 2

N-[3,5-Bis(trifluoromethyl)benzyl]-5-(4-fluorophenyl)-7,8-dihydro-7-methyl-8-oxo-6-pyrido[3,4-b]pyridinecarboxamide m.p.210°–212° C. (recrystallized from methanol-dichloromethane-ethyl acetate).

NMR(200 MHz,CDCl$_3$) ppm: 3.21(3H,s), 4.55(2H,d,J= 6.2 Hz), 6.98(2H,t-like,J=8.6 Hz), 7.25–7.45(4H,m), 7.76(2H,s), 7.84(1H,s), 8.52(1H,t-like,J=5.8 Hz), 8.63(1H, dd,J=2.0,4.0 Hz)

EXAMPLE 3

5-(4-Fluorophenyl)-7,8-dihydro-N-(2-methoxybenzyl)-7-methyl-8-oxo-6-pyrido[3,4-b]pyridinecarboxamide m.p.254°–256° C. (recrystallized from methanol-dichloromethane-ethyl acetate).

NMR(200 MHz,CDCl$_3$) ppm: 3.54(3H,s), 3.77(3H,s), 4.34(2H,d,J=6.0 Hz), 6.80(2H,t-like,J=7.6 Hz), 6.86–7.00(4H,m), 7.20–7.32(3H,m), 7.37(1H,dd,J=4.2,8.4 Hz), 7.50(1H,dd,J=1.6,8.4 Hz), 8.77(1H,dd,J=1.6,4.2 Hz)

Elemental Analysis for $C_{24}H_{20}N_3O_3F.1/4H_2O$: Calcd.: C, 68.32; H, 4.90; N, 9.96 Found: C, 68.31; H, 4.84; N, 10.18

EXAMPLE 4

5-(4-Fluorophenyl)-7,8-dihydro-N-(2-methoxybenzyl)-N,7-dimethyl-8-oxo-6-pyrido[3,4-b]pyridinecarboxamide A mixture of the compound obtained in Example 3 (1.20 g), sodium hydride (60% oil) (150 mg) and DMF (50 ml) was stirred for 30 minutes at room temperature, to which was added methyl iodide (5.0 ml), followed by stirring for 4 hours at room temperature. The solvent was distilled off. To the residue was added ethyl acetate. This mixture was washed with water and dried, then the solvent was distilled off to leave the above-titled compound as colorless crystals (1.10 g), m.p.159°–150° C. (recrystallized from methanol-ethyl ether).

NMR(200 MHz,CDCl$_3$) ppm: 2.74(3H,s), 3.67(3H,s), 3.77(3H,s), 4.38(1H,d,J=14.8 Hz), 4.68(1H,d,J=14.8 Hz), 6.46(1H,dd,J=1.6,7.4 Hz), 6.78(1H,dt,J$_d$=1.2 Hz,J$_t$=7.4 Hz), 6.82(1H,d,J=8.2 Hz), 7.04–7.30(4H,m), 7.42–7.56(2H,m), 7.59(1H,dd,J=1.8,8.4 Hz), 8.92(1H,dd,J=1.6,4.2 Hz)

Elemental Analysis for $C_{25}H_{22}N_3O_3F$: Calcd.: C, 65.59; H, 5.14; N, 9.74 Found: C, 69.23; H, 5.12; N, 9.75

EXAMPLE 5

N,N-Bis[3,5-bis(trifluoromethyl)benzyl]-5-(4-fluorophenyl)-7,8-dihydro-7-methyl-8-oxo-6-pyrido[3,4-b]pyridinecarboxamide 5-(4-(Fluorophenyl)-7,8-dihydro-7-methyl-8-oxo-6-pyrido[3,4-b]pyridinecarboxamide (Reference Example 1 Method 2 Process 3) was allowed to react and process with 3,5-bis(trifluoromethyl)benzylbromide in DMF in the presence of sodium hydride to give the above-titled compound as colorless crystals, m.p.252°–254° C. (recrystallized from ethyl acetate-ethyl ether).

NMR(200 MHz,CDCl$_3$) ppm: 3.67(3H,s), 4.32(1H,d,J= 14.6 Hz), 4.37(1H,d,J=15.4 Hz), 4.67(1H,d,J=15.4 Hz), 4.75(1H,d,J=14.6 Hz), 7.03–7.28(5H,m), 7.34(2H,s), 7.41–7.67(3H,m), 7.75(2H,s), 7.91(1H,dd,J=1.8,4.2 Hz)

Elemental Analysis for $C_{34}H_{20}N_3O_2F_{13}$: Calcd.: C, 54.48; H, 2.69; N, 5.61 Found: C, 54.67, H, 2.59; N, 5.78

EXAMPLE 6

N-[3,5-Bis(trifluoromethyl)benzyl]-3-chloro-5-(4-fluorophenyl)-7,8-dihydro-N, 7-dimethyl-8-oxo-6-pyrido[3,4-b]pyridinecarboxamide The mother liquor after collecting the compound of Example 1 was combined with the washing, which was subjected to a silica-gel column chromatography [hexane-:ethyl acetate (1:2)→ ethyl acetate→ ethyl acetate:methanol (95:5)] to separate and purify. From the first fraction, the above-titled compound was obtained as colorless crystals (0.16 g), m.p.114°–115° C. (recrystallized from ethyl acetate-isopropyl ether).

NMR(200 MHz,CDCl$_3$) ppm: 2.83(3H,s), 3.65(3H,s), 4.25(1H,d,J=14.4 Hz), 4.84(1H,d,J=14.4 Hz), 7.01(2H,t-like,J=8.4 Hz), 7.12(1H,m), 7.34(1H,m), 7.47(1H,d,J=2.2 Hz), 7.55(2H,s), 7.85(1H,s), 8.82(1H,d,J=2.2 Hz)

Elemental Analysis for $C_{26}H_{17}N_3O_2ClF7.1/4isoPr_2O$: Calcd.: C, 55.29; H, 3.46; N, 7.03 Found: C, 55.47; H, 3.67; N, 7.05

EI-MS, m/z: 571, 573 (M$^+$)

From the next fraction, N-[3,5-bis(trifluoromethyl) benzyl]-5-(4-fluorophenyl)-7,8-dihydro-N, 7-dimethyl-8-oxo-6-pyrido[3,4-b]pyridinecarboxamide as colorless crystals (0.30 g). The physico-chemical constants of this compound where in agreement with those of the compound obtained in Example 1.

EXAMPLE 7

N-[3,5-Bis(trifluoromethyl)benzyl]-8-(4-fluorophenyl)-5,6-dihydro-N, 6-dimethyl-5-oxo-7-pyrido[3,4-b]pyrazine carboxamide A mixture of 8-(4-fluorophenyl)-5,6-dihydro-6-methyl-5-oxo-7-pyrido[3,4-b]pyrazinecarboxylic acid (Reference Example 2) (200 mg), THF (10 ml), oxalyl chloride (0.20 ml) and DMF (catalytic amount) was stirred for 30 minutes at room temperature. The solvent was distilled off, and the residue was dissolved in THF (10 ml). This solution was added to a solution of N-[3,5-bis(trifluoromethyl) benzyl]

methylamine (200 mg) and triethylamine (0.50 ml) in THF (10 ml), which was stirred for one hour at room temperature. The solvent was distilled off. To the residue was added ethyl acetate. The mixture was washed with water, an aqueous solution of sodium hydrogencarbonate and water, successively, which was dried, then the solvent was distilled off. The residue was subjected to a silica-gel column chromatography (ethyl acetate) to give the above-titled compound as colorless crystals (120 mg), m.p.220°–222° C. (recrystallized from ethyl acetate-ethyl ether).

NMR(200 MHz,CDCl$_3$) ppm: 2.81(3H,s), 3.68(3H,s), 4.38(1H,d,J=7.3 Hz), 4.75(1H,d,J=7.3 Hz), 6.98(2H,t-like, J=8.7 Hz), 7.25–7.40(2H,m), 7.59(2H,s), 7.86(1H,s), 8.84(1H,d,J=2.0 Hz), 8.86(1H,d,J=2.0 Hz)

Elemental Analysis for $C_{25}H_{17}N_4O_2F_7$: Calcd.: C, 55.77; H, 3.18; N, 10.41 Found: C, 55.81; H, 3.22; N, 10.33

EXAMPLE 8

N-[3,5-Bis(trifluoromethyl)benzyl]-4-(4-fluorophenyl)-1,2-dihydro-N, 2-dimethyl-1-oxo-3-pyrido[3,4-c]pyridine carboxamide Employing 4-(4-fluorophenyl)-1,2-dihydro-2-methyl-1-oxo-3-pyrido[3,4-c]pyridinecarboxylic acid (Reference Example 3) and N-[3,5-bis(trifluoromethyl)benzyl]methyl amine, reaction was allowed to proceed and the reaction mixture was processed in substantially the same manner as in Example 1 to give the above-titled compound as colorless crystals, m.p.179°–181° C. (recrystallized from ethyl acetate-isopropyl ether).

NMR(200 MHz,CDCl$_3$) ppm: 2.82(3H,s), 3.60(3H,s), 4.27(1H,d,J=14.6 Hz), 4.80(1H,d,J=14.6 Hz), 6.95–7.35(5H,m), 7.55(2H,s), 7.85(1H,s), 8.67(1H,d,J=5.8 Hz), 9.68(1H,s)

Elemental Analysis for $C_{26}H_{18}N_3O_2F_7$: Calcd.: C, 58.11; H, 3.38; N, 7.82 Found: C, 57.96; H, 3.44; N, 7.61

EXAMPLE 9

N-[3,5-Bis(trifluoromethyl)benzyl]-4-(4-fluorophenyl)-1,2-dihydro-N, 2-dimethyl-1-oxo-3-pyrido[4,3-c]pyridine carboxamide Employing 4-(4-fluorophenyl)-1,2-dihydro-2-methyl-1-oxo-3-pyrido[4,3-c]pyridine carboxylic acid (Reference Example 4) and N-[3,5-bis(trifluoromethyl)benzyl]methylamine, reaction was allowed to proceed and the reaction mixture was processed in substantially the same manner as in Example 1 to give the above-titled compound as colorless crystals, m.p.136°–138° C. (recrystallized from ethyl acetate-isopropyl ether).

NMR(200 MHz,CDCl$_3$) ppm: 2.82(3H,s), 3.61(3H,s), 4.31(1H,d,J=14.6 Hz), 4.77(1H,d,J=14.6 Hz), 6.95–7.37 (4H,m), 7.56(2H,s), 7.85(1H,s), 8.25(1H,d,J=5.4 Hz), 8.61(1H,s), 8.75(1H,d,J=5.4 Hz)

Elemental Analysis for $C_{26}H_{18}N_3O_2F_7$: Calcd.: C, 58.11; H, 3.38; N, 7.82 Found: C, 58.23; H, 3.53; N, 7.76

EXAMPLE 10

N-[3,5-Bis(trifluoromethyl)benzyl]-5,6-dihydro-N, 6-dimethyl-8-(2-methylphenyl)-5-oxo-7-pyrido[4,3-b]pyridinecarboxamide Employing 5,6-dihydro-6-methyl-8-(2-methylphenyl)-5-oxo-7-pyrido[4,3-b]pyridinecarboxylic acid (Reference Example 5) and N-[3,5-bis(trifluoromethyl)benzyl]methyl amine, reaction was allowed to proceed and the reaction mixture was process in substantially the same manner as in Example 1 to give a mixture of isomers of the above-titled compound (A:B= about 1:2) as colorless crystals, m.p.183°–185° C. (recrystallized from ethyl acetate-isopropyl ether).

EI-MS, m/z: 533 (M$^+$) Compound A [TLC, SiO$_2$ (ethyl acetate: hexane=1:1); Rf larger]

NMR(200 MHz,CDCl$_3$) ppm: 2.02(3H,s), 2.74(3H,s), 3.61(3H,s), 4.34(1H,d,J=14.4 Hz), 4.66(1H,d,J=14.4 Hz), 7.1–7.3(4H,m), 7. 43(1H,dd,J=4.6,8.0 Hz), 7.51(2H,s), 7.82(1H,s), 8.74(1H,dd,J=1.8,8.0 Hz), 8.89(1H,dd,J=1.8,4.6 Hz) Compound B [TLC, SiO$_2$ (ethyl acetate: hexane=1:1); Rf smaller]

NMR(200 MHz,CDCl$_3$) ppm: 2.11(3H,s), 2.99(3H,s), 3.59(3H,s), 4.15(1H,d,J=14.4 Hz), 4.91(1H,d,J=14.4 Hz), 6.96(2H,m), 7.18(2H,s), 7.42(1H,dd,J=4.6,8.0 Hz), 7.53(2H,s), 7.82(1H,s), 8.74(1H,dd,J=1.8,8.0 Hz), 8.86(1H, dd,J=1.8,4.6 Hz)

Crystals of this mixture (A:B= about 1:2) were heated for 30 minutes at 180°–190° C., then the mixture ratio was changed into 1:1 (NMR, TLC).

EXAMPLE 11

N-[3,5-Bis(trifluoromethyl)benzyl]-5-(chloro-2-methylphenyl)-7,8-dihydro-N, 7-dimethyl-8-oxo-6-pyrido[3,4-b]pyridinecarboxamide and its isomer Employing the compound obtained in Reference Example 6 and N-[3,5-Bis(trifluoromethyl)benzyl]methylamine, reaction was allowed to proceed in substantially the same manner as in Example 1 (amidation) then the reaction mixture was processed in substantially the same manner as in Example 1 to give the above-titled compound (Compound A:B= about 1:2 mixture) as colorless crystals. Compound A [TLC, SiO$_2$ (ethyl acetate); Rf larger]

NMR(200 MHz,CDCl$_3$) ppm: 2.07(3H,s), 3.02(3H,s), 3.65(3H,s), 4.11(1H,d,J=14.4 Hz), 4.99(1H,d,J=14.4 Hz), 6.89(1H,s-like), 7.12(2H,s-like), 7.28(1H,m), 7.48(1H,dd,J= 4.4,8.0 Hz), 7.58(2H,s), 7.82(1H,s), 8.93(1H,dd,J=1.6,4.4 Hz) EI-MS, m/z: 567,569 (M$^+$) Compound B [TLC, SiO$_2$ (ethyl acetate): Rf smaller]

NMR(200 MHz,CDCl$_3$) ppm: 2.14(3H,s), 2.98(3H,s), 3.64(3H,s), 4.21(1H,d,J=14.6 Hz), 4.91(1H,d,J=14.6 Hz), 6.88(1H,d-like), 6.99(1H,t-like), 7.26(1H,m), 7.37(1H,d,J=7 Hz), 7.47(1H,dd,J=4.2,8.0 Hz), 7.52(2H,s), 7.83(1H,s), 8.94(1H,m) EI-MS, m/z: 567, 569 (M$^+$)

EXAMPLE 12

N-[3,5-Bis(trifluoromethyl)benzyl]-N-methyl-4-(2-pyridyl)-3-quinolinecarboxamide A mixture of N-methyl-4-(2-pyridyl)-3-quinoline carboxamide (Reference Example 7) (262 mg), sodium hydride (60% oily) (50 mg) and DMF (10 ml) was stirred for 30 minutes at room temperature. The reaction mixture was cooled to 0° C., to which was added 3,5-bis(trifluoromethyl)benzylbromide (340 mg), and the mixture was stirred for 30 minutes at room temperature. The reaction mixture was poured into water, which was subjected to extraction with ethyl acetate. The extract solution was washed with water and dried, then the solvent was distilled off. The residue was subjected to a silica-gel column chromatography (ethyl acetate) to give the above-titled compound as an oily product (434 mg).

NMR(200 MHz, CDCl$_3$) ppm: 2.78(2.25H,s), 2.87(0.75H,s), 4.30–4.90(2H,m), 7.30(1H,m), 7.50–7.90(8H,m), 8.18(0.25H,d,J=8.4 Hz), 8.21(0.75H, d,J= 8.4 Hz), 8.58(0.75,d,J=4.8 Hz), 8.77(0.25H,d,J=4.8 Hz), 8.92(0.25H,s), 8.96(0.75H,s)

EXAMPLE 13

N-[3,5-Bis(trifluoromethyl)benzyl]-4-(4-fluorophenyl)-6,7-dihydro-N, 6-dimethyl-7-oxo-5-thieno[2,3-c]pyridinecarboxamide Employing 4-(4-fluorophenyl)-6,7-dihydro-6-methyl-7-oxo-5-thieno[2,3-c]pyridinecarboxylic acid (Reference Example 8) (202 mg) and N-[3,5-Bis(trifluorophenyl)benzyl]methylamine, reaction was allowed to proceed in substantially the same manner as in Example 1 (amidation), followed by purification by means of a silica-gel column chromatography (hexane-ethyl acetate=1:1) to give the above-titled compound as colorless crystals (221 mg), m.p.196°–197° C. (recrystallized from ethyl acetate-isopropyl ether).

NMR(200 MHz,CDCl$_3$) ppm: 2.73(3H,s), 3.63(3H,s), 4.37(1H,d,J=15 Hz), 4.76(1H,d,J=15 Hz), 6.85–7.10(2H,m), 6.93(1H,d,J=5.3 Hz), 7.20–7.40(2H,m), 7.57 (2H,m), 7.68(1H,d,J=5.3 Hz), 7.84(1H,s)

Elemental Analysis for C$_{25}$H$_{17}$N$_2$O$_2$SF$_7$: Calcd.: C, 55.35; H, 3.16; N, 5.16 Found: C, 55.13; H, 3.29; N, 4.97

Compounds of Examples 14 to 23 were produced by employing carboxylic acid having substituents corresponding to the respective compounds and benzylamines and allowing the reaction to proceed in substantially the same manner as in Example 1 (amidation), then by processing the reaction mixture in substantially the same manner as in Example 1.

EXAMPLE 14

4-(4-Fluorophenyl)-6,7-dihydro-N-(2-methoxybenzyl)-6-methyl-7-oxo-5-thieno[2,3-c]pyridinecarboxamide m.p.266°–268° C. (recrystallized from THF-isopropyl ether)

NMR(200 MHz,CDCl$_3$) ppm:3.60(3H,s), 3.71(3H,s), 4.32(2H,d,J=6.0 Hz), 6.45(1H,bt), 6.69–7.05(6H,m), 7.18–7.30(3H,m), 7.60(1H,d,J=5.2 Hz)

EXAMPLE 15

4-(4-Fluorophenyl)-6,7-dihydro-N-(2-methoxybenzyl)-N, 6-dimethyl-7-oxo-5-thieno[2,3-c]pyridinecarboxamide m.p.140° C. (recrystallized from ethyl acetate-isopropyl ether)

NMR(200 MHz,CDCl$_3$) ppm: 2.66(3H,s), 3.64(3H,s), 3.76(3H,s), 4.42(1H,d,J=15 Hz), 4.65(1H,d,J=15 Hz), 6.53(1H,d,J=7.6 Hz), 6.70–6.85(2H,m), 6.94(1H,d,J=5.2 Hz), 7.00–7.50(5H,m), 7.66(1H,d,J=5.2 Hz)

EXAMPLE 16

N-[3,5-Bis(trifluoromethyl)benzyl]-4-(4-fluorophenyl)-6,7-dihydro-6-methyl-7-oxo-5-thieno[2,3-c]pyridinecarboxamide m.p.154° C. (recrystallized from ethyl acetate-isopropyl ether).

NMR(200 MHz,CDCl$_3$) ppm: 3.34(3H,s), 4.47(2H,d,5.8 Hz), 6.82(1H,d,J=5.2 Hz), 6.92(2H,t-like,J=8.6 Hz), 7.25–7.35(2H,m), 7.56(1H,d,J=5.2 Hz), 7.57(1H,m), 7.61(2H,s), 7.82(1H,s)

EXAMPLE 17

N-[3,5-Bis(trifluoromethyl)benzyl]-7-(4-fluorophenyl)-4,5-dihydro-N, 5-dimethyl-4-oxo-6-thieno[3,2-c]pyridinecarboxamide m.p.188°–189° C. (recrystallized from ethyl acetate-isopropyl ether)

NMR(200 MHz,CDCl$_3$) ppm: 2.75(3H,s), 3.61(3H,s), 4.38(1H,d,J=15 Hz), 4.75(1H,d,J=15 Hz), 6.99(2H,t-like,J=8.4 Hz), 7.34(1H,d,J=5.6 Hz), 7.35–7.46(2H,m), 7.56(2H,s), 7.73(1H,d,J=5.6 Hz), 7.84(1H,s)

EXAMPLE 18

N-[3,5-Bis(trifluoromethyl)benzyl]-7-(4-fluorophenyl)-4,5-dihydro-N, 5-dimethyl-4-oxo-6-thieno[3,4-c]pyridine carboxamide m.p.130°–132° C. (recrystallized from ethyl ether-hexane)

NMR(200 MHz,CDCl$_3$) ppm: 2.78(3H,s), 3.50(3H,s), 4.37(1H,d,J=15 Hz), 4.71(1H,d,J=15 Hz), 6.90–7.15(2H,m), 7.08(1H,d,J=3.3 Hz), 7.30–7.45(2H,m), 7.55(2H,s), 7.82(1H,s), 8.44(1H,d,J=3.3 Hz)

EXAMPLE 19

N-[3,5-Bis(trifluoromethyl)benzyl]-8-(4-fluorophenyl)-5,6-dihydro-N, 6-dimethyl-5-oxo-7-pyrido[4,3-b]pyridine carboxamide m.p.149°–150° C. (recrystallized from ethyl acetate-isopropyl ether)

NMR(200 MHz,CDCl$_3$) ppm: 2.78(3H,s), 3.61(3H,s), 4.41(1H,d,J=14.6 Hz), 4.66(1H,d,J=14.6 Hz), 6.97(2H,t-like), 7.33(2H,m), 7.45(1H,dd,J=4.2,8.0 Hz), 7.59(2H,s), 7.85(1H,s), 8.75(1H,dd,J=1.6,8.0 Hz), 8.89(1H,dd,J=1.6,4.4 Hz)

EXAMPLE 20

N-[3,5-Bis(trifluoromethyl)benzyl]-5,6-dihydro-8-(2-methylphenyl)-6-methyl-5-oxo-7-pyrido[4,3-b]pyridine carboxamide m.p.192°–193° C. (recrystallized from THF-isopropyl ether)

NMR(200 MHz,CDCl$_3$) ppm: 3.64(3H,s), 4.25(1H,dd,J= 5.8,14.4 Hz), 4.39(1H,dd,J=6.2,14.4 Hz), 6.05(1H,b), 6.95–7.20(4H,m), 7.78(1H,dd,J=4.6,8.2 Hz), 7.57(2H,s), 7.80(1H,s), 8.67(1H,d,J=8.2 Hz). 8.84(1H,m)

EXAMPLE 21

N[3,5-Bis(trifluoromethyl)benzyl]-1,2-dihydro-N, 2-dimethyl-1-oxo-4-(2-thienyl)-3-isoquinolinecarboxamide m.p.142°–143° C. (recrystallized from ethyl acetate-isopropyl ether)

NMR(200 MHz,CDCl$_3$) ppm: 2.86(3H,s), 3.60(3H,s), 4.25(1H,d,J=14.2 Hz), 4.99(1H,d,J=14.2 Hz), 6.97(2H,m), 7.04(1H,m), 7.20–7.45(3H,m), 7.50–7.67(3H,m), 7.82(1H, s), 8.49(1H,m)

EXAMPLE 22

1,2-Dihydro-N-(2-methoxybenzyl)-2-methyl-1-methyl-1-oxo-4-(2-thienyl)-3-isoquinolinecarboxamide m.p.237°–238° C. (recrystallized from methanol-ethyl ether)

NMR(200 MHz,CDCl$_3$) ppm: 3.59(3H,s), 3.80(3H,s), 4.34(2H,d,J=6.0 Hz), 6.39(1H,b), 6.75–6.92(3H,m), 6.95–7.05(2H,m), 7.18–7.31(2H,m), 7.37–7.62(3H,m), 8.43(1H,m)

EXAMPLE 23

1,2-Dihydro-N-(2-methoxybenzyl)-N, 2-dimethyl-1-oxo-4-(2-thienyl)-3-isoquinolinecarboxamide m.p.173°–174° C. (recrystallized from methanol-ethyl ether)

NMR(200 MHz,CDCl$_3$) ppm: 2.79(3H,s), 3.60(3H,s), 3.80(3H,s), 4.50(1H,d,J=15.0 Hz), 4.68(1H,d,J=15.0 Hz), 6.50(1H,dd,J=1.6,7.6 Hz), 6.74–6.87(2H,m), 7.09–7.24(3H, m), 7.38–7.66(4H,m), 8.48(1H,m)

Compounds of Examples 24 and 25 were produced by employing N-methylcarboxamide derivatives having substituents corresponding to the respective compounds and 3,5-bis(trifluoromethyl)benzylbromide and by allowing the reaction (alkylation) to proceed and by processing the reaction mixture in substantially the same manner as in Example 12.

EXAMPLE 24

N[3,5-Bis(trifluoromethyl)benzyl]-4-(4-fluorophenyl)-N-methyl-5-thieno[2,3-b]pyridinecarboxamide m.p.193°–194° C. (recrystallized from ethyl acetate-hexane)

NMR(200 MHz ,CDCl$_3$) ppm: 2.58(2.4H,s), 2.86(0.6H, s), 4.20–5.10(2H,m), 7.00–7.30(3H,m), 7.38–7.49(2H,m), 7.55–7.65 (3H,m), 7.76(0.2H,s), 7.83(0.8H,s), 8.61(0.8H, s), 8.62(0.2H,s)

EXAMPLE 25

N-[3,5-Bis(trifluoromethyl)benzyl]-1,2-dihydro-N, 1-dimethyl-2-oxo-4-(2-pyridyl)-3-quinolinecarboxamide 122°–124° C. (recrystallized from ethyl ether-hexane)

NMR(200 MHz,CDCl$_3$) ppm:2.74(0.75H,s), 2.91(2.25H, s), 3.81(0.75H,s), 3.84(2.25H,s), 4.30(0.75H,d,J=15 Hz), 4.51(0.25H,d,J=16 Hz), 4.66(0.25H,d,J=16 Hz), 5.03(0.75H,d,J=15 Hz), 7.15–7.95(10H,m), 8.58(0.75H,m), 8.72(0.25H,m)

EXAMPLE 26

N-[3,5-Bis(trifluoromethyl)benzyl]-1,2,3,4,5,6-hexahydro-N, 6-dimethyl-8-(2-methylphenyl)-5-oxo-7-pyrido[4,3-b]pyridinecarboxamide The compound obtained in Example 10 (a mixture of isomers of about 1:2) (200 mg) was dissolved in methanol (200 ml). To the solution was added 10% Pd-C (50% hydrate) (100 mg), and the mixture was stirred for 8 hours at room temperature. The catalyst was filtered off. From the filtrate, the solvent was distilled off to leave the above-titled compound [a mixture of isomers (A:B= about 1:2)] as colorless crystals (125 mg). NMR(200 MHz,CDCl$_3$) signals (ppm) of each isomer are as follows: Isomer A [TLC, SiO$_2$ (ethyl acetate: methanol=10:1); Rf larger]1.85(2H,m), 2.15(3H,s), 2.62(2H,m), 2.72(3H,s), 3.14(2H,m), 3.43(3H, s), 3.80(1H,m), 4.13(1H,d,J=15 Hz), 4.82(1H,d,J=15 Hz), 6.80–7.00(2H,m), 7.03–7.53(4H,m), 7.76(1H,s) Isomer B [TLC, SiO$_2$ (ethyl acetate:methanol=10:1); Rf smaller]

1.85(2H,m), 2.19(3H,s), 2.62(2H,m), 2.92 (3H,s ), 3.14(2H,m), 3.42(3H,s), 3.64(1H,m), 4.03(1H,d,J=15 Hz), 4.93(1H,d,J=15 Hz), 6.80–7.00(2H,m), 7.03–7.53(4H,m), 7.76(1H,s)

EXAMPLE 27

N-[3,5-Bis(trifluoromethyl)benzyl]-8-(4-fluorophenyl)-1,2,3,4,5,6-hexahydro-N, 6-dimethyl-5-oxo-7-pyrido[4,3-b]pyridinecarboxamide In methanol (8 ml) was dissolved N-[3,5-bis (trifluoromethyl)benzyl]-8-(4-fluorophenyl)-5,6-dihydro-N, 6-dimethyl-5-oxo-7-pyrido[4,3-b]pyridinecarboxamide (Example 19) (50 mg). To the solution was added 10% Pd-C (50% hydrous) (40 mg). The mixture was stirred for 3 hours at room temperature under hydrogen atmosphere. The catalyst was filtered off. From the filtrate, the solvent was distilled off to give the above-titled compound as colorless crystals (35 mg).

m.p.226°–228° C. (recrystallized from ethyl acetate-isopropyl ether)

NMR(200 MHz,CDCl$_3$) ppm: 1.86(2H,m), 2.64(2H,m), 2.78(3H,s), 3.17(2H,m), 3.42(3H,s), 3.82(1H,b), 4.16(1H,d, J=14.2 Hz), 4.79(1H,d,J=14.2 Hz), 6.9–7.3(4H,m), 7.49(2H, s), 7.80(1H,s)

EXAMPLE 28

N-[3,5-Bis(trifluoromethyl)benzyl]-8-(4-fluorophenyl)-1,2,3,4,5,6-hexahydro-N, 1,6-trimethyl-5-oxo-7-pyrido[4,3-b]pyridinecarboxamide In THF (3 ml) was dissolved N-[3,5-bis(trifluoro methyl)benzyl]-8-(4-fluorophenyl)-1,2,3,4,5,6-hexahydro-N,6-dimethyl-5-oxo-7-pyrido[4,3-b]pyridinecarboxamide (Example 27)(68 mg). To the solution were added sodium hydride (60% oil) (6 mg) and iodomethane (1.5 ml). The mixture was stirred for 15 hours at room temperature. To the reaction mixture was added ethyl acetate, and the mixture was washed with water and dried, then the solvent was distilled off to give the above-titled compound as colorless crystals (39 mg), m.p.230°–232° C. (recrystallized from ethyl acetate-ethyl ether)

NMR(200 MHz,CDCl₃) ppm: 1.81(2H,m), 2.16(3H,s), 2.58(3H,s), 2.62(2H,m), 3.01(2H,m), 3.44(3H,s), 4.32(1H, d,J=14.4 Hz), 4.57(1H,d,J=14.4 Hz), 6.8–7.3(4H,m), 7.54(2H,s), 7.82(1H,s)

EXAMPLE 29

6-[N-[3,5-Bis(trifluoromethyl)benzyl]-N-methylamino carbonyl]-5-(4-fluorophenyl)-7,8-dihydro-1,7-dimethyl-8-oxopyrido[3,4-b]pyridinium iodide A mixture of N-[3,5-bis(trifluoromethyl)benzyl]-5-(4-fluorophenyl)-7,8-dihydro-N, 7-dimethyl-8-oxo-6pyrido[3,4-b]pyridinecarboxamide (Example 1) (175 mg), iodomethane (3 ml) and dioxane (3 ml) was heated for 16 hours under reflux. The solvent was distilled off to leave the above-titled compound as yellow crystals (200 mg), m.p.184°–185° C. (decomp.) (recrystallized from dioxane-ethyl acetate).

NMR(200 MHz,CDCl₃) ppm: 3.10(3H,s), 3.61(3H,s), 4.20(1H,d,J=14.2 Hz), 4.81(1H,d,J=14.2 Hz), 4.99(3H,s), 6.97(2H,m), 7.29(1H,m), 7.52(1H,m), 7.55(2H,s), 7.84(1H, s), 8.0 7(2H,m), 9.27(1H,d,J=4.4 Hz)

EXAMPLE 30

N-[3,5-Bis(trifluoromethyl)benzyl]-5-(4-fluorophenyl)-1,2,3,4,7,8-hexahydro-N,1,7-trimethyl-8-oxo-6-pyrido[3,4-b]pyridinecarboxamide To a solution of the compound (310 mg) obtained in Example 29 in methanol (15 ml) was added portionwise sodium borohydride (50 mg) at room temperature while stirring. This mixture was stirred for 15 minutes at room temperature, which was then concentrated. To the concentrate was added ethyl acetate, which was washed with water and dried, then the solvent was distilled off to leave N-[3, 5-bis(trifluoromethyl)benzyl]-5-(4-fluorophenyl)-1,2,7,8-tetrahydro-N,1,7-trimethyl-8-oxo-6-pyrido[3,4-b]pyridinecarboxamide as a pale yellow oily product [NMR (200 MHz,CDCl₃) ppm: 2.70(3H,s), 3.16(3H,s), 3.49(3H,s), 3.49(1H,m), 3.88(1H,m), 4.29(1H,d,J=14.6 Hz), 4.66(1H,d, J=14.6 Hz), 5.62(1H,m), 5.77(1H,d,J=13 Hz), 6.84–7.26(4H,m), 7.53(2H,s), 7.81(1H,s)].

This oily compound was dissolved in methanol (15 ml), to which was added 10% Pd-C (50% hydrous) (200 mg). The mixture was stirred for 18 hours at room temperature under hydrogen atmosphere. The catalyst was filtered off, and, from the filtrate, the solvent was distilled off. The residue was purified by means of a silica-gel column chromatography (ethyl acetate→ethyl acetate: methanol=4:1) to give the above-titled compound as colorless crystals (125 mg), m.p.155°–157° C. (recrystallized from ethyl acetate-isopropyl-ether).

NMR(200 MHz,CDCl₃) ppm: 1.68(2H,m), 1.74–2.32(2H,m), 2.66(3H,s), 3.04(3H,s), 3.05(2H,m), 3.48(3H,s), 4.21(1H,d,J=14.4 Hz), 4.72(1H,d,J=14.4 Hz), 6.83–7.27(4H,m), 7.51(2H,s), 7.81(1H,s)

EXAMPLE 31

3-[N-[3,5-Bis(trifluoromethyl)benzyl]-N-methylamino carbonyl]-4-(4-fluorophenyl)-1,2-dihydro-2,7-dimethyl-1-oxopyrido[3,4-c]pyridinium iodide A mixture of N-[3,5-bis(trifluoromethyl)benzyl]-4-(4-fluorophenyl)-1,2-dihydro-N, 2-dimethyl-1-oxo-3-pyrido[3,4-c]pyridinecarboxamide (Example 8) (240 mg), iodomethane (4 ml) and dioxane (4 ml) was heated for 1.5 hour under reflux. The solvent was distilled off to leave the above-titled compound as yellow crystals (303 mg), m.p.155°–158° C. (decomp.) (recrystallized from dioxane-ethyl ether).

NMR(200 MHz,CDCl₃) ppm: 2.98(3H,s), 3.61(3H,s), 4.24(1H,d,J=14.2 Hz), 4.68(3H,s), 4.78(1H,d,J=14.2 Hz), 6.9–7.6(5H,m), 7.54(2H,s), 7.85(1H,s), 8.82(1H,d,J=7 Hz), 9.72(1H,s)

EXAMPLE 32

N-[3,5-Bis(trifluoromethyl)benzyl]-4-(4-fluorophenyl)-1,2,5,6,7,8-hexahydro-N,2,7-trimethyl-1-oxo-3-pyrido[3,4-c]pyridinecarboxamide Employing 3-[N-[3,5-Bis(trifluoromethyl)benzyl]-N-methylaminocarbonyl]-4-(4-fluorophenyl)-1,2-dihydro-2,7-dimethyl-1-oxopyrido[3,4-c]pyridinium iodide (Example 31) (300 mg), substantially the same reaction (reduction) and work-up were conducted to give the above-titled compound as colorless crystals (125 mg), m.p.156°–157° C. (recrystallized from ethyl acetate-isopropyl ether).

NMR(200 MHz,CDCl₃) ppm: 1.93–2.73(4H,m), 2.48(3H,s), 2.75(3H,s), 3.24(1H,d,J=17 Hz), 3.75(1H,d,J= 17 Hz), 4.18(1H,d,J=14.3 Hz), 4.77(1H,d,J=14.3 Hz), 6.84–7.25(4H,m), 7.50(2H,s), 7.81(1H,s)

EXAMPLE 33

3-[N-[3,5-Bis(trifluoromethyl)benzyl]-N-methylamino carbonyl]-4-(4-fluorophenyl)-1,2-dihydro-2,6-dimethyl-1-oxopyrido[4,3-c]pyridinium iodide A mixture of N-[3,5-bis(trifluoromethyl)benzyl]-4-(4-fluorophenyl)-1,2-dihydro-N, 2-dimethyl-1-oxo-3-pyrido[4,3-c]pyridinecarboxamide (Example 9) (90 mg), iodomethane (1.5 ml) and dioxane (1.5 ml) was heated for 3 hours under reflux. The solvent was distilled off to give the above-titled compound as yellow crystals (105 mg), m.p.260°–262° C. (recrystallized from dioxane-ethyl ether).

NMR(200 MHz,CDCl₃+ DMSO-d₆) ppm: 2.75(3H,s), 3.46(3H,s), 4.04(1H,d,J=14 Hz), 4.34(3H,s), 4.69(1H,d,J= 14 Hz), 6.7–7.2(3H,m), 7.42(2H,s), 7.65(1H,s), 7.8(1H,m), 8.60(1H,s), 8.63(2H,s)

EXAMPLE 34

N-[3,5-Bis(trifluoromethyl)benzyl]-4-(4-fluorophenyl)-1,2,5,6,7,8-hexahydro-N,2,6-trimethyl-1-oxo-3-pyrido[4,3-c]pyridinecarboxamide Employing 3-[N-[3,5-bis(trifluoromethyl)benzyl]-N-methylaminocarbonyl]-4-(4-fluorophenyl)-1,2-dihydro-2,6-dimethyl-1-oxopyrido[4,3-c]pyridinium iodide (Example 33) (600 mg), substantially the same reaction (reduction) and work-up were conducted to give the above-titled compound as colorless crystals (300 mg), m.p.156°–158° C. (recrystallized from ethyl acetate-isopropyl ether).

NMR(200 MHz,CDCl₃) ppm: 2.97(3H,s), 2.58–2.78(5H, m), 2.78(3H,s), 3.06(1H,d,J=17 Hz), 3.50(3H,s), 4.17(1H, d,J=14.5 Hz), 4.79(1H,d,J=14.5 Hz), 6.86–7.25(4H,m), 7.50(2H,s), 7.82(1H,s)

EXAMPLE 35

N-[3,5-Bis(trifluoromethyl)benzyl]-5-(4-fluorophenyl)-1,2,7,8-tetrahydro-N,1,7-trimethyl-2,8-dioxo-6-pyrido[3,4-b]pyridinecarboxamide A mixture of 6-[N-[3,5-bis(trifluoromethyl)benzyl]-N-methylaminocarbonyl]-5-(4-fluorophenyl)-7,8-dihydro-1,7-dimethyl-8-oxopyrido[3,4-b]pyridinium iodide (Example 29) (100 mg), THF (3 ml), potassium ferricyanide (500 mg) and 1N-NaOH was stirred for 15 hours. The solvent was distilled off. To the residue was added ethyl acetate, and the mixture was washed with water and dried, then the solvent was distilled off. The residue was subjected to a silica-gel column chromatography (ethyl acetate) for separation and purification to afford the above-titled compound as colorless crystals (35 mg), m.p.210°–212° C. (recrystallized from ethyl acetate-isopropyl ether).

NMR(200 MHz,CDCl$_3$) ppm: 2.79(3H,s), 3.55(3H,s), 4.17(3H,s), 4.23(1H,d,J=14.6 Hz), 4.78(1H,d,J=14.6 Hz), 6.78(1H,d,J=9.8Hz), 6.92–7.32(4H,m), 7.08(1H,d,J=9.8 Hz), 7.53(2H,s), 7.83(1H,s)

Compounds of Examples 36 to 47 were obtained by subjecting carboxylic acids having substituents corresponding to the respective compounds and benzylamines to substantially the same reaction (amidation) and work-up as in Example 1.

EXAMPLE 36

N-[3,5-Bis(trifluoromethyl)benzyl]-7,8-dihydro-N,7-dimethyl-8-oxo-5-phenyl-6-pyrido[3,4-b]pyridinecarboxamide m.p.191°–192° C. (recrystallized from methanol-ethyl ether)

NMR(200 MHz,CDCl$_3$) ppm: 2.79(3H,s), 3.67(3H,s), 4.24(1H,d,J=14.6 Hz), 4.82(1H,d,J=14.6 Hz), 7.05–7.63(9H,m), 7.81(1H,s), 8.93(1H,m)

EXAMPLE 37

N-[3,5-Bis(trifluoromethyl)benzyl]-1,2-dihydro-N,2-dimethyl-1-oxo-4-phenyl-3-pyrido[3,4-c]pyridinecarboxamide m.p.192°–194° C. (recrystallized from ethyl acetate-isopropyl ether)

NMR(200 MHz,CDCl$_3$) ppm: 2.78(3H,s), 3.60(3H,s), 4.26(1H,d,J=14.6 Hz), 4.77(1H,d,J=14.6 Hz), 7.04(1H,d,J=5.6 Hz), 7.15–7.34(5H,m), 7.49(2H,s), 7.81(1H,s), 8.6(1H,d,J=5.6 Hz), 9.69(1H,s)

EXAMPLE 38

N[3,5-Bis(trifluoromethyl)benzyl]-5,6-dihydro-N,6-dimethyl-5-oxo-8-phenyl-7-Pyrido[4,3-b]pyridinecarboxamide m.p.127°–128° C. (recrystallized from ethyl acetate-isopropyl ether)

NMR(200 MHz,CDCl$_3$) ppm: 2.74(3H,s), 3.62(3H,s), 4.37(1H,d,J=14.6 Hz), 4.64(1H,d,J=14.6 Hz), 7.20–7.40(5H,m), 7.44(1H,dd,J=4.6,8.2 Hz), 7.53(2H,s), 7.81(1H,s), 8.76(1H,dd,J=2.0,8.2 Hz), 8.90(1H,dd,J=2.0,4.6 Hz)

EXAMPLE 39

N-[3,5-Bis(trifluoromethyl)benzyl]-4-(4-fluorophenyl)-6,7-dihydro-N,1,6-trimethyl-7-oxo-5-pyrrolo[2,3-c]pyridinecarboxamide m.p.160°–161° C. (recrystallized from ethyl ether-hexane)

NMR(200 MHz,CDCl$_3$) ppm: 2.66(3H,s), 3.57(3H,s), 4.21(3H,s), 4.45(1H,d,J=14.5 Hz), 4.67(1H,d,J=14.5 Hz), 6.05(1H,d,J=3.0 Hz), 6.96(2H,t-like,J=8.4 Hz), 7.00(1H,d,J=3.0 Hz), 7.31–7.42(2H,m), 7.58(2H,s), 7.82(1H,s)

EXAMPLE 40

N-[3,5-Bis(trifluoromethyl)benzyl]-7-(4-fluorophenyl)-4,5-dihydro-N,5-dimethyl-4-oxo-6-thiazolo[5,4-c]pyridinecarboxamide m.p.189°–190° C. (recrystallized from ethyl acetate-hexane)

NMR(200 MHz,CDCl$_3$) ppm: 2.73(3H,s), 3.66(3H,s), 4.47(1H,d,J=14.6 Hz), 4.70(1H,d,J=14.6 Hz), 7.00(2H,t-like,J=8.4 Hz), 7.37–7.47(2H,m), 7.60(2H,s), 7.86(1H,s), 9.12(1H,s)

EXAMPLE 41

N-[3,5-Bis(trifluoromethyl)benzyl]-7-(4-fluorophenyl)-4,5-dihydro-N,5-dimethyl-4-oxo-6-thiazolo[4,5-c]pyridinecarboxamide m.p.207°–210° C. (recrystallized from ethyl acetate-isopropyl-ether)

NMR(200 MHz,CDCl$_3$) ppm: 2.76(3H,s), 3.67(3H,s), 4.36(1H,d,J=14.7 Hz), 4.82(1H,d,J=14.7 Hz), 7.00(2H,t-like,J=8.6 Hz), 7.33–7.43(2H,m), 7.56(2H,s), 7.84(1H,s), 8.87(1H,s)

EXAMPLE 42

N-[3,5-Bis(trifluoromethyl)benzyl]-4,5-dihydro-N,5-dimethyl-4-oxo-7-phenyl-6-thiazolo[5,4-c]pyridinecarboxamide m.p.175°–176° C. (recrystallized from ethyl acetate-hexane)

NMR(200 MHz,CDCl$_3$) ppm: 2.69(3H,s), 3.67(3H,s), 4.44(1H,d,J=14.6 Hz), 4.66(1H,d,J=14.6 Hz), 7.25–7.36(3H,m), 7.38–7.48(2H,m), 7.56(2H,s), 7.82(1H,s), 9.12(1H,s)

EXAMPLE 43

N-[3,5-Bis(trifluoromethyl)benzyl]-4,5-dihydro-N,5-dimethyl-4-oxo-7-phenyl-6-thiazolo[4,5-c]pyridinecarboxamide m.p.220°–221°–221° C. (recrystallized from ethyl acetate-isopropyl ether)

NMR(200 MHz,CDCl$_3$) ppm: 2.72(3H,s), 3.68(3H,s), 4.35(1H,d,J=14.6 Hz), 4.78(1H,d,J=14.6 Hz), 7.25–7.45(5H,m), 7.53(2H,s), 7.81(1H,s), 8.86(1H,s)

EXAMPLE 44

N-[3,5-bis(trifluoromethyl)benzyl]-6,7-dihydro-N, 6-dimethyl-7-oxo-4-phenyl-5-thieno[2,3-c]pyridinecarboxamide m.p.194°–196° C. (recrystallized from ethyl acetate)
NMR(200MHz,CDCl$_3$) ppm: 2.69(3H,s), 3.64(3H,s), 4.36 (1H,d,J=14.6 Hz), 4.36(1H,d,J=14.6 Hz), 6.98(1H,d,J= 5.4 Hz), 7.3(5H,m), 7.53(2H,s), 7.67(1H,d,J=5.4 Hz), 7.81(1H,s)

EXAMPLE 45

6,7-Dihydro-N-(2-methoxybenzyl)-6-methyl-7-oxo-4-penyl-5-thieno[2,3-c]pyridinecarboxamide m.p.247°–249° C. (recrystallized from ethyl acetate-THF)
NMR(200 MHz,CDCl$_3$) ppm: 3.64(3H,s), 3.70(3H,s), 4.29(2H,d,J=6.4 Hz), 6.23(1H,b), 6.7–6.9(4H,m), 6.96(1H, d,J=5.6 Hz), 7.2–7.3(5H,m), 7.60(1H,d,J=5.6 Hz)

EXAMPLE 46

6,7-Dihydro-N-(2-methoxybenzyl)-N, 6-dimethyl-7-oxo-4-phenyl-5-thieno[2,3-c]pyridinecarboxamide m.p.154.6°–155.4° C. (recrystallized from ethyl acetate-isopropyl ether)
NMR(200 MHz,CDCl$_3$) ppm: 2.63(3H,s), 3.65(3H,s), 3.76(3H,s), 4.48(1H,d,J=15.0 Hz), 4.60(1H,d,J=15.0 Hz), 6.38(1H,d,J=6.6 Hz), 6.71 (1H,t,J=7.6 Hz), 6.80(1H,d,J=8.0 Hz), 6.99(1H,d,J=5.2 Hz), 7.20 (1H,t,J=7.0 Hz), 7.43(5H, m), 7.65(1H,d,J=5.2 Hz)

EXAMPLE 47

N-[3,5-Bis(trifluoromethyl)benzyl]-6,7-dihydro-N, 6-dimethyl-4-(2-methylphenyl)-7-oxo-5-thieno[2,3-c]pyridinecarboxamide A colorless oily product NMR(200 MHz,CDCl$_3$) ppm: 2.08(3H×2/5,s), 2.13(3H× 3/5,s), 2.74(3H×2/5,s), 2.94(3H×3/5,s), 3.62(3H×3/5,s), 3.64(3H×2/5,s), 4.12(1H×3/5,d,J=14.6 Hz), 4.29(1H×2/5,d, J=14.4 Hz), 4.78(1H×2/5,d,J=14.4 Hz), 4.98(1H×3/5,d,J= 14.6 Hz), 6.63(1H×3/5,d,J=5.2 Hz), 6.72(1H×2/5,d,J=5.2 Hz), 6.96(1H,m), 7.0(2H,m), 7.5(1H,m), 7.63(1H,m), 7.81(1H,m)

EXAMPLE 48

6-[N-[3,5-Bis(trifluoromethyl)benzyl]-N-methylamino carbonyl]-7,8-dihydro-1,7-dimethyl-8-oxo-5-phenylpyrido 3,4-b]pyridinium iodide Employing the compound obtained in Example 36 and iodomethane, substantially the same reaction and work-up as in Example 29 were conducted to give the above-titled compound as yellow crystals.

m.p.173°–175° C. (decomp.) (recrystallized from dioxaneethyl acetate)
NMR(200 MHz,CDCl$_3$) ppm: 3.04(3H,s), 3.62(3H,s), 4.19(1H,d,J=14 Hz), 4.79(1H,d,J=14 Hz), 5.01(3H,s), 7.3–7.5(7H,m), 7.80(1H,s), 8.0–8.1(2H,m), 9.32(1H,bs)

EXAMPLE 49

N-[3,5-Bis(trifluoromethyl)benzyl]-1,2,3,4,7,8-hexahydro-5-phenyl-N,1,7-trimethyl-8-oxo-6-pyrido[3,4-b]pyridinecarboxamide Employing the compound obtained in Example 47, substantially the same reaction (reduction) and process as in Example 30 were conducted to give the above-titled compound as colorless crystals. m.p.135°–137° C. (recrystallized from ethyl acetate-isopropyl ether)
NMR(200 MHz,CDCl$_3$) ppm: 1.69(2H,m), 1.87–2.38(2H,m), 2.73(3H,s), 3.04(3H,s), 3.08(2H,m), 3.49(3H,s), 4.19(1H,d, J=14.4 Hz), 4.70(1H,d,J=14.4 Hz), 7.03–7.38(5H,m), 7.46(2H,s), 7.77(1H,s)

EXAMPLE 50

N-[3,5-Bis(trifluoromethyl)benzyl]-1,2,5,6,7,8-hexahydro-N,2,7-trimethyl-1-oxo-4-phenyl-3-pyrido[3,4-c]pyridinecarboxamide Employing the compound obtained in Example 37, substantially the same reaction (methylation) and process as in Example 31 and substantially the same reaction (reduction) and process as in Example 32 were conducted to give the above-titled compound as colorless crystals.

m.p.138°–140° C. (recrystallized from ethyl acetate-isopropyl ether)
NMR(200 MHz ,CDCl$_3$) ppm: 1.98–2.70(4H,m), 2.47(3H,s), 2.71(3H,s), 3.24(1H,d,J=17 Hz), 3.51(3H,s), 3.75(1H,d, J=17 Hz), 4.16(1H,d,J=14.5 Hz), 4.74(1H,d, J=14.5 Hz), 7.03–7.32(5H,m), 7.44(2H,s), 7.77(1H,s)

EXAMPLE 51

N-[3,5-Bis)trifluoromethyl)benzyl]-1,2,3,4,5,6-hexahydro-N,6-dimethyl-5-oxo-8-phenyl-7-pyrido[4,3-b]pyridinecarboxamide Employing the compound obtained in Example 38, substantially the same reaction (reduction) and process as in Example 27 were conducted to give the above-titled compound as colorless crystals. m.p.229°–231° C. (recrystallized from methanol-ethyl ether)
NMR (200 MHz,CDCl$_3$) ppm: 1.86(2H,m), 2.64(2H,t-like,J=6.2 Hz), 2.74(3H,s), 3.17(2H,m), 3.43(3H,s), 3.92(1H,b), 4.14(1H,d,J=14.6 Hz), 4.77(1H,d,J=14.6 Hz), 7.13(1H,m), 7.26(4H,m), 7.44(2H,s), 7.77(1H,s)

EXAMPLE 52

N-[3,5-Bis(trifluoromethyl)benzyl]-1,2,3,4,5,6-hexahydro-N,1,6-trimethyl-5-oxo-8-phenyl-7-pyrido[4,3-b]pyridinecarboxamide Employing the compound obtained in Example 51, substantially the same reaction (methylation) and process as in Example 28 were conducted to give the above-titled compound as colorless crystals. m.p.233°–235° C. (recrystallized from methanol-ethyl ether)
NMR(200 MHz,CDCl$_3$) ppm: 1.82(2H,m), 2.18(3H,s), 2.53(3H,s), 2.63(2H,m), 3.03(2H,m), 3.45(3H,s), 4.30(1H, d,J=14.6 Hz), 4.56(1H,d,J=14.6 Hz), 7.18(4H,s), 7.35(1H, m), 7.50(2H,s), 7.80(1H,s)

EXAMPLE 53

N-[3,5-Bis(trifluoromethyl)benzyl]-4-(4-fluorophenyl)-1,2,5,6,7,8-hexahydro-N,2-dimethyl-1-oxo-3-pyrido[3,4-c]pyridinecarboxamide To a solution of the compound (270 mg) obtained in Example 8 in acetic acid (15 ml) was added 5% Pt-C (270 mg), and the mixture was stirred for 6 hours at room temperature under hydrogen atmosphere. The catalyst was filtered off, and the filtrate was washed with ethyl acetate. The filtrate and the washing were combined, then the solvent was distilled off. To the residue was added ethyl acetate, and the mixture was washed with an aqueous solution of sodium hydrogencarbonate and water, which was then dried. The solvent was distilled off to leave the above-titled compound as colorless crystals (170 mg). m.p.178°–180° C. (recrystallized from ethyl acetate-ethyl ether)

NMR(200 MHz,CDCl$_3$) ppm: 1.92(1H,d-like,J=17 Hz), 2.3–2.5( 1H,m), 2.7–2.9(1H,m), 2.77(3H,s), 3.0–3.1(1H,m), 3.50(3H,s), 3.81(1H,d,J=18 Hz), 3.98(1H,d,J=18 Hz), 4.19(1H,d,J=14.4 Hz), 4.77(1H,d,J=14.4 Hz), 6.8–7.2(4H,m), 7.50(2H,s), 7.81(1H,s)

EXAMPLE 54

N-[3,5-Bis(trifluoromethyl)benzyl]-1,2,5,6,7,8-hexahydro-N,2-dimethyl-1-oxo-4-phenyl-3-pyrido[3,4-c]pyridinecarboxamide The compound obtained in Example 37 was subjected to reduction and processed in substantially the same manner as in Example 53 to give the above-titled compound as colorless crystals (isolated as hydrochloride).

m.p.255°–257° C. (decomp.) (recrystallized from ethanol)

NMR(200 MHz,CDCl$_3$) ppm: 2.2–2.7(1H,m), 2.73(3H,s), 2.9–3.1(2H,m), 3.50(3H,s), 3.5(1H,m), 4.05(1H,d,J=18 Hz), 4.19(1H,d,J=14.5 Hz), 4.36(1H,d,J=18 Hz), 4.71(1H,d,J=14.5 Hz), 7.06–7.30(5H,m), 7.45(2H,s), 7.79(1H,s), 10.3(2H,b)

EXAMPLE 55

N-[3,5-Bis(trifluoromethyl)benzyl]-1,2,3,4,7,8-hexahydro-5-phenyl-N,7-dimethyl-8-oxo-6-pyrido[3,4-b]pyridinecarboxamide The compound obtained in Example 36 was subjected to reduction and process in substantially the same manner as in Example 53 to give the above titled compound as colorless crystals.

m.p.155°–156° C. (recrystallized from ethyl ether-hexane)

NMR(200 MHz,CDCl$_3$) ppm: 1.59–2.10(3H,m), 2.28–2.49(1H,m), 2.67(3H,s), 3.2–3.5(2H,m), 3.56(3H,s), 4.25(1H,d, J=14.6 Hz), 4.62(1H,d,J=14.6 Hz), 7.10(1H,m), 7.22(4H,m), 7.48(2H,s), 7.77(1H,s)

EXAMPLE 56

N-[3,5-Bis(trifluoromethyl)benzyl]-7,8-dihydro-N,7-dimethyl-5-(4-methylphenyl)-8-oxo-6-pyrido[3,4-b]pyridinecarboxamide The compound obtained in Reference Example 25 was subjected to the reaction and work-up in substantially the same manner as in Example 1 to give the above-titled compound as colorless crystals.

m.p.197°–199° C. (recrystallized from acetone-isopropyl ether)

NMR(200 MHz,CDCl$_3$) ppm: 2.33(3H,s), 2.80(3H,), 3.66(3H,s), 4.27(1H,d,J=14.5 Hz), 4.79(1H,d,J=14.5 Hz), 7.01–7.28(4H,m), 7.46(1H,dd,J=8,4 Hz), 7.57(2H,s), 7.60(1H,dd,J=8,2 Hz), 7.81(1H,s), 8.91(1H,dd,J=4,2 Hz)

The mother liquor was subjected to silica-gel column chromatography [methyl acetate dichloromethane=4:1] to give the amide-rotamer of the above compound as colorless crystals.

m.p. 164°–166° C.

NMR(200 MHz,CDCl$_3$) ppm: 2.46(3H,s), 2.73(3H,s), 3.69(3H,s), 4.21(1H,d,J=16 Hz), 4.58(1H,d,J=16 Hz), 7.03–7.80(9H,m), 8.92(1H,dd,J=4.4,1.6 Hz)

The former compound was used for the biological assay shown in Table 1 and 2.

EXAMPLE 57

N-[3,5-Bis(trifluoromethyl)benzyl]-7,8-dihydro-5-(4-methoxyphenyl)-N,7-dimethyl-8-oxo-6-pyrido[3,4-b]pyridinecarboxamide The compound obtained in Reference Example 26 was subjected to reaction and process in substantially the same manner as in Example 1 to give the above-titled compound as colorless crystals.

m.p.195°–197° C. (recrystallized from ethyl acetate-ethyl ether)

NMR(200 MHz,CDCl$_3$) ppm: 2.80(3H,s), 3.66(3H,s), 3.82(3H,s), 4.42(1H,d,J=14.4 Hz), 4.71(1H,d,J=14.4 Hz), 6.8–7.6(6H,m), 7.57(2H,s), 7.81(1H,s), 8.9(1H,m)

EXAMPLE 58

N-[3,5-Bis(trifluoromethyl)benzyl]-1,2-dihydro-N,2-dimethyl-4-(4-methylphenyl)-1-oxo-3-pyrido[3,4-c]pyridinecarboxamide The compound obtained in Reference Example 27 was subjected to reaction and process in substantially the same manner as in Example 1 to give the above-titled compound as colorless crystals.

m.p.166°–168° C. (recrystallized from ethyl acetate-ethyl ether)

NMR(200 MHz,CDCl$_3$) ppm: 2.33(3H,s), 2.80(3H,s), 3.60(3H,s), 4.32(1H,d,J=14.4Hz), 4.75(1H,d,J=14.4 Hz), 7.00–7.30(5H,m), 7.57(2H,s), 7.82(1H,s), 8.65(1H,bd), 9.69(1H,s)

EXAMPLE 59

N-[3,5-Bis(trifluoromethyl)benzyl]-1,2,5,6,7,8-hexahydro-N,2,7-trimethyl-4-(4-methylphenyl)-1-oxo-3-pyrido[3,4-c]pyridinecarboxamide The compound obtained in Example 58 was subjected to reactions and processes in substantially the same manner as in Example 31 (N-methylation) and Example 32 (reduction) to give the above-titled compound as colorless crystals.

m.p.126°–128° C. (recrystallized from ethyl ether-hexane)

NMR(200 MHz,CDCl₃) ppm: 1.90–2.80(4H,m), 2.27(3H,s), 2.47(3H,s), 3.23(1H,d,J=17 Hz), 3.50(3H,s), 3.74(1H,d,J=17 Hz), 4.23(1H,d,J=15 Hz), 4.71(1H,d,J=15 Hz), 6.90–7.30(4H,m), 7.52(2H,s), 7.78(1H,s)

EXAMPLE 60

N-[3,5-Bis(trifluoromethyl)benzyl]-7,8-dihydro-N,7-dimethyl-5-(3-methylphenyl)-8-oxo-6-pyrido[3,4-b]pyridinecarboxamide The compound obtained in Reference Example 28 was subjected to reaction and process in substantially the same manner as in Example 1 to give the above-titled compound as colorless crystals.

m.p.178°–180° C. (recrystallized from acetone-ethyl ether)

NMR (200 MHz ,CDCl₃) ppm: 2.26(3H×1/2,s), 2.33(3H×1/2,s), 2.78(3H×1/2,s), 2.81(3H×1/2,s), 3.65(3H×1/2,s), 3.67 (3H×1/2,s), 4.23(1H×1/2,d,J=14.6 Hz), 4.37 (1H×1/2,d,J=14.6 Hz), 4.70(1H×1/2,d,J=14.6 Hz), 4.82(1H×1/2,d,J=14.6 Hz), 6.94(1H,bs), 7.1–7.2(3H,m), 7.4–7.5(3H,m), 7.56–7.64(1H,m), 7.80(1H,s), 8.91(1H,dd,J=4,2 Hz)

Compounds of Example 61 to 72 were prepared by employing carboxylic acids and benzylamines having substituents corresponding to the respective compounds, and allowing the reaction to proceed in substantially the same manner as in Example 1 (amidation), then by subjecting the reaction mixture to be worked up in substantially the same manner as in Example 1.

EXAMPLE 61

N-Benzyl-5-(4-fluorophenyl)-7,8-dihydro-N,7-dimethyl-8-oxo-6-pyrido[3,4-b]pyridinecarboxamide Isomer (amide-rotamer) A [TLC, SiO₂ (ethyl acetate: AcOH: H₂O=8:1:1); Rf, smaller]

m.p. 213°–215° C. (recrystallized from ethyl acetate)

NMR(200 MHz,CDCl₃) ppm: 2.70(3H,s), 3.68(3H,s), 4.00(1H,d,J=15 Hz), 5.00(1H,d,J=15 Hz), 6.72(2H,m), 7.05–7.57(9H,m), 8.92(1H,dd,J=2.4 Hz)

Isomer (amide-rotamer) B [TLC, SiO₂ (ethyl acetate:AcOH:H₂O=8:1:1); Rf, larger] (obtained as the 2nd crystals)

m.p. 213°–215° C. (recrystallized from ethyl acetate-ethyl ether: contains about 20% of Isomer A)

NMR(200 MHz,CDCl₃) ppm: 2.75(3H,s), 3.64(3H,s), 3.89(1H,d,J=15 Hz), 4.48(1H,d,J=15 Hz), 6.82(2H,m), 7.10–7.72(9H,m), 8.93(1H,dd,J=2,4 Hz).

EXAMPLE 62

N-(3,5-Dimethylbenzyl)-5-(4-fluorophenyl)-7,8-dihydro-N,7-dimethyl-8-oxo-6-pyrido[3,4-b]pyridinecarboxamide m.p. 178°–180° C. (recrystallized from methanol-ethyl acetate)

NMR(200 MHz,CDCl₃) ppm: 2.25(6H,s), 1.68(3H,s), 3.67(3H,s), 4.07(1H,d,J=14 Hz), 4.74(1H,d,J=14 Hz), 6.51(2H,s), 6.90(1H,s), 7.05–7.59(6H,m), 8.91(1H,m)

EXAMPLE 63

N-(2-Chlorobenzyl)-5-(4-fluorophenyl)-7,8-dihydro-N,7-dimethyl-8-oxo-6-pyrido[3,4-b]pyridinecarboxamide m.p. 243°–245° C. (recrystallized from methanolacetone)

NMR(200 MHz,CDCl₃) ppm: 2.79(3H,s), 3.70(3H,s), 4.33(1H,d,J=15 Hz), 5.02(1H,d,J=15 Hz), 6.28(1H,dd,J=2,8 Hz), 7.0–7.6(9H,m), 8.93(1H,m)

EXAMPLE 64

N-(3,5-Dimethylbenzyl)-7,8-dihydro-N,7-dimethyl-5-(4-methylphenyl)-8-oxo-6-pyrido[3,4-b]pyridinecarboxamide m.p. 140°–141° C. (recrystallized from acetone-ethyl ether)

NMR(200 MHz,CDCl₃) ppm: 2.24(6H,s), 2.43(3H,s), 2.67(3H,s), 3.66(3H,s), 4.22(1H,d,J=14 Hz), 4.57(1H,d,J=14 Hz), 6.55(2H,s), 6.89(1H,s), 7.05–7.65(6H,m), 8.90(1H, m)

EXAMPLE 65

N-(2-Chlorobenzyl)-7,8-dihydro-N,7-dimethyl-5-(4-methylphenyl)-8-oxo-6-pyrido[3,4-b]pyridinecarboxamide m.p. 233°–235° C. (recrystallized from acetone-methanol)

NMR(200 MHz,CDCl₃) ppm: 2.49(3H,s), 2.78(3H,s), 3.70(3H,s), 4.33(1H,d,J=15 Hz), 5.02(1H,d,J=15 Hz), 6.18(1H,d,J=8 Hz), 6.89–7.65(9H,m), 8.91(1H,m)

EXAMPLE 66

7,8-Dihydro-N,7-dimethyl-5-(4-methylphenyl)-8-oxo-N-(2-trifluoromethylbenzyl)-6-pyrido[3,4-b]pyridinecarboxamide m.p. 220°–222° C. (recrystallized from methanol)

EXAMPLE 67

7,8-Dihydro-N,7-dimethyl-5-(4-methylphenyl)-8-oxo-N-(3-trifluoromethylbenzyl)-6-pyrido[3,4-b]pyridinecarboxamide m.p. 134°–135° C. (recrystallized from methanol-isoproryl ether)

EXAMPLE 68

7,8-Dihydro-N,7-dimethyl-5-(4-methylphenyl)-8-oxo-N-(4-trifluoromethylbenzyl)-6-pyrido[3,4-b]pyridinecarboxamide m.p. 207°–209° C. (recrystallized from methanol-isoproryl ether)

EXAMPLE 69

N-(2,4-Difluorobenzyl)-7,8-dihydro-N,7-dimethyl-5-(4-methylphenyl)-8-oxo-6-pyrido[3,4-b]pyridinecarboxamide m.p. 198°–199° C. (recrystallized from acetone-methanol)

EXAMPLE 70

N-(2,6-Difluorobenzyl)-7,8-dihydro-N,7-dimethyl-5-(4-methylphenyl)-8-oxo-6-pyrido[3,4-b]pyridinecarboxamide m.p. 242°–243° C. (recrystallized from acetone)

EXAMPLE 71

N-(3,5-Difluorobenzyl)-7,8-dihydro-N,7-dimethyl-5-(4-methylphenyl)-8-oxo-6-pyrido[3,4-b]pyridinecarboxamide m.p. 210°–212° C. (recrystallized from acetone-ethyl ether)

EXAMPLE 72

N-(3,5-Dichlorobenzyl)-7,8-dihydro-N,7-dimethyl-5-(4-methylphenyl)-8-oxo-6-pyrido[3,4b]pyridinecarboxamide m.p. 162°–163° C. (recrystallized from acetone-ethyl ether)

EXAMPLE 73

N-[3,5-Bis(trifluoromethyl)benzyl]-5-[4-N-(3,5-bis(trifluoromethyl)benzyl]-N-methylcarbamoylphenyl]- 7,8-dihydro-N,7-dimethyl-8-oxo-6-pyrido[3,4-b]pyridinecarboxamide Using the compound obtained in Reference Example 29 and N-[3.5-bis(trifluoromethyl)benzyl]methylamine, substantially the same reaction and work-up as in Example 1 (amidation) were conducted to give the title compound as colorless crystals.

m.p. 190°–191° C. (recrystallized from ethyl acetate and isopropyl ether)

NMR(200 MHz,CDCl$_3$) ppm: 2.78(3H,s), 3.02(3H,s), 3.62(3H,s), 4.05–4.35(1H,m), 4.70–5.00(3H,m), 7.30–7.90(12H,m), 8.95(1H,dd,J=4.2,1.6 Hz).

EXAMPLE 74

N-[3,5-Bis(trifluoromethyl)benzyl]-5-(4-carboxyphenyl]-7,8-dihydro-N,7-dimethyl-8-oxo-6-pyrido[3,4-b]pyridinecarboxamide A mixture of the compound obtained in Example 73 (0.37 g), C.HCl (12 ml) and acetic acid (12 ml) was stirred for 6 hours under reflux. The solvent was distilled off and the residue was dissolved in 1N NaOH. The solution was washed with ethyl ether-THF. To the aqueous layer was added c.HCl to adjust the pH 2–3, which was subjected to extraction with ethyl acetate. The extract was washed with saturated aq. NaCl, and dried. The solvent was distilled off to give the titled compound as colorless crystals (121 mg).

m.p. 301°–302° C. (recrystallized from THF-isopropyl ether)

NMR(200 MHz,CDCl$_3$+DMSO-d$_6$) ppm: 2.80(3H,ss), 3.67(3H,s), 4.44(1H,d,J=14.5 Hz), 4.58(1H,d,J=14.5 Hz), 7.27(1H,m), 7.40–7.60(3H,m), 7.59(2H,s), 7.82(1H,s), 8.03(2H,t-like,J=7.9Hz), 8.94(1H,dd,J=4.2,1.8 Hz).

EXAMPLE 75

N-[3,5-Bis(trifluoromethyl)benzyl]-7,8-dihydro-5-(4-methoxycarbonylphenyl]-N,7-dimethyl-8-oxo-6-pyrido[3,4-b]pyridinecarboxamide To a mixture of the compound obtained in Example 74 (50 mg) and THF (15 ml) was added a solution of diazomethane (excess) in ethyl ether. After the mixture was stirred for 30 minutes at room temperature, the solvent was evaporated to give the titled compound as colorless crystals (25 mg).

m.p. 123°–125° C. (recrystallized from ethyl acetate isopropyl ether)

NMR(200 MHz ,CDCl$_3$) ppm: 2.81(3H,s), 3.67(3H,s), 3.97(3H,s), 4.28(1H,d,J=14 Hz), 4.75(1H,d,J=14 Hz), 7.25(1H,m), 7.40–7.60(3H,m), 7.55(2H,s), 7.79(1H,s), 7.85–8.02(2H,m), 8.94(1H,dd,J=4.0,1.8 Hz).

EXAMPLE 76

N-[3,5-Bis(trifluoromethyl)benzyl]-5-cyclohexyl-7,8-dihydro-N,7-dimethyl-8-oxo-6-pyrido[3,4-b]pyridinecarboxamide Using the compound obtained in Reference Example 30 and N-[3.5-bis(trifluoromethyl)benzyl]methylamine, substantially the same reaction and work-up as in Example 1 (amidation) were conducted to give the title compound as a pale yellow oil.

NMR(200 MHz,CDCl$_3$) ppm: 0.8–2.6(11H,m), 2.97(3H, s), 3.55(3H,s), 4.47(1H,d,J=14 Hz), 5.28(1H,d,J=14 Hz), 7.50–7.62(1H,m), 7.93(1H,s), 7.95(2H,s), 8.40–8.50(1H,m), 8.90–9.00(1H,m).

Reference Example 1

5-(4-Fluorophenyl)-7,8-dihydro-7-methyl-8-oxo-6-pyrido[3,4-b]pyridinecarboxylic acid Process 1
Step 1
To a mixture of 2,3-pyridinedicarboxylic anhydride (16.5 g) and fluorobenzene (120 ml) was added, while stirring at room temperature, anhydrous aluminum chloride (23.1 g). The reaction mixture was stirred for 3 hours under reflux, which was cooled and poured into a mixture of hydrochloric acid and ice-water. This mixture was made to be pH 2–3 with an aqueous solution of potassium carbonate, which was subjected to extraction with ethyl acetate. The extract solution was washed with water and dried, then the solvent was distilled off to leave 3-(4-fluorobenzoyl)-2-pyridinecarboxylic acid as colorless crystals (11.0 g). m.p.152°–153° C. (recrystallized from methanol-ethyl acetate)

NMR(200 MHz,CDCl$_3$) ppm: 7.35(2H,t-like,J=8.8 Hz), 7.68–7.80(3H,m), 7.99(1H,dd,J=1.8,7.6 Hz), 8.84(1H,dd,J=1.8,4.6 Hz)
Step 2

To a solution of the compound (1.50 g) obtained in Step 1 in dichloromethane (20 ml) were added thionyl chloride (1.8 ml) and DMF (one drop). The mixture was stirred for 40 minutes while heating under reflux. The solvent was distilled off, and the residue was dissolved in dichloromethane (15 ml). This solution was added to a mixture of N-methylglycine benzyl ester hydrochloride (1.30 g), triethylamine (3.5 ml) and dichloromethane (20 ml), which was stirred for 20 minutes at room temperature. The solvent was distilled off. To the residue was added water, which was subjected to extraction with ethyl acetate. The extract solution was washed with an aqueous solution of sodium hydrogencarbonate and water, which was then dried. The solvent was distilled off to leave N-benzyloxycarbonylmethyl-3-(4-fluorobenzoyl)-N-methyl-2-pyridinecarboxamide as an oily product (1.94 g).

NMR(200 MHz,CDCl$_3$) ppm: 3.13,3.19(each 3H,s), 4.20, 4.30(each 1H,s), 5.18,5.25(each 1H,s), 7.12(2H,m), 7.22–7.50(5H,m), 7.22(1H,dd,J=1.8,7.6 Hz), 7.75–7.90(2H, m), 8.39(1H,dd,J=1.8,4.8 Hz), 8.74(1H,dd,J=1.8,4.8 Hz)

Step 3

A mixture of the compound (1.94 g) obtained in Step 2, toluene (100 ml) and 1,8-diazabicyclo[5.4.0]undec-7-ene (0.83 ml) was stirred for 2 hours under reflux. The solvent was distilled off. To the residue was added ethyl acetate, which was washed with water, an aqueous solution of sodium hydrogencarbonate and water, successively, followed by drying. The solvent was distilled off to leave 5-(4-fluorophenyl)-7,8-dihydro-7-methyl-8-oxo-6-pyrido[3,4-b]pyridinecarboxylic acid benzyl ester as colorless crystals (440 mg).

m.p.217°–218° C. (recrystallized from methanol-ethyl acetate)

NMR(200 MHz,CDCl$_3$) ppm: 3.63(3H,s), 5.06(2H,s), 7.02(2H,t-like,J=8.8 Hz), 7.07–7.38(7H,m), 7.48(1H,dd,J= 4.2,8.4 Hz), 7.55 (1H,dd,J=1.8,8.4 Hz), 8.92(1H,dd,J=1.8, 8.4 Hz)

Step 4

A mixture of the compound (100 mg) obtained in Step 3, 10% Pd-C (50% hydrous) (50 mg), methanol (5 ml) and THF (1 ml) was stirred for 20 minutes under hydrogen atmosphere. The catalyst was filtered off, and the solvent of the filtrate was distilled off to leave the above-titled compound as colorless crystals (66 mg).

m.p.238°–239° C. (recrystallized from methanol-ethyl acetate)

NMR(200 MHz, DMSO-d$_6$) ppm: 3.53(3H,s), 7.21(2H,t-like,J=9.0 Hz), 7.39(2H,m), 7.45–7.61(2H,m), 8.68(1H,dd, J=1.8,4.0 Hz)

Elemental Analysis for C$_{16}$H$_{11}$N$_2$O$_3$F. 1/8H$_2$O: Calcd.: C, 63.95; H, 3.73; N, 9.32 Found: C, 63.91; H, 3.57; N, 9.32

Process 2

Step 1

To a solution of 3-(4-fluorobenzoyl)-2-pyridinecarboxylic acid (19.8 g) in dichloromethane (200 ml) were added thionyl chloride (29.1 ml) and DMF (one drop). The mixture was stirred for 4 hours at room temperature. The solvent was distilled off, and the residue was dissolved in dichloromethane (100 ml). This solution was added to a mixture of N-methylaminoacetonitrile hydrochloride (9.46 g), triethylamine (33.7 ml) and dichloromethane (150 ml), which was stirred for 16 hours at room temperature. The solvent was distilled off. To the residue was added water, which was subjected to extraction with ethyl acetate. The extract solution was washed with an aqueous solution of sodium hydrogencarbonate and water, which was then dried, followed by distilling off the solvent to leave N-cyanomethyl-3-(4-fluorobenzoyl)-N-methyl-2-pyridinecarboxamide (22.8 g).

NMR(200 MHz,CDCl$_3$) ppm: 3.16(3H×1/3,s), 3.21(3H× 2/3,s), 4.44(2H×2/3,s), 4.55(2H×1/3,s), 7.17(2H,t,J=8.4 Hz), 7.50(1H,m), 7.85(3H,m), 8.75(1H,dd,J=1.6,4.8 Hz)

Step 2

A mixture of the compound obtained in Step 1 (22.8 g), toluene (300 ml) and 1,8-diazabicyclo[5.4.0]-7-undecene (13.2 ml) was stirred for 16 hours under reflux. The solvent was distilled off. To the residue was added water, then resulting crystalline precipitates were collected by filtration. The crystals were washed with water, methanol and ethyl ether to give 5-(4-fluorophenyl)-7,8-dihydro-7-methyl-8-oxo-6-pyrido[3,4-b]pyridinecarbonitrile as colorless crystals (14.9 g).

m.p.231°–232° C. (recrystallized from methanol-dichloromethane-ethyl ether)

NMR(200 MHz, CDCl$_3$) ppm: 3.92(3H,s), 7.29(2H,t-like, J=8.8 Hz), 7.36–7.48(2H,m), 7.60(1H,dd,J=4.2,8.4 Hz), 7.71(1H,dd,J=1.8,8.4 Hz), 9.04(1H,dd,J=8.4,4.2 Hz)

Step 3

A mixture of the compound (14.37 g) obtained in Step 2, ethanol (100 ml) and 1N NaOH (100 ml) was stirred for 3 hours under reflux. The reaction mixture was concentrated, to which was added 1N HCl to adjust the pH to 5,then resulting crystalline precipitate was collected by filtration, which was washed with water, methanol and ethyl ether to give 5-(4-fluorophenyl)-7,8-dihydro-7-methyl-8-oxo-6-pyrido[3,4-b]pyridinecarboxamide as colorless crystals (14.85 g).

m.p.329°–330° C. (recrystallized from methanol-dichloromethane-ethyl ether)

NMR(200 MHz,DMSO-d$_6$) ppm: 3.56(3H,s), 7.25–7.55(5H,m), 7.66(1H,dd,J=4.2,8.4 Hz), 7.86(1H,bs), 8.11(1H,bs), 8.83(1H,dd,J=1.6,4.2 Hz)

Step 4

To a mixture of the compound (2.36 g) obtained in Step 3 and conc. HCl (30 ml) was added portionwise sodium nitrite (15.0 g) which was stirred for 60 hours. To the reaction mixture was added water, whose pH was adjusted to 3 with an aqueous solution of potassium carbonate. The solvent was distilled off. Using Amberlite XAD-2, the residue was eluted with water:ethanol (1:0–0:4) to give the above-titled compound as colorless crystals (0.82 g).

Reference Example 2

8-(4-Fluorophenyl)-5,6-dihydro-6-methyl-5-oxo-7-pyrido [3,4-b]pyrazinecarboxylic acid Step 1

To a suspension of magnesium (4.2 g) in THF (20 ml) was added iodine (catalytic amount) while stirring at room temperature under argon atmosphere. To the mixture was then added dropwise a solution of 1-bromo-4-fluorobenzene (22.8 g) in THF (60 ml), and the mixture was stirred for 30 minutes. The mixture was added dropwise, while stirring at room temperature, to a solution of 2,3-pyrazinedicarboxylic anhydride (20.0 g) in THF (100 ml), followed by stirring for one hour. The reaction mixture was poured into dilute HCl (adjusting the pH to 4 to 5), followed by extraction with ethyl acetate. The extract solution was washed with water and dried, then the solvent was distilled off to give 3-(4-fluorobenzoyl)-2-pyrazinecarboxylic acid as a colorless oily product (25.8 g).

NMR(200 MHz,DMSO-d$_6$) ppm: 7.31(2H,t-like,J=8.8 Hz), 7.60–7.75(2H,m), 8.84(1H,d,J=2.5 Hz), 8.88(1H,d,J= 2.5 Hz)

This compound was used for the next reaction without purification.

Step 2

To a suspension of the compound (15.8 g) obtained in Step 1 in benzene (200 ml) were added thionyl chloride (35 ml) and DMF (one drop). The mixture was stirred for 2 hours under reflux. The solvent was distilled off, and the residue was dissolved in THF (50 ml). This solution was added to a mixture of N-methyl glycine ethyl ester hydrochloride (15.0 g), triethylamine (30.0 ml) and THF (80 ml), which was stirred for 16 hours at room temperature. The solvent was distilled off. To the residue was added water, which was subjected to extraction with ethyl acetate. The extract solution was washed with dilute hydrochloric acid and water successively, which was dried, then the solvent was distilled off. The residue was purified by means of a silica-gel column chromatography (hexane:ethyl acetate= 1:2) to give N-ethoxycarbonylmethyl-3-(4-fluorobenzoyl)-N-methyl-2-pyrazinecarboxamide as an oily product (5.07 g).

NMR(200 MHz,CDCl$_3$) ppm: 1.31(3H,t,J=7.2 Hz), 3.19(3H,s), 3.22(3H,s), 4.18–4.33(4H,m), 7.16(2H,t-like,J= 8.7 Hz), 7.95–8.10(2H,m), 8.59(2H,m)

Step 3

A mixture of the compound (5.07 g) obtained in Step 2, toluene (150 ml) and 1,8-diazabicyclo[5.4.0]-7-undecene (2.5 ml) was stirred for 16 hours under reflux. The reaction mixture was added to dilute hydrochloric acid (adjusted to pH 4-5), which was subjected to extraction with ethyl acetate-THF. The extract solution was washed with a saturated aqueous saline solution, which was dried, then the solvent was distilled off. The residue was purified by means of a silica-gel column chromatography (chloroform:acetone=10:1) to give 8-(4-fluorophenyl)-5,6-dihydro-6-methyl-5-oxo-7-pyrido[3,4-b]pyrazinecarboxylic acid ethyl ester as colorless crystals (1.21 g).

m.p.221°–222° C. (recrystallized from ethyl acetate-THF-ethyl ester)

NMR(200 MHz, CDCl$_3$) ppm: 1.04(3H,t,J=7.2 Hz), 3.70(3H,s), 4.15(2H,q,J=7.2 Hz), 7.16(2H,t-like,J=8.7 Hz), 7.27–7.40(2H,m), 8.87(2H,s)

Step 4

A mixture of the compound (1.10 g) obtained in Step 3, ethanol (25 ml), THF (25 ml) and 1N-NaOH (13 ml) was stirred for one hour under reflux. The reaction mixture was cooled, to which was added dilute HCl to adjust the pH to 3-4. The mixture was saturated with NaCl, followed by extraction with ethyl acetate. The extract solution was dried, then the solvent was distilled off to leave the above-titled compound as colorless crystals (0.93 g).

m.p.247°–249° C. (recrystallized from THF-ethyl ether)

NMR(200 MHz,CDCl$_3$) ppm:3.75(3H,s), 4.95(1H,bs), 7.14(2H,t-like,J=8.8 Hz), 7.34–7.48(2H,m), 8.83(1H,d,J= 2.0 Hz), 8.85(1H,d,J=2.0 Hz)

Elemental Analysis for $C_{15}H_{10}N_3O_3F.0.2H_2O$: Calcd.: C, 59.49; H, 3.46; N, 13.87 Found: C, 59.59; H, 3.71; N, 13.72

Reference Example 3

4-(4-Fluorophenyl)-1,2-dihydro-2-methyl-1-oxo-3-pyrido[3,4-c]pyridinecarboxylic acid Step 1

To a mixture of 3,4-pyridinedidicarboxylic anhydride (8.50 g) and fluorobenzene (170 ml) was added, while stirring at room temperature, anhydrous aluminum chloride (12.0 g). The reaction mixture was stirred for 3 hours under reflux, which was then cooled and poured into a mixture of hydrochloric acid and icewater. This mixture was rendered to pH 4 with an aqueous solution of sodium hydrogencarbonate. Resulting crystalline precipitate was collected by filtration to give 3-(4-fluorobenzoyl)-4-pyridine carboxylic acid as colorless crystals (1.51 g).

m.p.305°–310° C. (decomp.) (recrystallized from methanol-ethyl acetate)

NMR(200 MHz,DMSO-d$_6$) ppm: 7.36(2H,d,J=8.8 Hz), 7.76(2H,t-like,J=8.0 Hz), 7.88(1H,d,J=5.2 Hz), 8.73(1H,s), 8.94(1H,d,J=5.2 Hz)

The mother liquor and the filtrate were combined, which was subjected to extraction. The extract solution was washed with a saturated aqueous saline solution and dried, then the solvent was distilled off to give 4-(4-fluorobenzoyl)-3-pyridinecarboxylic acid as colorless crystals (2.27 g).

m.p.217°–219° C. (recrystallized from methanol-ethyl ether)

NMR (200 MHz,DMSO-d$_6$) ppm: 7.35(2H,t-like,J=8.5 Hz), 7.53(1H,d,J=5.0 Hz), 7.75(2H,m), 8.92(1H,d,J=5.0 Hz), 9.17(1H,s)

Step 2

Employing 4-(4-fluorobenzoyl)-3-pyridinecarboxylic acid obtained in Step 1 and N-methylglycine ethyl ester hydrochloride, substantially the same reaction and process as in Reference 2, Step 2 were conducted to give N-methyl-3-ethoxycarbonylmethyl-4-(4-fluorobenzoyl)-N-pyridine carboxamide as a colorless oily product.

NMR(200 MHz,CDCl$_3$) ppm: 1.29(3H,t,J=7.0 Hz), 3.07(3H,s), 4.16(2H,s), 4.22(2H,q,J=7.0 Hz), 7.16 (2H,t-like,J=8.0 Hz), 7.27–7.37 (1H,m), 7.81–7.87(2H,m), 8.75–8.82(2H,m)

Step 3

Employing the compound obtained in Step 2 and 1,8-diazabicyclo[5.4.0]-7-undecene, substantially the same reaction and process as in Reference 2,Step 3 were conducted to give 4-(4-fluorophenyl)-1,2-dihydro-2-methyl-1-oxo-3-pyrido[3,4-c]pyridinecarboxylic acid ethyl ester as colorless crystals.

m.p.158°–160° C. (recrystallized from ethyl acetate-isopropyl ether)

NMR(200 MHz,CDCl$_3$) ppm: 1.01(3H,t,J=7.0 Hz), 3.61(3H,s), 4.10(2H,q,J=7.0 Hz), 7.03(1H,d,J=5.6 Hz), 7.13–7.34(4H,m), 8.69(1H,d,J=5.6 Hz), 9.69(1H,s)

Step 4

Employing the compound obtained in Step 3 and an aqueous solution of sodium hydroxide, substantially the same reaction and process as in Reference Example 2, Step 4 were conducted to give the above-titled compound as colorless crystals.

m.p.246°–247° C. (decomp.) (recrystallized from THF-methanol)

NMR(200 MHz,DMSO-d$_6$) ppm: 3.54(3H,s), 7.00(1H,d, J=5.6 Hz), 7.33–7.38(4H,m), 8.69(1H,d,J=5.6 Hz), 9.46(1H, s)

Elemental Analysis for $C_{16}H_{11}N_2O_3F.1/4H_2O$: Calcd.: C, 63.47; H, 3.83; N, 9.25 Found: C, 63.37; H, 3.80; N, 9.30

Reference Example 4

4-(4-Fluorophenyl)-1,2-dihydro-2-methyl-1-oxo-3-pyrido[4,3-c]pyridinecarboxylic acid Step 1

Employing 3-(4-fluorobenzoyl)-4-pyridinecarboxylic acid obtained by the method of Reference Example 3, Step 1 and N-methylglycine ethyl ester hydrochloride, substantially the same reaction and process as in Reference 2, Step 2 were conducted to give N-ethoxycarbonylmethyl-3-(4-fluorobenzoyl)-N-methyl-4-pyridinecarboxamide as a colorless oily product.

NMR(200 MHz,CDCl$_3$) ppm: 1.31(3H,t,J=7.0 Hz), 3.00(3H,s), 4.20(2H,s), 4.24(2H,q,J=7.0 Hz), 7.18(2H,t-like,J=8.0 Hz), 7.40–7.48(1H,m), 7.85–7.92(2H,m), 8.77–8.86(2H,m)

Step 2

Employing the compound obtained in Step 1 and 1,8-diazabicyclo[5.4.0]-7-undecene, substantially the same reaction and process as in Reference Example were conducted to give 4-(4-fluorophenyl)-1,2-dihydro-2-methyl-1-oxo-3-pyrido[4,3-c]pyridinecarboxylic acid ethyl ester as colorless crystals, m.p.181°–183° C. (recrystallized from ethyl acetate-isopropyl ether).

NMR(200 MHz,CDCl$_3$) ppm: 1.01(3H,t,J=7.0 Hz), 3.63(3H,s), 4.09(2H,q,J=7.0 Hz), 7.14–7.38(4H,m), 8.26(1H,d,J=5.4 Hz), 8.63(1H,s), 8.75(1H,d,J=5.4 Hz)

Step3

Employing the compound obtained in Step 2 and an aqueous solution of sodium hydroxide, substantially the same reaction and process were conducted to give the above-titled compound as colorless crystals, m.p.294°–295° C. (decomp.) (recrystallized from THF-methanol).

NMR(200 MHz,CDCl$_3$) ppm: 3.55(3H,s), 7.31–7.45(4H,m), 8.13(1H,d,J=5.2 Hz), 8.47(1H,s), 8.73(1H,d,J=5.2 Hz)

Elemental Analysis for $C_{16}H_{11}N_2O_3F.1/4H_2O$: Calcd.: C, 63.47; H, 3.83; N, 9.25 Found: C, 63.48; H, 3.82; N, 9.35

Reference Example 5

5,6-Dihydro-6-methyl-8-(2-methylphenyl)-5-oxo-7-pyrido [4,3-b]pyridinecarboxylic acid Step 1

Employing 2,3-pyridinedicarboxylic anhydride (5.96 g) and 2-bromotoluene (8.2 g), substantially the same reaction and process as in Reference Example 2, Step 1, (Grignard reaction) were conducted to give a mixture of 2-(2-methylbenzoyl)-3-pyridinecarboxylic acid and 3-(2-methylbenzoyl)-2-pyridinecarboxylic acid as an oily product (6.45 g). (This compound was used for the subsequent reaction without purification.)

Step 2

Employing the compound (6.45 g) obtained in Step 1 and N-methylaminoacetonitrile hydrochloride (3.7 g), substantially the same reaction and process as in Reference Example 1-Process 2, Step 1 (amidation) were conducted to give a mixture of N-cyanomethyl-N-methyl-2-(2-methylbenzoyl)-3-pyridinecarboxamide and N-cyanomethyl-N-methyl-3-(2-methylbenzoyl)-2-pyridinecarboxamide as an oily product (7.5 g). (This compound was used for the subsequent reaction without purification.)

Step 3

Employing the compound (7.5 g) obtained in Step 2 and 1,8-diazabicyclo[5,4,0]-7-undecene (4.0 ml), substantially the same reaction as in Reference Example 1-Process 2, Step 2 (dehydrative cyclization reaction) (refluxing for 4 hours in toluene) was conducted, and the reaction mixture was purified by means of a silica gel column chromatography [hexane:ethyl acetate (2:1→1:1)-acetone]. From the first fraction, 5,6-dihydro-6-methyl-8-2-methylphenyl)-5-oxo-7-pyrido[4,3-b]pyridinecarbonitrile was obtained as colorless crystals (3.5 g), m.p.216°–218° C. (recrystallized from ethyl acetate-isopropyl ether).

NMR(200 MHz,CDCl$_3$) ppm: 2.12(3H,s), 3.87(3h,s), 7.26–7.44(4H,m), 7.54(1H,dd,J=4.6,8.1 Hz), 8.78(1H,dd,J=1.8,8.1 Hz), 8.97(1H,dd,J=1.8,4.6 Hz)

From the next fraction, 7.8-dihydro-7-methyl-5-(2-methylphenyl)-8-oxo-6-pyrido[3,4-b]pyridinecarbonitrile as colorless crystals (2.4 g), m.p.238°–240° C. (recrystallized from ethyl acetate)

NMR(200 MHz,CDCl$_3$) ppm: 2.12(3H,s), 3.92(3H,s), 7.34–7.59(6H,m), 9.02(1H,dd,J=1.8,4.4 Hz)

Step 4

Employing 5,6-dihydro-6-methyl-8-(2-methylphenyl)-5-oxo-7-pyrido[4,3-b]pyridinecarbonitrile (3.5 g) obtained in Step 3 and 1N-NaOH, substantially the same reaction as in Reference Example 1-Process 2, Step 3 (hydrolysis) (refluxing for 16 hours in ethanol) was conducted to give 5,6-dihydro-6-methyl-8-(2-methylphenyl)-5-oxo-7-pyrido[4,3-b]pyridinecarboxamide as colorless crystals (2.2 g), m.p.315°–320° C. (recrystallized from methanol).

NMR(200 MHz,DMSO-d$_6$) ppm:1.98(3H,s), 3.56(3H,s), 7.17–7.26(4H,m), 7.54(1H,dd,J=4.4,8.0 Hz), 7.80(1H,bs), 8.04(1H,bs), 8.62(1H,dd,J=1.8,8.0 Hz), 8.82 (1H,dd ,J=1.8, 4.4 Hz)

Step 5

To a mixture of the compound (2.2 g) obtained in Step 4 and hydrochloric acid (30 ml ) was added, in limited amounts, sodium nitrite (5.2 g) while stirring at 0° C. This mixture was stirred f or 3 hours at room temperature, whose pH was adjusted to a range of 5 to 6 by using sodium carbonate. Resulting precipitate was filtered off, and the filtrate was allowed to adsorb on Amberlite XAD-2 and eluted with methanol to give the above-titled compound as colorless crystals (0.83 g), m.p. 268°–273° C. (decomp.) (recrystallized from methanol-THF).

NMR (200 MHz, DMSO-d$_6$) ppm: 1.96(3H,s), 3.53(3H,s), 7.08–7.14(4H,m), 7.34 (1H,dd,J=4.4,8.0 Hz), 8.50(1H,dd,J=1.2,8.0 Hz), 8.69(1H,dd,J=1.2,4.4 Hz) SI-MS, m/z:295 (M+1)$^+$ Reference Example 6

5-(Chloro-2-methylphenyl)-7,8-dihydro-7-methyl-8-oxo-6-pyrido[3,4-b]pyridinecarboxylic acid and its isomer Step 1

Employing 7,8-dihydro-7-methyl-5-(2-methylphenyl)-8-oxo-6-pyrido[3,4-b]pyridinecarbonitrile (Reference Example 5, Step 3) (2.40 g) and !N-NaOH, substantially the same reaction (hydrolysis in ethanol by reflux for 16 hours) and process as in Reference Example 1-Process 2, Step 3 were conducted to give 7,8-dihydro-7-methyl-5-(2-methylphenyl)-8-oxo-6-pyrido[3,4-b]pyridinecarboxamide as colorless crystals (1.57 g), m.p.305°–307° C. (recrystallized from methanol-THF).

NMR(200 MHz,DMSO-d$_6$)ppm: 2.01(3H,s), 3.57(3H,s), 7.20(1H,dd,J=1.6,8.2 Hz), 7.26–7.36(4H,m), 7.63(1H,dd,J=4.4,8.2 Hz), 7.78(1H,bs), 8.04(1H,bs), 8.82(1H,dd,J=1.6,4.4 Hz)

Step 2

To a mixture of the compound (1.5 g) obtained in Step 1 and hydrochloric acid (30 ml) was added portionwise sodium nitrite(7.0 g), at 0° C. while stirring. This mixture was stirred for 20 hours at room temperature, whose pH was adjusted to a range of 5 to 6 with sodium carbonate. Resulting precipitate was filtered off, and the filtrate was adsorbed on Amberlite XAD-2 and eluted with methanol to give the above-titled compound (a mixture) as colorless crystals (0.9 g), m.p.290°–295° C. (decomp.) (recrystallized from methanol-THF).

NMR(200 MHz,DMSO-d$_6$) ppm: 1.97(3H×2/5,s), 2.03(3H×3/5,s), 3.56(3H,s), 7.11–7.47(4H,m), 7.54(1H,dd, J=4.2,8.2 Hz), 8.68(1H,dd,J=1.6,4.2 Hz) SI-MS, m/z: 329, 331 (M+1)$^+$

Reference Example 7

N-Methyl-4-(2-pyridyl)-3-quinolinecarboxamide

Step 1

A mixture of 2-(2-aminobenzoyl)pyridine (2.0 g) and diethyl ethoxymethylenemalonate (2.7 g) was stirred for 16 hours at 130° C., then resulting crystalline precipitate (3.0 g) was collected by filtration. A mixture of the crystalline product, lithium chloride (1.8 g) and DMSO (30 ml) was stirred for 2 hours at temperatures ranging from 180° to 190° C. The reaction mixture was cooled, which was poured into water, followed by extraction with chloroform. The extract was washed with water and dried, then the solvent was distilled off. The residue was subjected to a silica-gel column chromatography (hexane:ethyl acetate=1:2) to give ethyl ester of 4-(2-pyridyl)-3-quinolinecarboxylic acid as colorless crystals (1.28 g), m.p.70° C. (recrystallized from ethyl ether-hexane).

NMR(200 MHz,CDCl$_3$) ppm: 1.07(3H,t,J=7.2 Hz), 4.16(2H,q,J=7.2 Hz), 7.35–7.55(4H,m), 7.70–7.95(2H,m), 8.21(1H,d,J=8.4 Hz), 8.79(1H,d,J=4.4 Hz), 9.46(1H,s)

Step 2

A mixture of the compound (1.19 g) obtained in Step 1 and a 40% methylamine methanol solution (30 ml) was stirred for 3 days at room temperature. The solvent was distilled off to leave the above-titled compound as colorless crystals (666 mg), m.p.171°–172° C. (recrystallized from ethyl acetate-isopropyl ether).

NMR(200 MHz,CDCl$_3$) ppm: 2.72(3H,d,J=5.0 Hz), 6.33(1H,m), 7.40–7.55(4H,m), 7.70–7.95(2H,m), 8.17(1H, d,J=8.4 Hz), 8.79(1H,m), 9.17(1H,s)

Elemental Analysis for C$_{16}$H$_{13}$N$_3$O0.1H$_2$O Calcd.: C, 72.49; H, 5.02; N, 15.85 Found: C, 72.47; H, 4.83; N, 15.71

Reference Example 8

4-(4-Fluorophenyl)-6,7-dihydro-6-methyl-7-oxo-5-thieno [2,3-c]pyridinecarboxylic acid Step 1

To a mixture of 2,3-thiophenedidicarboxylic anhydride (1.98 g) and fluorobenzene (30 ml) was added, while stirring at room temperature, anhydrous aluminum chloride (2.7 g). The reaction mixture was stirred for 3.5 hours under reflux, cooled and poured into a mixture of hydrochloric acid-ice water. This mixture was subjected to extraction with ethyl acetate. The extract solution was washed with a saturated aqueous saline solution and dried, then the solvent was distilled off to leave 3-(4-fluorobenzoyl)-2-thiophenecarboxylic acid as colorless crystals (3.21 g), m.p.152° C. (recrystallized from ethyl ether-isopropyl ether).

NMR(200 MHz,CDCl$_3$) ppm: 7.10–7.30(3H,m), 7.66(1H,d,J=5.2 Hz), 7.80–7.95(2H,m)

Step 2

To a solution of the compound (3.21 g) obtained in Step 1 in THF (60 ml) were added oxalyl chloride (1.7 ml) and DMF (5 drops), and the mixture was stirred for 30 minutes at room temperature. The solvent was distilled off, and the residue was dissolved in THF (20 ml). This solution was added to a mixture of N-methyl glycine ethyl ester hydrochloride (2.5 g), triethylamine (4 ml) and THF (50 ml), which was subjected to extraction with ethyl acetate. The extract solution was washed with 2N HCl, an aqueous solution of sodium hydrogencarbonate and water, which was then dried. The solvent was distilled off, and the residue was subjected to a silica-gel column chromatography (hexane-:ethyl acetate=1:1) to give N-ethoxycarbonylmethyl-3-(4-fluorobenzoyl)-N-methyl-2-thiophenecarboxamide as an oily product (0.98 g).

NMR(200 MHz,CDCl$_3$) ppm: 1.27(3H,t,J=7.1 Hz), 2.99(3H,bs), 4.05(2H,s), 4.19(2H,q,J=7.1 Hz), 7.05–7.30(3H,m), 7.45(1H,m), 7.80–7.95(2H,m)

Step 3

A mixture of the compound (0.98 g) obtained in Step 2,toluene (50 ml) and 1,8-diazabicyclo[5.4.0]-7-undecene (1.5 ml) was stirred for 3 hours under reflux. The reaction mixture was cooled, which was poured into 2N HCl. This mixture was subjected to extraction with ethyl acetate. The extract solution was washed with water and dried, then the solvent was distilled off. The residue was subjected to a silica-gel column chromatography (hexane: ethyl acetate= 1:1) to give 4-(4-fluorophenyl)- 6,7-dihydro-6-methyl-7-oxo-5-thieno[2,3-c]pyridinecarboxylic acid ethyl ester, m.p.145°–147° C. (recrystallized from ethyl acetate-hexane).

NMR(200 MHz,CDCl$_3$) ppm: 1.01(3H,t,J=7.2 Hz), 3.65(3H,s), 4.10(2H,q,J=7.2 Hz), 6.92(1H,d,J=5.1 Hz), 7.13(2H,t-like,J=8.6 Hz), 7.25–7.40(2H,m), 7.67(1H,d,J= 5.1 Hz)

Step 4

Employing the compound (304 mg) obtained in Step 3, substantially the same reaction (hydrolysis) and process as in Reference Example 2, Step 4 were conducted to give the above-titled compound as colorless crystals (240 mg), m.p.205° C. (recrystallized from ethyl acetate-isopropyl ether).

NMR(200 MHz,CDCl$_3$) ppm: 3.70(3H,s), 6.93(1H,d,J= 5.3 Hz), 7.14(2H,t-like,J=8.6 Hz), 7.37–7.49(2H,m), 7.70(1H,d,J=5.3 Hz)

Elemental Analysis for C$_{15}$H$_{10}$NO$_3$SF: Calcd.: C, 59.40; H, 3.32; N, 4.62 Found: C, 59.24; H, 3.42; N, 4.55

Reference Example 9

7-(4-Fluorophenyl)-4,5-dihydro-5-methyl-4-oxo-6-thieno[3,2-c]pyridinecarboxylic acid Employing the filtrate after collecting the crystals obtained in Reference Example 8 Step 1, substantially the same reaction and process as in Reference Example 8 Step 2 were conducted to give N-ethoxycarbonylmethyl-2-(4-fluorobenzoyl)-N-methyl-3-thiophenecarboxamide as a pale yellow oily compound. This oily compound (1.4 g) was subjected to substantially the same reaction and process as in Reference Example 8 Step 3 to give ethyl ester of 7-(4-fluorophenyl)-4,5-dihydro-5-methyl-4-oxo-6-thieno[3,2-c]pyridine carboxylic acid as colorless crystals (1.27 g), m.p.127°–129° C. (recrystallized from ethyl acetate-isopropyl ether).

NMR(200 MHz,CDCl$_3$) ppm: 1.01(3H,t,J=7.2 Hz), 3.63(3H,s), 4.10(2H,q,J=7.2 Hz), 7.14(2H,t-like,J=8.7 Hz), 7.35–7.50(2H,m), 7.36(1H,d,J=5.3 Hz), 7.73(1H,d,J=5.3 Hz)

This ethyl ester (1.08 g) was subjected to substantially the same reaction and process as in Reference Example 8 Step 4 to give the above-titled compound a s colorless crystals (0.65 g), m.p.233° C. (recrystallized from ethyl acetate-THF-isopropyl ether).

NMR(200 MHz,CDCl$_3$) ppm: 3.69(3H,s), 5.08(1H,bs), 7.14(2H,t-like,J=8.Hz), 7.33(1H,d,J=5.4 Hz), 7.43–7.55(2H, m), 7.70(1H,d,J=5.4 Hz)

Reference Example 10

7-(4-Fluorophenyl)-4,5-dihydro-5-methyl-4-oxo-6-thieno [3,4-c]pyridinecarboxylic acid

Employing 3,4-thiophenedicarboxylic anhydride as the starting material, substantially the same reaction and work-up as in Step 1 to Step 4 of Reference Example 8 were conducted to give the above-titled compound. The compounds obtained in each step and the corresponding physico-chemical constants are as follows:

Step 1

4-(4-Fluorobenzoyl)-3-thiophenecarboxylic acid m.p.161°–162° C. (recrystallized from ethyl acetate-isopropyl ether)

NMR(200 MHz,CDCl$_3$) ppm: 7.18(2H,t-like,J=8.6 Hz), 7.76(1H,d,J=3.3 Hz), 7.80–7.95(2H,m), 8.39(1H,d,J=3.3 Hz), 9.90(1H,bs)

Step 2

N-Ethoxycarbonylmethyl-4-(4-fluorobenzoyl)-N-methyl-3-thiophenecarboxamide

A pale yellow oily substance (used for the subsequent reaction without purification)

Step 3

7-(4-Fluorophenyl)-4,5-dihydro-5-methyl-4-oxo-6-thieno[3,4-c]pyridinecarboxylic acid ethyl ester m.p.128°–129° C. (recrystallized from ethyl acetate-isopropyl ether)

NMR(200MH z,CDCl$_3$) ppm: 1.00(3H,t,J=7.2 Hz), 3.52(3H,s), 4.07(2H,q ,J=7.2 Hz), 7.05–7.20(3H,m), 7.30–7.45(2H,m), 8.42(1H,d ,J=2.6 Hz)

Step 4

7-(4-Fluorophenyl)-4,5-dihydro-5-methyl-4-oxo-6-thieno[3,4-c]pyridinecarboxylic acid (above-titled compound)

m.p.217°–218° C. (recrystallized from ethyl acetate-isopropyl ether)

NMR(200 MHz,CDCl$_3$) ppm: 3.58(3H,s), 7.06(1H,d,J=3.3 Hz), 7.12(2H,t-like,J=8.8 Hz), 7.40–7.50(2H,m), 8.40(1H,d,J=3.3 Hz)

Reference Example 11

8-(4-Fluorophenyl)-5,6-dihydro-6-methyl-5-oxo-7-pyrido [4,3-b]pyridinecarboxylic acid

Step 1

To a solution of 2,3-pyridinedicarboxylic anhydride (18.6 g) in THF (150 ml) was added, while stirring at room temperature, a solution of p-fluorophenyl magnesium bromide [prepared from p-bromofluorobenzene (13.6 ml) and magnesium (3.91 g)] in THF (100 ml). The reaction mixture was stirred for one hour at room temperature, which was poured into HCl-ice water, whose pH was adjusted to a range of 2–3 with 1N aqueous solution of sodium hydroxide, followed by extraction with ethyl acetate. The extract solution was washed with water and dried, then the solvent was distilled off to leave a mixture of 3-(4-fluorobenzoyl)-2-pyridinecarboxylic acid (Reference Example 1 Process 1 Step 1) and 2-(4-fluorobenzoyl)-3-pyridinecarboxylic acid as a colorless oily substance (10.5 g). This oily substance was subjected to a silica-gel column chromatography to separate these compounds from each other. Physico-chemical constants of the latter compound are as follows.

m.p.179°–181° C. (recrystallized from methanol-ethyl ether)

NMR(200 MHz,CDCl$_3$) ppm: 7.12(2H,t-like), 7.55(1H, dd,J=4.8,8.2 Hz), 7.81(2H,dd-like), 8.39(1H,dd,J=1.6,8.2 Hz), 8.84(1H,dd,J=1.6,5.0 Hz)

Step 2

2-(4-Fluorobenzoyl)-3-pyridinecarboxylic acid (1.50 g) obtained in Step 1 was subjected to substantially the same reaction and process as in Reference Example 1 Process 2 Step 1 to give N-cyanomethyl-N-methyl-2-(4-fluorobenzoyl)-3-pyridinecarboxamide as an oily product (1.8 g).

NMR(200 MHz,CDCl$_3$) ppm: 3.02(3H,s), 4.52(2H,s), 7.15(t-like), 7.55(1H,m), 7.81(1H,d,J=7.6 Hz), 8.08(2H,m), 8.73(1H,dd,J=1.6,4.8 Hz)

Step 3

The compound (2.04 g) obtained in Step 2 was subjected to substantially the same reaction and process as in Reference Example 1 Process 2 Step 2 to give 8-(4-fluorophenyl)-5,6-dihydro-6-methyl-5-oxo-7-pyrido[4,3-b]pyridinecarbonitrile as colorless crystals (1.55 g).

m.p.258°–259° C. (recrystallized from dichloromethane-ethyl acetate)

NMR(200 MHz,CDCl$_3$) ppm: 3.88(3H,s), 7.24(2H,t-like), 7.44–7.62(3H,m), 8.79(1H,dd,J=1.8,8.4 Hz), 8.99(1H, dd,J=1.8,4.4 Hz)

Step 4

The compound (1.00 g) obtained in Step 3 was subjected to substantially the same reaction and process as in Reference Example 1 Process 2 Step 3 to give 8-(4-fluorophenyl)-5,6-dihydro-6-methyl-5-oxo-7-pyrido[4,3-b]pyridinecarboxamide as colorless crystals (1.00 g).

m.p.300°–301° C. (recrystallized from methanol-ethyl ether)

NMR(200 MHz,CDCl$_3$) ppm: 3.71(3H,s), 5.42–5.67(2H, b), 7.16(2H,t-like), 7.45(3H,m), 8.75(1H,dd,J=1.8,8.0 Hz), 8.90(1H,dd,J=1.8,4.4 Hz)

Step 5

The compound (900 mg) obtained in Step 4 was subjected to substantially the same reaction and process as in Reference Example 1 Process 2 Step 4 to give the above-titled compound as colorless crystals (561 mg).

m.p.237° C. (decomp.) (recrystallized from methanol-ethyl ether)

NMR(200 MHz,DMSO-d$_6$) ppm: 3.54(3H,s), 7.25(2H,t-like), 7.37(2H,m), 7.58(1H,dd,J=4.4,8.2 Hz), 8.62(1H,dd,J=1.8,8.2 Hz), 8.88(1H,dd,J=1.8,4.4 Hz)

Reference Example 12

1,2-Dihydro-2-methyl-1-oxo-4-(2-thienyl)-3-isoquinoline carboxylic acid

Step 1

To a mixture of phthalic anhydride (2.96 g), dichloromethane (10 ml) and aluminum chloride (5.87 g) was added a solution of thiophene (1.6 g) in dichloromethane, in limited amounts, while stirring at room temperature, then the reaction mixture was stirred for one hour at room temperature. The reaction mixture was poured into HCl-ice water, followed by extraction with ethyl acetate. The extract solution was washed with water and dried, then the solvent was distilled off to leave 2-(2-thienylcarbonyl)benzoic acid as colorless crystals (2.72 g).

m.p.142°–143° C. (recrystallized from ethyl acetate-isopropyl ether)

NMR(200 MHz,CDCl$_3$) ppm: 7.06(1H,dd,J=3.6,4.8 Hz), 7.25(1H,dd,J=1.2,3.8 Hz), 7.46(1H,dd,J=1.6,7.2 Hz), 7.52–7.74(3H,m), 8.09(1H,dd,J=1.2,7.8 Hz)

Compounds of Step 2 to Step 4 were obtained by employing the compound obtained in Step 1 as the starting material, and conducting substantially the same reactions and processes as in Reference Example 8 Step 2 to Step 4. Compounds obtained in the respective steps and their physicochemical constants are as follows.

Step 2

N-Ethoxycarbonylmethyl-N-methyl-2-(2-thienylcarbonyl)benzenecarboxamide

A pale yellow oily product

NMR(200 MHz,CDCl$_3$) ppm: 1.19–1.37(3H,m), 2.99(3H×3/5,s), 3.09(3H×2/5,s), 4.00(2H×2/5,s), 4.09–4.30(2H+2H×3/5,m), 7.13(1H,t-like), 7.40–7.66(4H, m), 7.66–7.77(2H,m)

Step 3

1,2-Dihydro-2-methyl-1-oxo-4-(2-thienyl)-3-isoquinoline carboxylic acid ethyl ester m.p.137°–138° C. (recrystallized from ethyl acetate-isopropyl ether)

NMR(200 MHz,CDCl$_3$) ppm: 1.08(3H,t,J=7.4 Hz), 3.61(3H,s), 4.14(2H,q,J=7.4 Hz), 7.03–7.15(2H,m), 7.40–7.68(4H,m), 8.49(1H,m)

Step 4

1,2-Dihydro-2-methyl-1-oxo-4-(2-thienyl)-3-isoquinoline carboxylic acid (above-titled compound)

m.p.259°–260° C. (recrystallized from ethyl acetate-isopropyl ether)

NMR(200 MHz,CDCl$_3$) ppm: 3.65(3H,s), 7.12(2H,s), 7.39–7.70(4H,m), 8.46(1H,m)

Reference Example 13

4-(4-Fluorophenyl)-N-methyl-5-thieno[2,3-b]pyridine carboxamide

Step 1

A mixture of 4-fluorobenzoylacetonitrile (2.84 g), 2,5-dihydroxy-1,4-dithian (1.31 g), triethylamine (2.2 ml) and ethanol (15 ml) was stirred for 40 minutes at 50° C. The reaction mixture was cooled to give 2-amino-3-(4-fluorobenzoyl)thiophene as yellow crystals (2.22 g).

m.p.178° C. (recrystallized from ethyl ether-hexane)

NMR(200 MHz,CDCl$_3$): 6.15(1H,d,J=5.8 Hz), 6.85(1H, d,J=5.8 Hz), 6.94(2H,bs), 7.00–7.20(2H,m), 7.60–7.80(2H, m)

Step 2

The compound (872 mg) obtained in Step 1 was subjected to substantially the same reaction and process as in Reference Example 7 Step 1 to give ethyl ester of 4-(4-fluorophenyl)-5-thieno[2,3-b]pyridinecarboxylic acid as a pale yellow oily product (576 mg).

NMR(200 MHz,CDCl$_3$): 1.10(3H,t,J=7.1 Hz), 4.17(2H, q,J=7.1 Hz), 7.03(1H,d,J=6.0 Hz), 7.10–7.40(4H,m), 7.54(1H,d,J=6.0 Hz), 9.09(1H,s)

Step 3

The compound (576 mg) obtained in Step 2 was subjected to substantially the same reaction and process as in Reference Example 7 Step 2 to give the above-titled compound as colorless crystals (297 mg).

m.p.188°–189° C. (recrystallized from ethyl acetate-isopropyl ether)

NMR(200 MHz,CDCl$_3$): 2.77(3H,d,J=5.0 Hz), 5.43(1H, bs), 7.10(1H,d,J=6.1 Hz), 7.15–7.30(2H,m), 7.40–7.50(2H, m), 7.56(1H,d,J=6.1 Hz), 8.82(1H,s)

Reference Example 14

1,2-Dihydro-N,1-dimethyl-2-oxo-4-(2-pyridyl)-3-quinolinecarboxamide

Step 1

A mixture of 2-(2-aminobenzoyl)pyridine (4.36 g), diethyl malonate (3.92 ml) and 1,9-diazabicyclo[5.4.0]-7-undecene(0.5 ml) was heated for 3 hours at 180° C. The reaction mixture was cooled to give ethyl ester of 1,2-dihydro-2-oxo-4-(2-pyridyl)-3-quinolinecarboxylic acid as crystals (6.1 g: unrefined). The crystalline product was dissolved in DMF (100 ml), to which sodium hydride (60% oily) (1.5 g) was added, and the mixture was stirred for one hour at room temperature. The mixture was cooled to 0° C., to which was added, while stirring, iodomethane (10 ml). The mixture was stirred for one hour at room temperature, which was then concentrated. To the concentrate was added ethyl acetate. The mixture was washed with water and dried. The solvent was then distilled off. The residue was purified by means of a silica-gel column chromatography (ethyl acetate) to give ethyl eater of 1,2-dihydro-1-methyl-2-oxo-4-(2-pyridyl)-3-quinoline carboxylic acid as pale yellow crystals (2.6 g).

m.p.145°–146° C. (recrystallized from ethyl acetate-ethyl ether)

NM(200 MHz,CDCl$_3$): 1.03(3H,t,J=7.1 Hz), 3.81(3H,s), 4.12(2H,q,J=7.1 Hz), 7.18(1H,m), 7.30–7.52(4H,m), 7.62(1H,m), 7.83(1H,m), 8.77(1H,m)

Step 2

A mixture of the compound (1.0 g) obtained in Step 1 and 40% methylamine-methanol (30 ml) was heated for 16 hours in a sealed tube at 140° C. The solvent was distilled off. To the residue was added ethyl acetate, which was washed with a saturated aqueous saline solution and dried. The solvent was then distilled off to give the above titled compound as colorless crystals (0.60 g).

m.p.239°–240° C. (recrystallized from THF-ethyl ether)

NMR(200 MHz,CDCl$_3$): 2.81(3H,d,J=4.8 Hz), 3.84(3H, s), 7.02–7.20(2H,m), 7.30–7.50(3H,m), 7.64(1H,m), 7.81(1H,m), 8.73(1H,m), 8.81(1H,m)

Reference Example 15

7,8-Dihydro-7-methyl-8-oxo-5-phenyl-6-pyrido[3,4-b]pyridinecarboxylic acid

Step 1

To a mixture of 2,3-pyridine dicarboxylic anhydride (21.0 g) and benzene (210 ml) was added anhydrous aluminum chloride (30.0 g), which was stirred for 4 hours under reflux. The reaction mixture was cooled and poured into ice water-hydrochloric acid. Resulting crystalline precipitate was collected by filtration, which was washed with a small volume of water, then with ethyl ether to give 3-benzoyl-2-pyridine carboxylic acid hydrochloride as pale yellow crystals (23.7 g).

m.p.149°–153° C. (decomp.) (recrystallized from methanol-ethyl ether)

NMR(200 MHz,CDCl$_3$) ppm: 7.44(2H,t-like,J=7.9 Hz), 7.59(1H,m), 7.78(3H,m), 7.88(1H,dd,J=1.5,7.7 Hz), 8.78(1H,dd,J=1.5,4.7 Hz)

In Step 2 to 4, employing the compound obtained in Step 1,substantially the same reaction and work-up as in Reference Example 1 Process 1 Step 2 to 4 were conducted to give the respective compounds. The compounds and their physico-chemical constants of the respective steps are described below.

Step 2

3-Benzoyl-N-benzyloxycarbonylmethyl-N-methyl-2-pyridine carboxamide

A colorless oily product

NMR(200 MHz,CDCls) ppm: 3.12(3H×4/9,s), 3.18(3H×5/9,s), 4.24(2H×5/9,s), 4.26(2H×4/9H,s), 5.15(2H×5/9,s ), 5.18(2H×4/5,s), 7.23–7.85(7H,m), 8.40(1H×4/9,dd,J=1.4, 4.8 Hz), 8.74(1H×5/9,dd,J=1.4,4.8 Hz)

Step 3

7,8-Dihydro-7-methyl-8-oxo-5-phenyl-6-pyrido[3,4-b]pyridinecarboxylic acid benzyl ester m.p.127°–128° C. (recrystallized from dichloromethane-ethyl acetate)

NMR(200 MHz,CDCl$_3$) ppm: 3.63(3H,s), 4.99(2H,s), 7.03–7.08(2H,m), 7.23–7.55(9H,m), 7.62(1H,dd,J=1.4,8.3 Hz), 8.92(1H,dd,J=1.4,4.2 Hz)

Step 4

7,8-Dihydro-7-methyl-8-oxo-5-phenyl-6-pyrido[3,4-b]pyridinecarboxylic acid (above-titled compound)

m.p.230°–233° C. (decomp.) (recrystallized from methanol-ethyl ether)

NMR(200 MHz,CDCl$_3$) ppm: 3.50(3H,s), 7.10–7.80(7H, m), 8.82(1H,m)

Reference Example 16

1,2-Dihydro-2-methyl-1-oxo-4-phenyl-3-pyrido[3,4-c]pyridinecarboxylic acid

Step 1

To a suspension of 3,4-pyridinedidicarboxylic anhydride (8.94 g) in THF (100 ml) was added dropwise a solution of phenyl magnesium bromide (prepared from magnesium (2.02 g) and bromobenzene (11.30 g)) in THF (45 ml) while stirring at room temperature. The reaction mixture was stirred for one hour at room temperature, which was poured into a dilute hydrochloric acid with cooling. To this mixture was added an aqueous solution of sodium carbonate to adjust the pH to 2, followed by extraction with ethyl acetate. The extract solution was washed with water, which was dried, and then the solvent was distilled off to give 4-benzoyl-3-pyridinecarboxylic acid as a colorless crystalline product (5.80 g).

m.p.240°–241° C. (recrystallized from acetone)

NMR(200 MHz,CDCl$_3$+DMSO-d$_6$) ppm: 7.27–7.74(6H, m), 8.86(1H,d,J=4.0 Hz), 9.30(1H,s)

In the mother liquor and the washings, additional 4-benzoyl-3-pyridinecarboxylic acid and its isomer, 3-benzoyl-4-pyridinecarboxylic acid were present.

In Step 2 to 4, employing the compound obtained in Step 1,substantially the same reaction and work-up as in Reference Example 3 Step 2 to 4 were conducted to give the desired compounds. Compounds obtained in the respective steps and their physico-chemical constants are described below Step 2

4-Benzoyl-N-ethoxycarbonylmetyl-N-methyl-3-pyridine carboxamide

A pale yellow oily product

NMR(200 MHz,CDCl$_3$) ppm: 1.29(3H,t,J=7.2 Hz), 3.05(3H×1/4,s), 3.06(3H×3/4,s), 4.02(3H×1/4,s), 4.14(3H× 3/4,s), 4.21(2H,q,J=7.2 Hz), 7.27–7.80(4H,m), 7.81(2H,d, J=7.0 Hz), 8.78(2H,m)

Step 3

1,2-Dihydro-2-methyl-1-oxo-4-phenyl-3-pyrido[3,4-c]pyridinecarboxylic acid ethyl ester m.p.128°–130° C. (recrystallized from ethyl acetate-ethyl ether)

NMR(200 MHz,CDCl$_3$) ppm: 0.94(3H,t,J=7.0 Hz), 3.61(3H,s), 4.06(2H,q,J=7.0 Hz), 7.07(1H,d,J=5.6 Hz), 7.28–7.48(5H,m), 8.67(1H,d,J=5.6 Hz), 9.68(1H,s)

Step 4

1,2-Dihydro-2-methyl-1-oxo-4-phenyl-3-pyrido[3,4-c]pyridinecarboxylic acid (above-titled compound)

m.p.255°–257° C. (decomp.) (recrystallized from THF-methanol)

NMR(200 MHz,CDCl$_3$+DMSO-d$_6$) ppm: 3.67(3H,s), 7.05(1H,d,J=5.6 Hz), 7.35–7.49(5H,m), 8.64(1H,d,J=5.6 Hz), 9.62(1H,s)

Reference Example 17

5,6-Dihydro-6-methyl-5-oxo-8-phenyl-7-pyrido[4,3-b]pyridinecarboxylic acid

This compound was produced by employing, in place of p-fluorophenyl magnesium bromide in Reference Example 11 Step 1, phenyl magnesium bromide, and by subjecting the latter to substantially the same reaction and process as in Step 1 to 5 of Reference Example 11. The compounds obtained in the respective steps and their physico-chemical constants are described below.

Step 1

2-Benzoyl-3-pyridinecarboxylic acid m.p.190°–193° C. (recrystallized from methanol-ethyl ether)

NMR(200 MHz,CDCl$_3$) ppm: 7.28–7.63(4H,m), 7.76(2H,d-like,J=7 Hz), 8.37(1H,dd,J=1.6,8.0 Hz), 8.83(1H, dd,J=1.6,4.9 Hz)

Step 2

2-Benzoyl-N-cyanomethyl-N-methyl-3-pyridinecarboxamide

A pale yellow oily product

NMR(200 MHz,CDCl$_3$) ppm: 3.02(3H×3/4,s), 3.21(3H× 1/4,s), 4.18(2H×1/4,s), 4.50(2H×3/4,s), 7.35–7.70(4H,m), 7.79(1H,d-like,J=7.4 Hz),7.99(2H,m), 8.73(1H,dd,J=1.6,4.8 Hz)

Step 3

5,6-Dihydro-6-methyl-5-oxo-8-phenyl-7-pyrido[4,3-b]pyridinecarbonitrile m.p.256°–258° C. (recrystallized from methanol-ethyl ether)

NMR(200 MHz,CDCl$_3$) ppm: 3.88(3H,s), 7.45–7.60(6H, m), 8.79(1H,dd,J=1.9,8.1 Hz), 8.99(1H,dd,J=1.9,4.5 Hz)

Step 4

5,6-Dihydro-6-methyl-5-oxo-8-phenyl-7-pyrido[4,3-b]pyridinecarboxamide m.p.280°–282° C. (recrystallized from methanol-ethyl ether)

NMR(200 MHz,CDCl$_3$) ppm: 3.72(3H,s), 5.46(1H,b), 5.55(1H,b), 7.46(6H,m), 8.76(1H,dd,J=1.9,8.1 Hz), 8.91(1H,dd,J=1.9,4.5 Hz)

Step 5

5,6-Dihydro-6-methyl-5-oxo-8-phenyl-7-pyrido[4,3-b]pyridinecarboxylic acid (above titled compound)

m.p.254°–259° C. (decomp.) (recrystallized from methanol-ethyl ether)

NMR(200 MHz,DMSO-d$_6$) ppm: 3.55(3H,s), 7.28–7.50(5H,bs), 7.87(1H,d,J=4.8,8.0 Hz), 8.63(1H,dd,J= 1.8,8.2 Hz), 8.88(1H,dd,J=2.0,4.4 Hz)

Reference Example 18

4-(4-Fluorophenyl)-6,7-dihydro-1,6-dimethyl-7-oxo-5-pyrrolo[2,3-c]pyridinecarboxylic acid Step 1

1-Methyl-2,3-pyrroledicarboxylic anhydride and fluorobenzene were subjected to substantially the same reaction and process as in Reference Example 1 Process 1 in the presence of aluminum chloride to give 3-(4-fluorobenzoyl)-1-methyl-2-pyrrolecarboxylic acid as colorless crystals.

NMR(200 MHz,CDCl$_3$) ppm:4.11(3H,s), 6.51(1H,d,J= 2.9 Hz), 6.85(1H,d,J=2.9 Hz), 7.20(2H,t-like,J=8.6 Hz), 7.80–7.90(2H,m)

In Step 2 to 4, employing the compound obtained in Step 1, substantially the same reactions and processes as in Step 2 to 4 of Reference Example 2 were conducted to obtain the desired compounds. The compounds obtained in the respective steps and their physico-chemical constants are described below.

Step 2

N-Ethoxycarbonylmethyl-3-(4-fluorobenzoyl)-N,1-dimethyl-2-pyrrolecarboxamide A pale yellow oily product NMR(200 MHz,CDCl$_3$) ppm:1.22(0.9H,t,J=7.3 Hz), 1.31(2.1H, t,J=7.1 Hz), 2.93(2.1H,s), 3.08(0.9H,s), 3.30–3.90(1H,m), 3.74(2.1H,s), 4.00–4.50(1H,m), 4.12 (0.6H,q,J=7.3 Hz), 4.23(1.4H,q,J=7.1 Hz), 6.40 (0.3H,d,J= 2.6 Hz), 6.44(0.7H,d,J=2.8 Hz), 6.63 (0.3H,d,J=2.6 Hz), 6.66(0.7H,d,J=2.8 Hz), 7.12(2H,t-like,J=8.8 Hz), 7.78–7.92(2H,m)

Step 3

4-(4-Fluorophenyl)-6,7-dihydro-1,6-dimethyl-7-oxo-5-pyrrolo[2,3-c]pyridinecarboxylic acid ethyl ester A pale yellow oily product NMR(200 MHz,CDCl$_3$) ppm: 0.99(3H,t,J=7.2 Hz), 3.60(3H,s), 4.07(2H,q,J=7.2 Hz), 4.20(3H,s), 6.03(1H,d,J= 2.9 Hz), 6.98(1H,d,J=2.9 Hz), 7.00–7.40(4H,m)

Step 4

4-(4-Fluorophenyl)-6,7-dihydro-1,6-dimethyl-7-oxo-5-pyrrolo[2,3-c]pyridinecarboxylic acid (above-titled compound)

Colorless crystals

NMR(200 MHz,CDCl$_3$) ppm: 3.65(3H,s), 4.20(3H,s), 6.02(1H,d,J=2.8 Hz), 6.98(1H,d,J=2.8 Hz), 7.09(2H,t,J=8.8 Hz), 7.38–7.50(2H,m)

Reference Example 19

7-(4-Fluorophenyl)-4,5-dihydro-5-methyl-4-oxo-6-thiazolo[5,4-c]pyridinecarboxylic acid Step 1

4,5-Thiazoledicarboxylic anhydride and fluorobenzene were subjected to substantially the same reaction and process as in Reference Example 1 Process 1 Step 1 in the presence of aluminum chloride to give a mixture of 5-(4-fluorobenzoyl)-4-thiazolecarboxylic acid and 4-(4-fluorobenzoyl)-5-thiazolecarboxylic acid. This mixture was used in the subsequent Step 2.

Step 2

Employing the mixture obtained in Step 1, substantially the same reaction and process as in Reference Example 2 Step 2 were conducted to give a mixture of N-ethoxycarbonylmethyl-5-(4-fluorobenzoyl)-N-methyl-4-thiazolecarboxamide and N-ethoxycarbonylmethyl-4-(4-fluorobenzoyl)-N-methyl-5-thiazolecarboxamide as a pale yellow oily product.

NMR(200 MHz,CDCl$_3$) ppm: 1.20–1.40(3H,m), 3.00, 3.04,3.15, 3.23 (total 3H,each s), 4.00–4.40(4H,m), 7.16(2H,t-like,J=8.6 Hz), 7.84–7.95(1.2H,m), 8.24–8.34 (0.8H,m), 8.86,8.90,8.94,8.96(total 1H,each s) This mixture was used in the subsequent Step 3.

Step 3

Employing the mixture obtained in Step 2, substantially the same reaction and process as in Reference Example 2 Step 3 were conducted, then, the reaction mixture was refluxed in toluene in the presence of p-toluenesulfonic acid to give a mixture of 7-(4-fluorophenyl)-4,5-dihydro-5-methyl-4-oxo-6-thiazolo[5,4-c]pyridinecarboxylic acid ethyl ester and 7-(4-fluorophenyl)-4,5-dihydro-5-methyl-4-oxo-6-thiazolo[4,5-c]pyridinecarboxylic acid ethyl ester. This mixture was subjected to a silica-gel column chromatography (hexane-ethyl acetate=1:2). From the first fraction, the former was obtained as colorless crystals.

m.p.129°–130° C. (recrystallized from ethyl acetate-isopropyl ether)

NMR (200 MHz,CDCl$_3$) ppm:1.04(3H,t,J=7.1 Hz), 3.68(3H,s), 4.15(2H,q,J=7.1 Hz), 7.16(2H,t-like,J=8.7 Hz), 7.38–7.48(2H,m), 9.12(1H,s)

From the next fraction, the latter was obtained as colorless crystals.

m.p.209°–212° C. (recrystallized from ethyl acetate-isopropyl ether)

NMR (200 MHz,CDCl$_3$) ppm: 1.04(3H,t,J=7.1 Hz), 3.70(3H,s), 4.15(2H,q,J=7.1 Hz), 7.17(2H,t-like,J=8.6 Hz), 7.35–7.45(2H,m), 8.90(1H,s)

Step 4

7-(4-Fluorophenyl)-4,5-dihydro-5-methyl-4-oxo-6-thiazolo[5,4-c]pyridinecarboxylic acid ethyl ester obtained in Step 3 was subjected to hydrolysis in 70% H$_2$SO$_4$ at temperatures ranging from 120° to 130° C. to give the above-titled compound as colorless crystals.

m.p.214°–217° C. (recrystallized from ethyl acetate-isopropyl ether)

NMR(200 MHz,DMSO-d$_6$) ppm: 3.58(3H,s), 7.28(2H,t-like,J=9.0 Hz), 7.40–7.52(2H,m), 9.53(1H,s)

Reference Example 20

7-(4-Fluorophenyl)-4,5-dihydro-5-methyl-4-oxo-6-thiazolo[4,5-c]pyridinecarboxylic acid Employing 7-(4,5-dihydro-5-methyl-4-oxo-6-thiazolo[4,5-c]pyridinecarboxylic acid ethyl ester obtained in Reference Example 19 Step 3, substantially the same reaction (acid hydrolysis) as in Reference Example 19 Step 4 was conducted to give the above-titled compound as colorless crystals.

m.p.192°–194° C. (recrystallized from ethyl acetate THF-isopropyl ether)

NMR(200 MHz,DMSO-d$_6$) ppm: 3.57(3H,s), 7.34(2H,t-like,J=8.8 Hz), 7.46–7.57(2H,m), 9.23(1H,s)

Reference Example 21

4,5-Dihydro-5-methyl-4-oxo-7-phenyl-6-thiazolo[5,4-c]pyridinecarboxylic acid

Step 1

4,5-Thiazoledicarboxylic anhydride and benzene were subjected to substantially the same reaction and process as in Reference Example Process 1 Step 1 in the presence of aluminum chloride to give a mixture of 4-benzoyl-5-thiazolecarboxylic acid and 5-benzoyl-4-thiazolecarboxylic acid. This mixture was used in the subsequent Step 2

Step 2

Employing the mixture obtained in Step 1, substantially the same reaction and process as in Reference Example 2 Step 2 were conducted to give a mixture of 4-benzoyl-N-ethoxycarbonylmethyl-N-methyl-5-thiazolecarboxamide and 5-benzoyl-N-ethoxycarbonylmethyl-N-methyl-4-thiazolecarboxamide as a pale yellow oily product. This mixture was used in the subsequent Step 3.

Step 3

Employing the compound obtained in Step 2, substantially the same reaction and process as in Reference Example 19 Step 3 were conducted to give a mixture of 4,5-dihydro-5-methyl-4-oxo-7-phenyl-6-thiazolo[5,4-c]pyridinecarboxylic acid ethyl ester and 4,5-dihydro-5-methyl-4-oxo-7-phenyl-6-thiazolo[4,5-c]pyridinecarboxylic acid ethyl ester. This mixture was subjected to a silica-gel column chromatography (hexane-ethyl acetate=1:2). From the first fraction, the former was obtained as colorless crystals.

m.p.121°–122° C. (recrystallized from ethyl ether-isopropyl ether)

NMR(200 MHz,CDCl$_3$) ppm: 0.96(3H,t,J=7.1 Hz), 3.69(3H,s), 4.10(2H,q,J=7.1 Hz), 7.44(5H,s), 9.11(1H,s)

From the next fraction, the latter was obtained as colorless crystals.

m.p.186°–188° C. (recrystallized from ethyl acetate-isopropyl ether)

NMR(200 MHz,CDCl$_3$) ppm: 0.97(3H,t,J=7.1 Hz), 3.71(3H,s), 4.11(2H,q,J=7.1 Hz), 7.40–7.50(5H,m), 8.89(1H,s)

Step 4

Employing 4,5-dihydro-5-methyl-4-oxo-7-phenyl-6-thiazolo[5,4-c]pyridinecarboxylic acid ethyl ester, substantially the same reaction (acid hydrolysis) and process as in Reference Example 19 Step 4 were conducted to give the above-titled compound as colorless crystals.

m.p.155°–157° C. (recrystallized from ethyl acetate-isopropyl ether)

NMR(200 MHz,DMSO-d$_6$) ppm: 3.59(3H,s), 7.43(5H,s), 9.53(1H,s)

Reference Example 22

4,5-Dihydro-5-methyl-4-oxo-7-phenyl-6-thiazolo[4,5-c]pyridinecarboxylic acid 4,5-Dihydro-5-methyl-4-oxo-7-phenyl-6-thiazolo[4,5-c]pyridinecarboxylic acid ethyl ester obtained in Reference Example 21 Step 3 was subjected to substantially the same reaction and process as in Reference Example 19 Step 4 to give the above-titled compound as colorless crystals.

m.p.228°–230° C. (recrystallized from THF-ethyl ether)

NMR(200 MHz,DMSO-d$_6$) ppm: 3.58(3H,s), 7.48(5H,s), 9.23(1H,s)

Reference Example 23

6,7-Dihydro-6-methyl-7-oxo-4-phenyl-5-thieno[2,3-c]pyridinecarboxylic acid

Step 1

Employing 2,3-thiophene dicarboxylic anhydride and benzene, substantially the same reaction and work-up as in Reference Example 8 Step 1 in the presence of aluminum chloride were conducted to give 3-benzoyl-2-thiophenecarboxylic acid as colorless crystals.

m.p.141°–143° C. (recrystallized from ethyl acetate-isopropyl ether)

NMR(200 MHz,CDCl$_3$) ppm: 7.33(1H,d,J=5.4 Hz), 7.5–7.6(2H,m), 7.65(1H,d,J=5.4 Hz), 7.68(1H,m), 7.8–7.9(2H,m)

In Steps 2 to 4, employing the compound obtained in Step 1, substantially the same reaction and process as in Steps 2 to 4 of Reference Example 8 were conducted to give the desired compounds. The compounds obtained in the respective steps and their physico-chemical constants are described below.

Step 2

3-Benzoyl-N-ethoxycarbonylmethyl-N-methyl-2-thiophenecarboxamide

A pale yellow oily product

NMR(200 MHz,CDCl$_3$) ppm: 1.27(3H,t,J=7.2 Hz), 2.96(3H,bs), 4.00(2H,s), 4.19(2H,q,J=7.2 Hz), 7.27(1H,m), 7.4–7.6(4H,m), 7.83(2H,m)

Step 3

6,7-Dihydro-6-methyl-7-oxo-4-phenyl-5-thieno[2,3c]pyridinecarboxylic acid ethyl ester m.p.92°–94° C. (recrystallized from ethyl acetate)

NMR(200 MHz,CDCl₃) ppm: 0.94(3H,t,J=7.2 Hz), 3.67(3H,s), 4.07(2H,q,J=7.2 Hz), 6.97(1H,dd,J=5.2 Hz), 7.3–7.5(5H,m), 7.66(1H,d,J=5.2 Hz)

Step 4

6,7-Dihydro-6-methyl-7-oxo-4-phenyl-5-thieno[2,3c]pyridinecarboxylic acid (above-titled compound)

m.p.185°–186° C. (recrystallized from ethyl acetate)

NMR(200 MHz,CDCl₃) ppm: 3.65(3H,s), 6.95(1H,d,J=5.2 Hz), 7.40(5H,s), 7.65(1H,d,J=5.2 Hz)

Reference Example 24

6,7-Dihydro-6-methyl-4-(2-methylphenyl)-7-oxo-5-thieno[2,3-c]pyridinecarboxylic acid Step 1

2,3-Thiophenedicarboxylic anhydride was allowed to react with 2-methylphenyl magnesium bromide in THF, and the reaction mixture was processed to give 3-(2-methylbenzoyl)-2-thiophenecarboxylic acid as colorless crystals.

m.p.115°–117° C. (recrystallized from ethyl acetate-isopropyl ether)

NMR(200 MHz,CDCl₃) ppm: 2.42(3H,s), 7.17(1H,d,J=5.2 Hz), 7.3–7.5(4H,m), 7.56(1H,d,J=5.4 Hz)

In Steps 2 to 4, the compound obtained in Step 1 was subjected to substantially the same reactions and processes as in Step 2 to 4 of Reference Example 8 to give the desired compounds. The compounds obtained in the respective steps and their physico-chemical constants are described.

Step 2

N-Ethoxycarbonylmethyl-N-methyl-3-(2-methylbenzoyl)-2-thiophenecarboxamide

A pale yellow oily compound

NMR(200 MHz,CDCl₃) ppm: 1.28(3H,t,J=7.4 Hz), 2.42(3H,s), 2.97(3H×3/5,s), 3.01(3H×2/5,s), 3.99(2H×2/5,s), 4.07(2H×3/5,s), 4.22(2H,q,J=7.4 Hz), 7.2–7.5(6H,m)

Step 3

6,7-Dihydro-6-methyl-4-(2-methylphenyl)-7-oxo-5-thieno[2,3-c]pyridinecarboxylic acid ethyl ester A pale yellow oily substance NMR(200 MHz,CDCl₃) ppm: 0.88(3H,t,7.4 Hz), 2.12(3H,s), 3.67(2H,s), 4.01(2H,q,J=7.4 Hz), 6.71(1H,d,J=5.4 Hz), 7.2–7.3(4H,m), 7.63(1H,d,J=5.4 Hz)

Step 4

6,7-Dihydro-6-methyl-4-(2-methylphenyl)-7-oxo-5thieno[2,3-c]pyridinecarboxylic acid (above-titled compound)

m.p.124°–128° C. (recrystallized from ethyl acetate)

NMR (200 MHz,CDCl₃) ppm: 2.11(3H,s), 3.66(3H,s), 6.70(1H,d ,J=5.2 Hz), 7.2–7.3(4H,m), 7.64(1H,d,J=5.2 Hz)

Reference Example 25

7,8-Dihydro-7-methyl-5-(4-methylphenyl)-8-oxo-6pyrido[3,4-b]pyridinecarboxylic acid hydrochloride Step 1

Employing 2,3-pyridinedicarboxylic anhydride (10.0 g), toluene (125 ml) and aluminum chloride (15.0 g), substantially the same reaction and process as in Reference Example 1 Process 1 and Step 1 were conducted to give 3-(4-methylbenzoyl)-2-pyridinecarboxylic acid as colorless crystals (7.8 g).

m.p.168°–170° C. (recrystallized from dichloromethane-ethyl acetate)

NMR(200 MHz,CDCl₃) ppm: 2.41(3H,s), 7.24(2H,d,J=8.4 Hz), 7.62(2H,d,J=8.4 Hz), 7.70(1H,dd,J=8,4.8 Hz), 7.85(1H,dd,J=8,1.5 Hz), 8.77(1H,dd,J=4.8,1.5 Hz)

Step 2

Employing the compound obtained in Step 1, substantially the same reaction and process as in Reference Example 1 Process 2 Step 1 were conducted to give N-cyanomethyl-N-methyl-3-(4-methylbenzoyl)-2-pyridinecarboxamide as a pale brownish oily substance.

NMR(200 MHz,CDCl₃) ppm: 2.43(3H,s), 3.13(3H×1/3,s), 3.18(3H×2/3,s), 4.42(2H×2/3,s), 4.49(2H×1/3,s), 7.28(2H,d,J=8.4 Hz), 7.42–7.52(1H,m), 7.63–7.73(2H,m), 7.81–7.94(1H,m), 8.70–8.75(1H,m)

Step 3

Employing the compound obtained in Step 2, substantially the same reaction and process as in Reference Example 1 Process 1 and Step 2 were conducted to give 7,8-dihydro-7-methyl-5-(4-methylphenyl)-8-oxo-6-pyrido[3,4-b]pyridinecarbonitrile as colorless crystals.

m.p.268°–270° C. (recrystallized from ethyl acetate ethyl ether).

NMR(200 MHz,CDCl₃) ppm: 2.47(3H,s), 3.92(3H,s), 7.28(2H,d,J=8 Hz), 7.38(2H,d,J=8 Hz), 7.56(1H,dd,J=8,4 Hz), 7.75(1H,dd,J=8,2 Hz), 9.01(1H,dd,J=4,2 Hz)

Step 4

Employing the compound obtained in Step 3, substantially the same reaction and process as in Reference Example 1 Process 2 Step 3 were conducted to give 7,8-dihydro-7-methyl-5-(4-methylphenyl)-8-oxo-6-pyrido[3,4-b]pyridinecarboxamide as colorless crystals.

m.p.>310° C. (recrystallized from methanol).

NMR(200 MHz,CDCl₃+DMSO-d₆) ppm: 2.43(3H,s), 3.66(3H,s), 6.08(1H,b), 6.92(1H,b), 7.2–7.3(4H,m), 7.40(1H,dd,J=8,4 Hz), 7.56(1H,dd,J=8,2 Hz), 8.82(1H,dd, J=4,2 Hz)

Step 5

A mixture of the compound (7.3 g) obtained in Step 4), acetic acid (150 ml), hydrochloric acid (300 ml) and sodium nitrite (73 g) was stirred for 15 hours at room temperature. Resulting crystalline precipitate (inorganic salt) was separated by filtration and washed with hydrochloric acid. The filtrate and washing were combined and concentrated. This procedure was repeated three times to remove the inorganic salt. The residue was treated with THF to give the above-titled compound as yellow crystals (5.9 g).

m.p.178°–183° C. (after being softened, solidified in white), 249°–151° C. (decomp.) (recrystallized from methanol-THF)

NMR(200 MHz,CDCl₃+DMSO-d₆) ppm:2.43(3H,s), 3.77(3H,s), 7.29(4H,s), 7.88(1H,dd,J=8.5,4.8 Hz), 8.02(1H, dd,J=8.5,1.4 Hz), 9.04(1H,dd,J=4.8,1.4 Hz)

Reference Example 26

7,8-Dihydro-5-(4-methoxyphenyl)-7-methyl-8-oxo-6-pyrido [3,4-b]pyridinecarboxylic acid Step 1

Employing 2,3-pyridinedicarboxylic anhydride and 4-methoxyphenyl magnesium bromide, substantially the same reaction and process as in Reference Example 5 Step 1 were conducted to give a mixture of 3-(4-methoxybenzoyl)-2-pyridinecarboxylic acid and 2-(4-methoxybenzoyl)-

3-pyridinecarboxylic acid. This mixture was distributed into ethyl ether and 1N-HCl. The 1N-HCl layer was processed to give the former as a pale yellow powdery product.

NMR(200 MHz,CDCl$_3$+DMSO-d$_6$) ppm: 3.87(3H,s), 6.91(2H,d,J=8.6 Hz), 7.6(1H,m), 7.67(2H,d,J=8.6 Hz), 7.79(1H,d,J=9 Hz), 8.75(1H,b)

Step 2

Employing the compound obtained in Step 1, substantially the same reaction and process as in Reference Example 1 Process 2 Step 1 were conducted to give N-cyanomethyl-3-(4-methoxybenzoyl)-N-methyl-2-pyridinecarboxamide as a pale brownish oily substance.

NMR(200 MHz,CDCl$_3$) ppm:3.17(3H×1/4,s), 3.19(3H×3/4,s), 3.88(3H,s), 4.44(2H×3/4,s), 4.48(2H×1/4,s), 6.96(2H,d,J=8 Hz), 7.43–7.52(1H,m), 7.76–7.91(3H,m), 8.73(1H,dd,J=5,1.6 Hz)

Step 3

Employing the compound obtained in Step 2, substantially the same reaction and process as in Reference Example 1 Process 2 Step 2 were conducted to give 7,8-dihydro-5-(4-methoxyphenyl)-7-methyl-8-oxo-6-pyrido[3,4-b]pyridinecarbonitrile as colorless crystals.

m.p.248°–150° C. (recrystallized from ethanol)

NMR(200 MHz,CDCl$_3$) ppm: 3.90(3H,s), 3.91(3H,s), 7.08(2H,d,J=8.8 Hz), 7.33(2H,d,J=8.8 Hz), 7.57(1H,dd,J=8.2,4.4 Hz), 7.77(1H,dd,J=8.2,1.8 Hz), 9.01(1H,dd,J=4.4,1.8 Hz)

Step 4

Employing the compound obtained in Step 3, substantially the same reaction and process as in Reference Example 1 Process 2 Step 3 were conducted to give 7,8-dihydro-5-(4-methoxyphenyl)-7-methyl-8-oxo-6-pyrido[3,4-b]pyridinecarboxamide as colorless crystals.

m.p. >310° C. (recrystallized from methanol-THF)

NMR(200 MHz,CDCl$_3$+DMSO-d$_6$) ppm: 3.73(3H,s), 3.87(3H,s), 6.64(1H,b), 6.98(2H,d,J=8.8 Hz), 7.25(1H,b), 7.32(2H,d,J=8.8 Hz), 7.48(1H,dd,J=8.4,4.2 Hz), 7.63(1H,d,J=8.4,1.6 Hz), 8.86(1H,dd,J=4.2,1.6 Hz)

Step 5

Employing the compound obtained in Step 4, substantially the same reaction and process as in Reference Example 25 Step 5 were conducted to give the above-titled compound as a yellow powdery substance.

NMR(200 MHz,CDCl$_3$+DMSO-d$_6$) ppm:3.75(3H,s), 3.87(3H,s), 6.99(2H,d,J=8 Hz), 7.31(2H,d,J=8 Hz), 7.6–7.8(2H,m), 8.95(1H,b)

Reference Example 27

1,2-Dihydro-2-methyl-4-(4-methylphenyl)-1-oxo-3-pyrido[3,4-c]pyridinecarboxylic acid hydrochloride Process 1:
Step 1

Employing 3,4-pyridinecarboxylic anhydride (10.0 g) and 4-methylphenyl magnesium bromide, substantially the same reaction and process as in Reference Example 2 Step 1 were conducted to give 4-(4-methylbenzoyl)-3-pyridinecarboxylic acid as colorless crystals.

m.p.230°–231° C. (recrystallized from methanol)

NMR(200 MHz,CDCl$_3$) ppm: 2.41(3H,s), 7.24(2H,d,J=8.0 Hz), 7.28(1H,d,J=5.0 Hz), 7.63(2H,d,J=8.0 Hz), 8.84(1H,d,J=5.0 Hz), 9.30(1H,s)

Step 2

Employing the compound obtained by the method of Step 1,substantially the same reaction and process as in Reference Example 2 Step 2 were conducted to give N-ethoxycarbonylmethyl-N-methyl-4-(4-methylbenzoyl)-3-pyridinecarboxamide as a pale brownish oily substance.

NMR(200 MHz,CDCl$_3$) ppm: 1.29(3H,t,J=7.1), 2.43(3H,s), 3.05(3H,s), 4.00–4.20(2H,m), 4.22(2H,q,J=7.1 Hz), 7.25–7.40(1H,m), 7.28(2H,d,J=8.2 Hz), 7.71(2H,d,J=8.2 Hz), 8.71–8.83(2H,m)

Step 3

Employing the compound obtained in Step 2, substantially the same reaction and process as in Reference Example 2 Step 3 were conducted to give 1,2-dihydro-2-methyl-4-(4-methylphenyl)-1-oxo-3-pyrido [3,4-c]pyridinecarboxylic acid ethyl ester as colorless crystals.

m.p.134°–136° C. (recrystallized from ethyl acetate isopropyl ether)

NMR(200 MHz,CDCl$_3$) ppm: 0.99(3H,t,J=7.1 Hz), 2.43(3H,s), 3.61(3H,s), 4.09(2H,q,J=7.1 Hz), 7.09(1H,q,J=5.4 Hz), 7.18(2H,d,J=8.2 Hz), 7.27(2H,d,J=8.2 Hz), 8.66(1H,d,J=5.4 Hz), 9.68(1H,s)

Step 4

Employing the compound obtained in Step 3, substantially the same reaction and work-up (treatment with HCl was added) as in Reference Example 2 Step 4 were conducted to give the above-titled compound as yellow crystals.

m.p.240°–242° C. (solidified again, decomposed around 280° C.) (recrystallized from methanol-THF)

NMR(200 MHz,DMSO-d$_6$) ppm: 2.40(3H,s), 3.57(3H,s), 7.26(2H,d,J=8.0 Hz), 7.34 (1H,d,J=6.4 Hz), 7.35(2 H,d,J=8.0 Hz), 8.75(1H,d,J=6.4 Hz), 9.53(1H,s)

Process 2:
Step 1

Employing the compound obtained in Step 1, substantially the same reaction and process as in Reference Example 1 Process 2 Step 1 were conducted to give N-cyanomethyl-N-methyl-4-(4-methylbenzoyl)-3-pyridinecarboxamide as a pale brownish oily product.

NMR(200 MHz,CDCl$_3$) ppm: 2.44(3H,s), 3.10(3H,s), 4.38(2H,bs), 7.30(2H,d,J=8.2 Hz), 7.43(1H,d,J=5.0 Hz), 7.70(2H,d,J=8.2 Hz), 8.75(1H,s), 8.88(1H,d,J=5.0 Hz)

Step 2

Employing the compound obtained in Step 1, substantially the same reaction and process as in Reference Example 1 Process 2 Step 2 were conducted to give 1,2-dihydro-2-methyl-4-(4-methylphenyl)-1-oxo-3-pyrido[3,4-c]pyridinecarbonitrile as colorless crystals.

m.p.201°–202° C. (recrystallized from ethyl acetate-isopropyl ether)

NMR(200 MHz,CDCl$_3$) ppm: 2.47(3H,s), 3.86(3H,s), 7.20(1H,d,J=5.9 Hz), 7.29(2H,d,J=8.2 Hz), 7.38(2H,d,J=8.2 Hz), 8.79(1H,d,J=5.9 Hz), 9.73(1H,s)

Step 3

Employing the compound obtained in Step 2, substantially the same reaction and process as in Reference Example 1 Process 2 Step 2 were conducted to give 1,2-dihydro-2-methyl-4-(4-methylphenyl)-1-oxo-3-pyrido[3,4-c]pyridinecarboxamide as a colorles crystals.

m.p.329°–330° C. (recrystallized from dichloromethane methanol)

NMR(200 MHz,DMSO-d$_6$) ppm: 2.38(3H,s), 3.54(3H,S) 6.97(1H,d,J=5.4 Hz), 7.23(2H,d,J=8.6 Hz), 7.29(2H,d,J=8.6 Hz), 7.85(1H,bs), 8.11(1H,bs), 8.66(1H,d,J=5.4Hz), 9.44(1H,s)

Step 4

Employing the compound obtained in Step 3, substantially the same reaction and process as in Reference Example 25 Step 5 were conducted to give the above-titled compound as yellow crystals. The physico-chemical constants of this compounds are in good agreement with those of the compound obtained in Process 1
Step 4

Reference Example 28

7,8-Dihydro-7-methyl-5-(3-methylphenyl)-8-oxo-6-pyrido [3,4-b]pyridinecarboxylic acid hydrochloride Step 1

Employing 2,3-pyridinecarboxylic anhyride and 3-methylphenyl magnesium bromide, substantially the same reaction and process as in Reference Example 5 Step 1 were conducted to give a mixture of 3-(3-methylbenzoyl)-2-pyridinecarboxylic acid and 2-(3-methylbenzoyl)-3-pyridinecarboxylic acid.

Step 2

Employing the mixture obtained in Step 1, substantially the same reaction and process as in Reference Example 1 Process 2 Step 1 were conducted to give a mixture of N-cyanomethyl-N-methyl-3-(3-methyl benzoyl)-2-pyridine carboxamide and N-cyanomethyl-N-methyl-2-(3-methylbenzoyl)-3-pyridinecarboxamide.

Step 3

Employing the mixture obtained in Step 2, substantially the same reaction and process as in Reference Example 1 Process 2 Step 2 were conducted. The reaction mixture was subjected to a silica-gel column chromatography (acetone-:hexane=1:1→ acetone) to fractionate. From the first fraction, 5,6-dihydro-6-methyl-8-(3-methylphenyl)-5-oxo-7-pyrido[4,3-b]pyridine carbonitrile [m.p.:234°–236° C. (recrystallized from acetone), NMR(200 MHz,CDCl$_3$) ppm: 2.44(3H,s), 3.87(3H,s), 7.26–7.47(4H,m), 7.54(1H,dd,J=8.5 Hz), 8.78(1H,dd,J=8,2 Hz), 8.99(1H,dd,J=5,2 Hz)], and, from the next fraction, 7,8-dihydro-7-methyl-5-(3-methylphenyl)-8-oxo-6-pyrido[3,4-b]pyridinecarbonitrile [m.p.:253°–255° C. (recrystallized from acetone), NMR(200 MHz,CDCl$_3$) ppm: 2.45(3H,s), 7.2–7.5(4H, m), 7.57(1H,dd,J=8,4 Hz), 7.73(1H,d,J=8 Hz), 9.02(1H,d, J=4 Hz)]were respectively obtained as colorless crystals.

Step 4

Employing 7,8-dihydro-7-methyl-5-(3-methylphenyl)-8-oxo-6-pyrido[3,4-b]pyridinecarbonitrile obtained in Step 3,substantially the same reaction and process as in Reference Example 1 Process 2 Step 3 were conducted to give 7,8-dihydro-7-methyl-5-(3-methylphenyl)-8-oxo-6-pyrido[3,4-b]pyridinecarboxamide as colorless crystals.

m.p.>310° C. (recrystallized from methanol)

NMR(200 MHz,CDCl$_3$) ppm: 2.42(3H,s), 3.57(3H,s), 5.70(1H,bs), 6.78(1H,bs),7.23–7.41(5H,m), 7.52(1H,dd,J= 8,2 Hz), 8.79(1H,dd,J=4,2 Hz)

Step 5

Employing the compound obtained in Step 4, substantially the same reaction and process as in Reference Example 25 Step 5 were conducted to give the above-titled compound as pale yellow orange crystals.

m.p. around 220° C. (decomp.) (recrystallized from methanol-THF)

NMR(200 MHz,CDCl$_3$+DMSO-d$_6$) ppm: 2.41(3H,s), 3.78(3H,s), 7.22–7.42(4H,m), 7.95(1H,dd,J=8,4 Hz), 8.07(1H,d,J=8 Hz), 9.09(1H,d,J=4 Hz)

Reference Example 29

5-(4-Carboxyphenyl)-7,8-dihydro-7-methyl-8-oxo-6-pyrido[3,4-b]pyridinecarboxylic acid Step 1

To a mixture of 3-(4-methylbenzoyl)-2-pyridinecarboxylic acid (6.0 g) and 0.1N-NaOH (340 ml) was added portionwise KMnO$_4$ (8.0 g), while stirring at room temperature. After this mixture was heated at 90°–100° C. for 1.5 hour, isopropanol was added to the mixture, and the resulting precipitate was filtered off. To the filtrate was added c.HCl to adjust the pH 2. The solution was saturated with NaCl and extracted with ethyl acetate-THF (about 3:1). The extract was washed with ag. NaCl, dried, and the solvent was evaporated to give 3-(4-carboxybenzoyl)-2-pyridinecarboxylic acid as colorless crystals (1.50 g).

m.p. 210°–213° C. (decomp.) recrystallized from THF-isopropyl ether)

NMR(200 MHz,CDCl$_3$+DMSO-d$_6$) ppm: 7.64(1H,dd,J= 4.8, 7.8 Hz), 7.77(2H,d,J=8.6 Hz), 7.83(1H,dd,J=7.8,1.6 Hz), 8.10(2H,d,J=8.6 Hz), 8.86(1H,dd,J=4.8,1.6 Hz)

Step 2

Using the compound obtained in Step 1 (1.46 g) and N-methylglycine ethylester (3.0), substantially the same reaction and work-up as in Reference Example 2-Step 2 were conducted to give N-ethoxycarbonylmethyl-3-[4-(N-ethoxycarbonylmethyl-N-methylcarbamoyl)benzoyl]-N-methyl-2-pyridinecarboxamide as a colorless oil (2.5 g)

NMR(200 MHz,CDCl$_3$) ppm: 1.20–1.40(6H,m), 3.02, 3.13, 3.21(total 6H, each s), 3.96, 4.10–4.40(total 8H,m), 7.40–7.60(3H,m) 7.70–7.90(3H,m), 8.63(1H×2/5,d-like), 8.75(1H×3/5,d-like)

Step 3

Using the compound obtained in step 2 (2.2 g) and 1,8-diazabicyclo[5.4.0]undec-7-ene (2 ml), substantially the same reaction and work-up as in Reference Example 2-Step3 were conducted to give 5-[4-(N-ethoxycarbonylmethyl-N-methylcarbamoyl)phenyl]-7,8-dihydro-7-methyl-8-oxo-6-pyrido[3,4b]pyridinecarboxylic acid ethyl ester as colorless crystals (0.82 g).

m.p. 195°–197° C. (recrystallized from ethyl acetateisopropyl ester)

NMR(200 MHz,CDCl$_3$) ppm: 1.01(3H,t,J=7.1 Hz), 1.30(1H,t,J=7.2 Hz), 1.34(2H,t,J=6.8 Hz), 3.12(2H,s), 3.17(1H,s), 3.68(3H,s), 4.09(2H,q,J=7.1 Hz), 4.15–4.35(4H, m), 7.10–7.65(6H,m), 8.94(1H,dd,J=4.0,1.2 Hz)

Step 4

Using the compound obtained in Step 3 (0.77 g), substantially the same reaction and work-up as in Reference Example 2-Step 4 were conducted to give the above-titled compound as a pale yellow oil, which was used for the reaction of Example 73.

Reference Example 30

5-Cyclohexyl-7,8-dihydro-7-methyl-8-oxo-6-pyrido[3,4-b]pyridinecarboxylic acid

Starting from 3-cyclohexylcarbonyl-2-pyridinecarboxylic acid, which was prepared from 2,3-pyridinedicarboxylic anhydride and cyclohexylmagnesium chloride, substantially the same reaction and work-up as in Reference Exampe 1-Process 2-Step 1 to Step 4 were conducted to give the title compound as a pale yellow oil, which was used for the reaction of Example 76.

Reference Example 31

7,8-Dihydro-7-methyl-5-(4-methylphenyl)-8-oxo-6-pyrido[3,4-b]pyridinecarboxylic acid hydrochloride Step 1

To a mixture of 2,3-pyridinedicarboxylic anhydride (1.50 g) and THF (25 ml) was added dropwise, while stirring at room temperature, methylaminoacetaldehyde dimethyl acetal (2.90 ml). The mixture was stirred for 3 hours at room temperature and then concentrated. To the concentrate were added dichloromethanepotassium hydrogen sulfate (2.7 g) and water. The dichloromethane layer was separated, and the aq. layer was extracted with dichloromethane. The organic layers were combined, washed with aq. NaCl, dried and evaporated to give 2-[N-(2,2-dimethoxyethyl)-N-methyl]carbamoyl-3-pyridinecarboxylic acid as colorless crystals (2.10 g).

m.p. 128°–130° C. (decomp.) (recrystallized from acetoneethyl ether).

Step 2

To a stirred solution of the compound (1.35 g) obtained in Step 1, potassium carbonate (0.42 g) and acetone (30 ml) was added iodomethane (1.0 ml). The mixture was stirred for 14 hours at room temperature, and concentrated. To the concentrate was added dichloromethane. The mixture was washed with water, dried and the solvent evaporated to give 2-[N-(2,2-dimethoxyethyl)-N-methyl]carbamoyl-3-pyridinecarboxylic acid methyl ester as a pale yellow oil (0.90 g).

NMR(200 MHz,CDCl$_3$) ppm: 2.90(3H×2/3,s), 3.23(3H×1/3,s), 3.23(2H×1/3,d,J=5 Hz), 3.29(3H×2/3,s), 3.51(3H×2/3+3H×1/3×2,s) 3.68(2H×2/3,d,J=5 Hz), 3.92(3H×1/3,s), 3.93(3H×2/3,s), 4.54(1H×1/3,t,J=5 Hz), 4.77(1H×2/3,t,J=5 Hz), 7.42(1H,dd,J=5.8 Hz), 8.31(1H×1/3,dd,J=2.8 Hz), 8.32(1H×2/3,dd,J=2,8 Hz), 8.73(1H×1/3,dd,J=2,5 Hz), 8.76(1H×2/3,dd,J=2,5 Hz).

Step 3

To a mixture of magnesium (2.0 g), iodine (catalytic amount) and THF (20 ml), while stirring at room temperature, was added dropwise a solution of 4-bromotoluene (12 g) in THF (30 ml), and the mixture was stirred for 30 minutes. The mixture was added dropwise, while stirring at −78° C., to a solution of the compound (5.8 g) obtained by the method described in Step 2 in THF (100 ml), followed by stirring for 30 minutes at −78° C. To the mixture was added aq. NaCl, and the mixture was extracted with ethyl acetate. The extract was washed with water, dried and the solvent was evaporated to give N-(2,2-dimethoxyethyl)-N-methyl-3-(4-methylbenzoyl)-2-pyridinecarboxamide as a pale brown oil, which was subjected to the reaction of Step 4 without purification.

NMR(200 MHz,CDCl$_3$) ppm: 2.43(3H,s), 3.09(3H×1/3,s), 3.11(3H×2/3,s), 3.37(6H×1/3,s), 3.44(6H×2/3,s), 3.50(2H×2/3,d,J=5.6 Hz), 3.52(2H×1/3,d,J=5.4 Hz), 4.51(1H×2/3,t,J=5.6 Hz), 4.77(1H×1/3,t,J=5.4 Hz), 7.27(2H,d,J=8.0 Hz), 7.40(1H,dd,J=7.8,4.8 Hz), 7.71(2H,d,J=8.0 Hz),8.76–8.87(1H,m), 8.65–8.75(1H,m).

The physico-chemical constants of this compound was idential with those of the compound obtained by amidation of 3-(4-methylbenzoyl)-2-pyridinecarboxylic acid (via the acid chloride) with methylaminoacetaldehyde dimethyl acetal.

Step 4

A mixture of the compound (crude) obtained in Step 3, THF (30 ml), H$_2$O (30 ml) and c.HCl (20 ml) was stirred for 1 hour at room temperature. After being washed with ethyl acetate, the mixture was treated with aq. K$_2$CO$_3$ to adjust the pH 9–10, and then extracted with ethyl acetate. The extract was washed with water, dried and the solvent was evaporated to give N-formylmethyl-N-methyl-3-(4-methylbenzoyl)-2pyridinecarboxamide as a pale brown oil (3.2 g).

NMR(200 MHz,CDCl$_3$) ppm: 2.43(3H,s), 3.16(3H×2/5, s),
3.17(3H×3/5,s ), 4.14(2H,m), 7.28(2H,d,J=8.0 Hz), 7.35–7.50 (1H,m), 7.70(2H,d,J=8.0 Hz), 7.79 (1H×2/5,dd, J=7.8,1.6 Hz), 7.88 (1H×3/5,dd,J=7.8,1.6 Hz) 8.61 (1H×2/5,dd,J=5.0,1.6 Hz), 8.75 (1H×3/5,dd,J=5.0,1.6 Hz), 9.52(1H×3/5,m), 9.88 (1H×2/5,m).

Step 5

A mixture of the compound obtained in Step 4 (3.0 g), toluene (60 ml) and 1,8-diazabicyclo [5.4.0]undec-7-ene (0.3 ml) was stirred for 30 minutes under reflux. The mixture was cooled, and the crystals separated were collected by filtration, washed with ethyl ether to give 7,8-dihydro-7-methyl-5-(4-methylphenyl)-8-oxo-6-pyrido[3,4-b]pyridinecarboxaldehyde as pale yellow crystals (1.98 g).

m.p. 282°–284° C. (recrystallized from THF-isopropyl ether)

NMR(200 MHz,CDCl$_3$) ppm: 2.48(3H,s), 3.95(3H,s), 7.24(2H,d,J=8.0 Hz), 7.36(2H,d,J=8.0 Hz), 7.53(1H,dd,J=8.2,4.4 Hz), 7.68(1H,dd,J=8.2,1.6 Hz), 9.01(1H,dd,J=4.4, 1.6 Hz), 9.61(1H,s)

Step 6

To a mixture of the compound obtained in Step 5 (1.0 g), 0.25N-NaOH (20 ml) and 2-methyl-2-propanol (20 ml) was added potassium permanganate (0.6 g) while stirring at 0° C. and the mixture was added EtOH (5 ml), followed by stirring for 10 min. After the resulting precipitate was filtered off, the filtrate was treated with C.HCl to adjust the pH 2, and then the solvent was evaporated to give the above-titled compound as yellow crystals (1.1 g), whose physico-chemical constants were identical with those of the compound obtained in Reference Example 25.

Formulation Example 1

Coated Tablets (1000 tablets)

Compound of Example 1 10.0 g

Lactose 60.0 g

Corn starch 35.0 g

Gelatine 3.0 g

Magnesium stearate 2.0 g

A mixture of the compound obtained in Example 1, lactose and corn starch was granulated, using a 10% aqueous solution of gelatine, through a sieve of 1 mm, which was dried at 40° C. and sieved again. Thus-obtained granules were mixed with magnesium stearate, which was compressed. Thus-obtained core-tablets were subjected to sugar-coating with an aqueous suspension of sucrose, titanium dioxide, talc and an aqueous solution of gum arabica. Thus-coated tablets were polished with bees wax.

Formulation Example 2

Tablets (1000 tablets)

Compound of Example 1 10.0 g

Lactose 70.0 g

Corn starch 50.0 g

Soluble starch 7.0 g

The compound obtained in Example 1 and magnesium stearate were granulated with an aqueous solution of soluble starch and dried. The granules were mixed with lactose and corn starch. The mixture was compressed into tablets.

Effects of the Invention

The compounds of this invention have an excellent tachykinin receptor antagonist activity and an inhibitory activity of plasma extravasation due to capsaicin, thus being widely used as medicines such as a treating or ameliorating agent of disorders of micturition.

What is claimed is:

1. A compound represented by the formula:

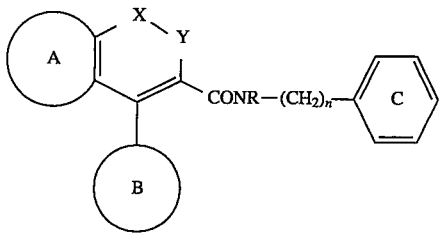

wherein Ring A and Ring B respectively stand for an optionally substituted homo- or hetero-cyclic ring, and at least one of A and B stands for an optionally substituted heterocyclic ring which contains one hetero atom;

Ring C stands for an optionally substituted benzene ring;

R stands for a hydrogen atom or an optionally substituted hydrocarbon residue;

either one of X and Y is $-NR^1-$, wherein $R^1$ is a hydrogen atom or an optionally substituted hydrocarbon residue, and the other is $-CO-$ or $-CS-$, or either one of X and Y is $-N=$ and the other is $=CR^2-$, wherein $R^2$ is a hydrogen atom, a halogen atom, an optionally substituted hydrocarbon residue, an optionally substituted amino group or an optionally substituted hydroxyl group;

n denotes 1 or 2, or a pharmaceutically acceptable salt thereof.

2. A compound as claimed in claim 1, in which either one of Ring A and Ring B stands for an optionally substituted aromatic ring and the other stands for an optionally substituted aromatic heterocyclic ring.

3. A compound as claimed in claim 2, in which the substituent or substituents of the optionally substituted aromatic ring are 1 to 4 substituents selected from the group consisting of a halogen atom, an optionally halogenated $C_{1-4}$ alkyl group, an optionally halogenated $C_{1-4}$ alkoxy group, an optionally halogenated $C_{1-4}$ alkylthio group, a $C_{1-3}$ acyloxy group, a hydroxyl group, an amino group, a mono-$C_{1-4}$ alkyl amino group, di-$C_{1-4}$ alkylamino group, carboxyl group and $C_{1-4}$ alkoxy-carbonyl group.

4. A compound as claimed in claim 2, wherein the aromatic heterocyclic ring is a 5- or 6-membered ring containing one hetero atom selected from nitrogen atom, sulfur and oxygen.

5. A compound as claimed in claim 2, in which the substituent or substituents of the optionally substituted aromatic heterocyclic ring are 1 to 4 substituents selected from the group consisting of a halogen atom, an optionally halogenated $C_{1-4}$ alkyl group, an optionally halogenated $C_{1-4}$ alkoxy group, an optionally halogenated $C_{1-4}$ alkylthio group, $C_{1-3}$ acyloxy group, a hydroxyl group, an amino group, a mono-$C_{1-4}$ alkylamino group, a di-$C_{1-4}$ alkylamino group, a carboxyl group and a $C_{1-4}$ alkoxy-carbonyl group.

6. A compound as claimed in claim 1, in which the Ring C may be substituted by 1 to 3 substituents, each being selected from the group consisting of a halogen atom, an optionally halogenated $C_{1-4}$ alkyl group and an optionally halogenated $C_{1-4}$ alkoxy group.

7. A compound as claimed in claim 1, wherein $-X-Y-$ is $-NR^{1a}-CO-$, $-CO-NR^{1a}-$, or $-N=C(R^{2a})-$ ($R^{1a}$ and $R^{2a}$ respectively stand for a hydrogen atom or a $C_{1-6}$ alkyl group).

8. A compound as claimed in claim 1, in which R is a $C_{1-6}$ alkyl group.

9. A compound claimed in claim 1, in which n is 1.

10. A compound as claimed in claim 1, in which the substituent or substituents of the optionally substituted homo- or hetero-cyclic ring are 1 to 4 substituents selected from the group consisting of a halogen atom, an optionally halogenated $C_{1-4}$ alkyl group, an optionally halogenated $C_{1-4}$ alkylthio group, a $C_{1-3}$ acyloxy group, a hydroxyl group, an amino group, a mono-$C_{1-4}$ alkylamino group, di-$C_{1-4}$ alkylamino group, a carboxyl group, a $C_{1-4}$ alkoxycarbonyl group and an oxo group.

11. A compound as claimed in claim 1, wherein the heterocyclic ring is a 5- or 6-membered ring containing one hetero atom selected from nitrogen, sulfur and oxygen.

12. A compound as claimed in claim 1, in which the homo-cyclic ring is a 5- or 6-membered cyclic hydrocarbon.

13. A compound as claimed in claim 1, in which $-X-Y-$ is $-NR^{1a}-CO-$, $-CO-NR^{1a}-$ or $-N=C(R^{2a})-$ ($R^{1a}$ and $R^{2a}$ respectively stand for a hydrogen atom or a $C_{1-6}$ alkyl group).

14. A compound as claimed in claim 1, in which the heterocyclic ring represented by Ring A or B is a 5- or 6-membered heterocyclic ring containing 1 hetero-atom selected from nitrogen and sulfur, the homocyclic ring represented by Ring A or B is a 5- or 6-membered cyclic hydrocarbon group, and the hetero- and homo-cyclic ring represented by Ring A or B respectively may be substituted by 1 or 2 substituents selected from the group consisting of a halogen atom and an optionally halogenated $C_{1-4}$ alkyl group;

Ring C may be substituted by 1 to 3 substituents selected from the group consisting of a halogen atom, an optionally halogenated $C_{1-4}$ alkyl group and an optionally halogenated $C_{1-4}$ alkoxy group;

R is a hydrogen atom or a $C_{1-4}$ alkyl group; $-X-Y-$ is $-CO-NR^{1a}-$, $-NR^{1a}-CO$ or $-N=C(R^{2a})-$ ($R^{1a}$ and $R^{2a}$ respectively stand for a hydrogen atom or a $C_{1-4}$ alkyl group); and n is 1.

15. A compound as claimed in claim 1, in which Ring A is a pyridine ring;

Ring B is a benzene ring which may be substituted by 1 to 3 substituents selected from the group consisting of a halogen atom, an optionally halogenated $C_{1-4}$ alkyl group and an optionally halogenated $C_{1-4}$ alkoxy group;

Ring C may be substituted by 1 to 3 substituents selected from the group consisting of a halogen atom, an optionally halogenated $C_{1-4}$ alkyl group and an optionally halogenated $C_{1-4}$ alkoxy group;

R is a hydrogen atom or a $C_{1-6}$ alkyl group;

X is $-CO-$;

Y is $-NR^{1a}-$ ($R^{1a}$ stands for a hydrogen atom or a $C_{1-6}$ alkyl group); and n is 1.

16. N-[3,5-Bis(trifluoromethyl)benzyl]-4-(4-fluorophenyl)-6,7-dihydro-N,6-dimethyl-7-oxo-5-thieno[2,3-c]pyridinecarboxamide.

17. N-[3,5-Bis(trifluoromethyl)benzyl]-1,2,5,6,7,8-hexahydro-N,2,7-trimethyl-4-(4-methylphenyl)-1-oxo-3-pyrido[3,4-c]pyridinecarboxamide.

18. N-[3,5-Bis(trifluoromethyl)benzyl]-7,8-dihydro-N,7-dimethyl-5-(4-methylphenyl)-8-oxo-6-pyrido[3,4-b]pyridinecarboxamide.

19. N-[3,5-Bis(trifluoromethyl)benzyl]-5-(4-fluorophenyl)-7,8-dihydro-N, 7-dimethyl-8-oxo-6-pyrido[3,4-b]pyridinecarboxamide.

20. A process for producing a compound as claimed in claim 1, which comprises reacting a compound represented by the formula:

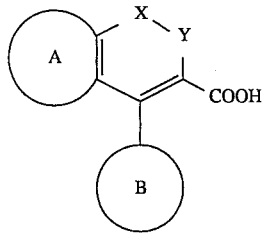

wherein all symbols are of the same meanings as defined in claim 1 or a salt thereof or a reactive derivative thereof with a compound represented by the formula:

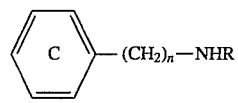

wherein all symbols are of the same meaning as defined in claim 1 or a salt thereof.

21. A tachykinin receptor antagonist composition which comprises an antagonist effective amount of a compound as claimed in claim 1 and a carrier.

22. A composition for treating disorders of micturition which comprises a micturition effective amount of a compound as claimed in claim 1 and a carrier.

23. A composition for inhibiting plasma extravasation which comprises an effective amount for inhibiting extravasation of a compound as claimed in claim 1 and a carrier.

24. Method for antagonizing a tachykinin receptor in mammals which comprises administering to a subject in need an effective amount of a compound as claimed in claim 1.

25. N-[3,5-Bis (trifluoromethyl) benzyl]-7,8-dihydro-N, 7-dimethyl-5-(3-methylphenyl)-8-oxo-6-pyrido[3,4-b]pyridinecarboxamide.

* * * * *